US008855744B2

(12) United States Patent
Tolkowsky et al.

(10) Patent No.: US 8,855,744 B2
(45) Date of Patent: Oct. 7, 2014

(54) DISPLAYING A DEVICE WITHIN AN ENDOLUMINAL IMAGE STACK

(71) Applicant: Sync-Rx, Ltd., Netanya (IL)

(72) Inventors: David Tolkowsky, Tel Aviv (IL); Eldad Klaiman, Herzlia (IL); Alexander Steinberg, Ra'anana (IL); Ran Cohen, Petah Tikva (IL)

(73) Assignee: Sync-RX, Ltd., Netanya (IL)

( * ) Notice: Subject to any disclaimer, the term of this patent is extended or adjusted under 35 U.S.C. 154(b) by 0 days.

(21) Appl. No.: 14/097,603

(22) Filed: Dec. 5, 2013

(65) Prior Publication Data

US 2014/0094690 A1    Apr. 3, 2014

Related U.S. Application Data

(63) Continuation of application No. PCT/IL2013/050438, filed on May 21, 2013, and a continuation-in-part of (Continued)

(51) Int. Cl.
| | | |
|---|---|---|
| A61B 5/05 | (2006.01) | |
| A61B 8/12 | (2006.01) | |
| G06T 7/00 | (2006.01) | |
| A61B 8/08 | (2006.01) | |
| A61B 5/00 | (2006.01) | |
| A61B 5/06 | (2006.01) | |

(52) U.S. Cl.
CPC ............ A61B 5/0084 (2013.01); *A61B 5/0075* (2013.01); *A61B 5/0086* (2013.01); A61B 8/12 (2013.01); *A61B 5/7425* (2013.01); *A61B 5/066* (2013.01); *G06T 7/0024* (2013.01); A61B 8/0841 (2013.01); *A61B 5/061* (2013.01); *A61B 5/0066* (2013.01); *A61B 5/0073* (2013.01); *A61B 5/064* (2013.01)
USPC ............ 600/428; 600/407; 600/415; 600/429

(58) Field of Classification Search
None
See application file for complete search history.

(56) References Cited

U.S. PATENT DOCUMENTS 3,871,360 A   3/1975   Van Horn et al.
3,954,098 A   5/1976   Dick et al.
(Continued)

FOREIGN PATENT DOCUMENTS

EP   2 570 079 A1   3/2013
WO   94/10904      5/1994
(Continued)

OTHER PUBLICATIONS

Boyle et al., entitled "Assessment of a Novel Angiographic Image Stabilization System for Percutaneous Coronary Intervention" (Journal of Interventional Cardiology, vol. 20 No. 2, 2007.

(Continued)

*Primary Examiner* — Joel Lamprecht
(74) *Attorney, Agent, or Firm* — Sughrue Mion, PLLC

(57) ABSTRACT

Apparatus and methods are described including, while an endoluminal data-acquisition device is being moved through a subject's lumen, acquiring a plurality of endoluminal data points of the lumen using the endoluminal data-acquisition device. It is determined that respective endoluminal data points correspond to respective locations along the lumen. A display is driven to display at least some of the plurality of endoluminal data points in a stack. While a second endoluminal device is inside the lumen, a current location of at least a portion of the second endoluminal device with respect to the lumen is determined. In response thereto, an image of the second endoluminal device is displayed within the stack, at a location within the stack corresponding to the current location of the second endoluminal device. Other applications are also described.

24 Claims, 8 Drawing Sheets

Related U.S. Application Data application No. 13/228,229, filed on Sep. 8, 2011, which is a continuation of application No. PCT/IL2011/000612, filed on Jul. 28, 2011, said application No. PCT/IL2013/050438 is acontinuation-in-part of application No. 12/666,879, filed as application No. PCT/IL2009/001089 on Nov. 18, 2009, now Pat. No. 8,781,193.

(60) Provisional application No. 61/688,730, filed on May 21, 2012, provisional application No. 61/761,709, filed on Feb. 7, 2013, provisional application No. 61/344,464, filed on Jul. 29, 2010, provisional application No. 61/344,875, filed on Nov. 1, 2010, provisional application No. 61/457,339, filed on Mar. 3, 2011, provisional application No. 61/457,455, filed on Apr. 1, 2011, provisional application No. 61/457,780, filed on Jun. 2, 2011, provisional application No. 61/193,329, filed on Nov. 18, 2008, provisional application No. 61/193,915, filed on Jan. 8, 2009, provisional application No. 61/202,181, filed on Feb. 4, 2009, provisional application No. 61/202,451, filed on Mar. 2, 2009, provisional application No. 61/213,216, filed on May 18, 2009, provisional application No. 61/213,534, filed on Jun. 17, 2009, provisional application No. 61/272,210, filed on Sep. 1, 2009, provisional application No. 61/272,356, filed on Sep. 16, 2009, provisional application No. 61/457,951, filed on Jul. 15, 2011.

(56) References Cited

U.S. PATENT DOCUMENTS

| | | | |
|---|---|---|---|
| 4,016,871 | A | 4/1977 | Schiff |
| 4,031,884 | A | 6/1977 | Henzel |
| 4,245,647 | A | 1/1981 | Randall |
| 4,270,143 | A | 5/1981 | Morris |
| 4,316,218 | A | 2/1982 | Gay |
| 4,382,184 | A | 5/1983 | Wernikoff |
| 4,545,390 | A | 10/1985 | Leary |
| 4,709,385 | A | 11/1987 | Pfeiler |
| 4,712,560 | A | 12/1987 | Schaefer et al. |
| 4,723,938 | A | 2/1988 | Goodin et al. |
| 4,741,328 | A | 5/1988 | Gabbay |
| 4,758,223 | A | 7/1988 | Rydell |
| 4,849,906 | A | 7/1989 | Chodos et al. |
| 4,865,043 | A | 9/1989 | Shimoni |
| 4,878,115 | A | 10/1989 | Elion |
| 4,920,413 | A | 4/1990 | Nakamura |
| 4,991,589 | A | 2/1991 | Hongo et al. |
| 4,994,965 | A | 2/1991 | Crawford et al. |
| 5,020,516 | A | 6/1991 | Biondi |
| 5,054,045 | A | 10/1991 | Whiting et al. |
| 5,054,492 | A | 10/1991 | Scribner |
| 5,056,524 | A | 10/1991 | Oe |
| 5,062,056 | A | 10/1991 | Lo et al. |
| 5,176,619 | A | 1/1993 | Segalowitz |
| 5,177,796 | A | 1/1993 | Feig et al. |
| 5,293,574 | A | 3/1994 | Roehm et al. |
| 5,295,486 | A | 3/1994 | Wollschlager et al. |
| 5,330,496 | A | 7/1994 | Alferness |
| 5,357,550 | A | 10/1994 | Asahina et al. |
| 5,429,144 | A | 7/1995 | Wilk |
| 5,457,728 | A | 10/1995 | Whiting et al. |
| 5,457,754 | A | 10/1995 | Han et al. |
| 5,486,192 | A | 1/1996 | Walinsky et al. |
| 5,537,490 | A | 7/1996 | Yukawa |
| 5,538,494 | A | 7/1996 | Matsuda |
| 5,577,502 | A | 11/1996 | Darrow et al. |
| 5,586,201 | A | 12/1996 | Whiting et al. |
| 5,596,990 | A | 1/1997 | Yock |
| 5,613,492 | A | 3/1997 | Feinberg |
| 5,619,995 | A | 4/1997 | Lobodzinski |
| 5,630,414 | A | 5/1997 | Horbaschek |
| 5,674,217 | A | 10/1997 | Wahlstrom et al. |
| 5,724,977 | A | 3/1998 | Yock |
| 5,764,723 | A | 6/1998 | Weinberger |
| 5,766,208 | A | 6/1998 | McEwan |
| 5,792,157 | A | 8/1998 | Mische et al. |
| 5,809,105 | A | 9/1998 | Roehm et al. |
| 5,822,391 | A | 10/1998 | Whiting et al. |
| 5,830,222 | A | 11/1998 | Makower |
| 5,879,305 | A | 3/1999 | Yock |
| 5,885,218 | A | 3/1999 | Teo |
| 5,885,244 | A | 3/1999 | Leone et al. |
| 5,916,194 | A | 6/1999 | Jacobsen et al. |
| 5,921,934 | A | 7/1999 | Teo |
| 5,971,976 | A | 10/1999 | Wang et al. |
| 6,088,488 | A | 7/2000 | Hardy et al. |
| 6,095,976 | A | 8/2000 | Nachtomy |
| 6,120,455 | A | 9/2000 | Teo |
| 6,126,608 | A | 10/2000 | Kemme et al. |
| 6,148,095 | A | 11/2000 | Prause et al. |
| 6,152,878 | A | 11/2000 | Nachtomy |
| 6,195,445 | B1 | 2/2001 | Dubuisson-Jolly et al. |
| 6,233,478 | B1 | 5/2001 | Liu |
| 6,246,898 | B1 | 6/2001 | Vesely et al. |
| 6,254,541 | B1 | 7/2001 | Teo |
| 6,267,727 | B1 | 7/2001 | Teo |
| 6,278,767 | B1 | 8/2001 | Hsieh |
| 6,331,181 | B1 | 12/2001 | Tierney et al. |
| 6,370,417 | B1 | 4/2002 | Horbaschek et al. |
| 6,377,011 | B1 | 4/2002 | Ben-Ur |
| 6,442,415 | B1 | 8/2002 | Bis et al. |
| 6,454,715 | B2 | 9/2002 | Teo |
| 6,454,776 | B1 | 9/2002 | Tajima et al. |
| 6,473,635 | B1 | 10/2002 | Rasche |
| 6,491,636 | B2 | 12/2002 | Chenal |
| 6,493,575 | B1 | 12/2002 | Kesten et al. |
| 6,496,716 | B1 | 12/2002 | Langer et al. |
| 6,532,380 | B1 | 3/2003 | Close et al. |
| 6,538,634 | B1 | 3/2003 | Chui et al. |
| 6,546,271 | B1 | 4/2003 | Reisfeld |
| 6,576,007 | B2 | 6/2003 | Dehdashtian et al. |
| 6,589,176 | B2 | 7/2003 | Jago |
| 6,616,596 | B1 | 9/2003 | Milbocker |
| 6,643,533 | B2 | 11/2003 | Knoplioch |
| 6,659,953 | B1 | 12/2003 | Sumanaweera et al. |
| 6,666,863 | B2 | 12/2003 | Wentzel et al. |
| 6,704,593 | B2 | 3/2004 | Stainsby |
| 6,708,052 | B1 | 3/2004 | Mao et al. |
| 6,711,436 | B1 | 3/2004 | Duhaylongsod |
| 6,718,055 | B1 | 4/2004 | Suri |
| 6,726,675 | B1 | 4/2004 | Beyar |
| 6,728,566 | B1 | 4/2004 | Subramanyan |
| 6,731,973 | B2 | 5/2004 | Voith |
| 6,786,896 | B1 | 9/2004 | Madhani et al. |
| 6,788,827 | B1 | 9/2004 | Makram-Ebeid |
| 6,796,972 | B1 | 9/2004 | Sinofsky et al. |
| 6,835,177 | B2 | 12/2004 | Fritz et al. |
| 6,858,003 | B2 | 2/2005 | Evans et al. |
| 6,912,471 | B2 | 6/2005 | Heigl |
| 6,937,696 | B1 | 8/2005 | Mostafavi |
| 6,959,266 | B1 | 10/2005 | Mostafavi |
| 6,973,202 | B2 | 12/2005 | Mostafavi |
| 6,980,675 | B2 | 12/2005 | Evron et al. |
| 6,996,430 | B1 | 2/2006 | Gilboa et al. |
| 6,999,852 | B2 | 2/2006 | Green |
| 7,031,504 | B1 | 4/2006 | Argiro et al. |
| 7,070,555 | B2 | 7/2006 | Siess |
| 7,085,342 | B2 | 8/2006 | Younis et al. |
| 7,134,994 | B2 | 11/2006 | Alpert |
| 7,155,046 | B2 | 12/2006 | Aben et al. |
| 7,155,315 | B2 | 12/2006 | Niemeyer et al. |
| 7,180,976 | B2 | 2/2007 | Wink et al. |
| 7,191,100 | B2 | 3/2007 | Mostafavi |
| 7,209,779 | B2 | 4/2007 | Kaufman |
| 7,215,802 | B2 | 5/2007 | Klingensmith |
| 7,221,973 | B2 | 5/2007 | Nitz |
| 7,269,457 | B2 | 9/2007 | Shafer |
| 7,289,652 | B2 | 10/2007 | Florent et al. |

(56) References Cited

U.S. PATENT DOCUMENTS

| | | |
|---|---|---|
| 7,321,677 B2 | 1/2008 | Evron et al. |
| 7,339,585 B2 | 3/2008 | Verstraelen et al. |
| 7,343,032 B2 | 3/2008 | Oakley et al. |
| 7,343,195 B2 | 3/2008 | Strommer et al. |
| 7,359,554 B2 | 4/2008 | Klingensmith |
| 7,369,691 B2 | 5/2008 | Kondo et al. |
| 7,397,935 B2 | 7/2008 | Kimmel |
| 7,398,116 B2 | 7/2008 | Edwards |
| 7,517,318 B2 | 4/2009 | Altmann |
| 7,546,154 B2 | 6/2009 | Hornegger et al. |
| 7,587,074 B2 | 9/2009 | Zarkh et al. |
| 7,599,730 B2 | 10/2009 | Hunter |
| 7,604,601 B2 | 10/2009 | Altmann |
| 7,653,426 B2 | 1/2010 | Yatsuo et al. |
| 7,668,362 B2 | 2/2010 | Olson et al. |
| 7,693,349 B2 | 4/2010 | Gering |
| 7,697,974 B2 | 4/2010 | Jenkins |
| 7,713,210 B2 | 5/2010 | Byrd |
| 7,729,743 B2 | 6/2010 | Sabczynski et al. |
| 7,729,746 B2 | 6/2010 | Redel et al. |
| 7,740,584 B2 | 6/2010 | Donaldson |
| 7,773,787 B2 | 8/2010 | Tek et al. |
| 7,773,792 B2 | 8/2010 | Kimmel |
| 7,778,488 B2 | 8/2010 | Nord |
| 7,778,688 B2 | 8/2010 | Strommer |
| 7,822,291 B2 | 10/2010 | Guetter |
| 7,831,076 B2 | 11/2010 | Altmann |
| 7,848,553 B2 | 12/2010 | Hertel |
| 7,877,132 B2 | 1/2011 | Rongen |
| 7,889,905 B2 | 2/2011 | Higgins et al. |
| 7,916,912 B2 | 3/2011 | Abramov et al. |
| 7,925,064 B2 | 4/2011 | Cloutier et al. |
| 7,925,069 B2 | 4/2011 | Ortyn et al. |
| 7,925,327 B2 | 4/2011 | Weese |
| 7,927,275 B2 | 4/2011 | Kuban |
| 7,930,014 B2 | 4/2011 | Huennekens et al. |
| 7,935,055 B2 | 5/2011 | Burckhardt |
| 7,961,926 B2 | 6/2011 | Viswanathan |
| 7,965,905 B2 | 6/2011 | Allon et al. |
| 7,970,187 B2 | 6/2011 | Puts |
| 7,978,916 B2 | 7/2011 | Klingensmith |
| 7,992,100 B2 | 8/2011 | Lundstrom |
| 8,029,447 B2 | 10/2011 | Kanz |
| 8,052,605 B2 | 11/2011 | Muller |
| 8,055,327 B2 | 11/2011 | Strommer et al. |
| 8,077,939 B2 | 12/2011 | Le Bezet et al. |
| 8,080,474 B2 | 12/2011 | Chen |
| 8,086,000 B2 | 12/2011 | Weijers |
| 8,155,411 B2 | 4/2012 | Hof |
| 8,157,742 B2 | 4/2012 | Taylor |
| 8,165,361 B2 | 4/2012 | Li |
| 8,172,763 B2 | 5/2012 | Nelson |
| 8,189,886 B2 | 5/2012 | Huo et al. |
| 8,199,981 B2 | 6/2012 | Koptenko et al. |
| 8,200,040 B2 | 6/2012 | Pfister |
| 8,213,676 B2 | 7/2012 | Bendall |
| 8,233,718 B2 | 7/2012 | Klingensmith |
| 8,271,068 B2 | 9/2012 | Khamene |
| 8,275,201 B2 | 9/2012 | Rangawala et al. |
| 8,289,284 B2 | 10/2012 | Glynn |
| 8,298,147 B2 | 10/2012 | Huennekens |
| 8,303,503 B2 | 11/2012 | Nair |
| 8,364,242 B2 | 1/2013 | Li |
| 8,396,276 B2 | 3/2013 | Gatta |
| 8,409,098 B2 | 4/2013 | Olson |
| 8,428,318 B2 | 4/2013 | Zhuo |
| 8,428,691 B2 | 4/2013 | Byrd |
| 8,433,115 B2 | 4/2013 | Chen |
| 8,457,374 B2 | 6/2013 | Lendl |
| 8,478,387 B2 | 7/2013 | Xu |
| 8,483,488 B2 | 7/2013 | Richter |
| 8,565,859 B2 | 10/2013 | Wang et al. |
| 2001/0031919 A1 | 10/2001 | Strommer et al. |
| 2002/0049375 A1* | 4/2002 | Strommer et al. ............ 600/407 |
| 2002/0058869 A1 | 5/2002 | Axelsson et al. |
| 2002/0090119 A1 | 7/2002 | Saito et al. |
| 2002/0114497 A1 | 8/2002 | Wetzel et al. |
| 2002/0188307 A1 | 12/2002 | Pintor et al. |
| 2003/0014100 A1 | 1/2003 | Meens et al. |
| 2003/0018251 A1 | 1/2003 | Solomon |
| 2003/0023141 A1 | 1/2003 | Stelzer et al. |
| 2003/0069499 A1 | 4/2003 | Lienard et al. |
| 2003/0088179 A1 | 5/2003 | Seeley et al. |
| 2003/0139772 A1 | 7/2003 | Fisher et al. |
| 2003/0157073 A1 | 8/2003 | Peritt |
| 2004/0034380 A1 | 2/2004 | Woolfson et al. |
| 2004/0077941 A1 | 4/2004 | Reddy et al. |
| 2004/0097805 A1 | 5/2004 | Verard et al. |
| 2004/0176681 A1 | 9/2004 | Mao et al. |
| 2004/0249270 A1 | 12/2004 | Kondo et al. |
| 2004/0254570 A1 | 12/2004 | Hadjicostis et al. |
| 2004/0267113 A1 | 12/2004 | Thomson |
| 2005/0004503 A1 | 1/2005 | Samson et al. |
| 2005/0008210 A1 | 1/2005 | Evron et al. |
| 2005/0031176 A1 | 2/2005 | Hertel |
| 2005/0033199 A1 | 2/2005 | van der Steen |
| 2005/0043614 A1 | 2/2005 | Huizenga et al. |
| 2005/0054916 A1 | 3/2005 | Mostafavi |
| 2005/0080336 A1 | 4/2005 | Byrd et al. |
| 2005/0090737 A1 | 4/2005 | Burrel et al. |
| 2005/0096589 A1 | 5/2005 | Shachar |
| 2005/0107688 A1 | 5/2005 | Strommer |
| 2005/0107808 A1 | 5/2005 | Evans et al. |
| 2005/0111719 A1 | 5/2005 | Pesatore et al. |
| 2005/0113685 A1 | 5/2005 | Maschke et al. |
| 2005/0137661 A1 | 6/2005 | Sra |
| 2005/0143777 A1 | 6/2005 | Sra |
| 2005/0154281 A1 | 7/2005 | Xue et al. |
| 2005/0197557 A1 | 9/2005 | Strommer et al. |
| 2005/0197559 A1 | 9/2005 | Boese et al. |
| 2005/0197566 A1 | 9/2005 | Strommer et al. |
| 2005/0201510 A1 | 9/2005 | Mostafavi |
| 2005/0228359 A1 | 10/2005 | Doyle |
| 2005/0234331 A1 | 10/2005 | Sendai |
| 2005/0273050 A1 | 12/2005 | Yokoyama et al. |
| 2005/0288577 A1 | 12/2005 | Weese |
| 2006/0058647 A1 | 3/2006 | Strommer et al. |
| 2006/0074285 A1 | 4/2006 | Zarkh et al. |
| 2006/0106318 A1 | 5/2006 | Davidson |
| 2006/0120581 A1 | 6/2006 | Eck et al. |
| 2006/0129142 A1 | 6/2006 | Reynolds |
| 2006/0147897 A1 | 7/2006 | Grinvald |
| 2006/0149134 A1 | 7/2006 | Soper et al. |
| 2006/0159318 A1 | 7/2006 | Alyassin et al. |
| 2006/0165270 A1 | 7/2006 | Borgert et al. |
| 2006/0173287 A1 | 8/2006 | Sabszynski et al. |
| 2006/0184016 A1 | 8/2006 | Glossop |
| 2006/0193505 A1 | 8/2006 | Glukhovsky et al. |
| 2006/0224188 A1 | 10/2006 | Libbus et al. |
| 2006/0241445 A1 | 10/2006 | Altmann |
| 2006/0241465 A1 | 10/2006 | Huennekens et al. |
| 2006/0241478 A1 | 10/2006 | Lewis |
| 2006/0253024 A1 | 11/2006 | Altmann |
| 2006/0253029 A1 | 11/2006 | Altmann |
| 2006/0253031 A1 | 11/2006 | Altmann |
| 2006/0257006 A1 | 11/2006 | Bredno et al. |
| 2006/0259137 A1 | 11/2006 | Artof et al. |
| 2006/0269108 A1 | 11/2006 | Viswanathan |
| 2006/0287595 A1 | 12/2006 | Maschke |
| 2007/0038061 A1 | 2/2007 | Huennekens et al. |
| 2007/0038081 A1* | 2/2007 | Eck et al. ............ 600/437 |
| 2007/0043292 A1 | 2/2007 | Camus |
| 2007/0053558 A1 | 3/2007 | Puts et al. |
| 2007/0055128 A1 | 3/2007 | Glossop |
| 2007/0060798 A1 | 3/2007 | Krupnik et al. |
| 2007/0088431 A1 | 4/2007 | Bourang et al. |
| 2007/0106146 A1 | 5/2007 | Altmann et al. |
| 2007/0116342 A1 | 5/2007 | Zarkh et al. |
| 2007/0123771 A1 | 5/2007 | Redel et al. |
| 2007/0142907 A1 | 6/2007 | Moaddeb et al. |
| 2007/0173861 A1 | 7/2007 | Strommer |
| 2007/0208388 A1 | 9/2007 | Jahns |
| 2007/0219630 A1 | 9/2007 | Chu |
| 2007/0232896 A1 | 10/2007 | Gilboa et al. |

(56) References Cited

U.S. PATENT DOCUMENTS

| | | |
|---|---|---|
| 2007/0248253 A1 | 10/2007 | Manzke et al. |
| 2007/0255139 A1 | 11/2007 | Deschinger |
| 2007/0276216 A1 | 11/2007 | Beyar et al. |
| 2008/0008366 A1 | 1/2008 | Desh |
| 2008/0015677 A1 | 1/2008 | Glossop et al. |
| 2008/0021331 A1 | 1/2008 | Grinvald |
| 2008/0082049 A1 | 4/2008 | Evans et al. |
| 2008/0089566 A1 | 4/2008 | Node-Langlois |
| 2008/0114238 A1 | 5/2008 | Lloyd |
| 2008/0119922 A1 | 5/2008 | Alkhatib |
| 2008/0137935 A1 | 6/2008 | Spahn |
| 2008/0146923 A1 | 6/2008 | Mejia |
| 2008/0146942 A1 | 6/2008 | Dala-Krishna |
| 2008/0177183 A1 | 7/2008 | Courtney |
| 2008/0188739 A1 | 8/2008 | Rongen et al. |
| 2008/0221439 A1 | 9/2008 | Iddan et al. |
| 2008/0221440 A1 | 9/2008 | Iddan et al. |
| 2008/0221442 A1 | 9/2008 | Tolkowsky et al. |
| 2008/0253686 A1 | 10/2008 | Bayer |
| 2008/0267475 A1 | 10/2008 | Lendl |
| 2008/0283771 A1 | 11/2008 | Li |
| 2008/0300487 A1 | 12/2008 | Govari |
| 2009/0016587 A1 | 1/2009 | Strobel et al. |
| 2009/0074284 A1 | 3/2009 | Zeineh et al. |
| 2009/0093676 A1 | 4/2009 | Davidson |
| 2009/0103682 A1 | 4/2009 | Chen et al. |
| 2009/0105579 A1 | 4/2009 | Garibaldi |
| 2009/0171201 A1 | 7/2009 | Olson |
| 2009/0177444 A1 | 7/2009 | Wiemker et al. |
| 2009/0257631 A1 | 10/2009 | Baumgart |
| 2009/0264753 A1 | 10/2009 | Von Schulthes |
| 2009/0275831 A1 | 11/2009 | Hall |
| 2009/0281418 A1 | 11/2009 | Ruijters et al. |
| 2009/0299195 A1 | 12/2009 | Muller et al. |
| 2009/0306547 A1 | 12/2009 | Iddan et al. |
| 2010/0041949 A1 | 2/2010 | Tolkowsky |
| 2010/0049034 A1 | 2/2010 | Eck et al. |
| 2010/0054573 A1 | 3/2010 | Shekhara |
| 2010/0067768 A1 | 3/2010 | Ionasec et al. |
| 2010/0094124 A1 | 4/2010 | Schoonenberg et al. |
| 2010/0094127 A1 | 4/2010 | Xu |
| 2010/0099979 A1 | 4/2010 | Schoonenberg et al. |
| 2010/0111396 A1 | 5/2010 | Boucheron |
| 2010/0114289 A1 | 5/2010 | Camus |
| 2010/0123715 A1 | 5/2010 | Hansegard |
| 2010/0134517 A1 | 6/2010 | Saikaly et al. |
| 2010/0135546 A1 | 6/2010 | Cziria |
| 2010/0157041 A1 | 6/2010 | Klaiman et al. |
| 2010/0160764 A1 | 6/2010 | Steinberg et al. |
| 2010/0160773 A1 | 6/2010 | Cohen et al. |
| 2010/0161022 A1 | 6/2010 | Tolkowsky |
| 2010/0161023 A1 | 6/2010 | Cohen et al. |
| 2010/0171819 A1 | 7/2010 | Tolkowsky et al. |
| 2010/0172556 A1 | 7/2010 | Cohen et al. |
| 2010/0174192 A1 | 7/2010 | Azuma |
| 2010/0191102 A1 | 7/2010 | Steinberg et al. |
| 2010/0198063 A1 | 8/2010 | Huber |
| 2010/0220917 A1 | 9/2010 | Steinberg et al. |
| 2010/0222671 A1 | 9/2010 | Cohen et al. |
| 2010/0228076 A1 | 9/2010 | Blank et al. |
| 2010/0246910 A1 | 9/2010 | Wiemker |
| 2010/0290693 A1 | 11/2010 | Cohen et al. |
| 2010/0310140 A1 | 12/2010 | Schneider |
| 2010/0331670 A1 | 12/2010 | Strommer et al. |
| 2011/0015520 A1 | 1/2011 | Meetz et al. |
| 2011/0026786 A1 | 2/2011 | Mohamed |
| 2011/0033094 A1 | 2/2011 | Zarkh |
| 2011/0034801 A1 | 2/2011 | Baumgart |
| 2011/0052030 A1 | 3/2011 | Bruder et al. |
| 2011/0071404 A1 | 3/2011 | Schmidtt et al. |
| 2011/0075912 A1 | 3/2011 | Rieber et al. |
| 2011/0087104 A1 | 4/2011 | Moore |
| 2011/0118825 A1 | 5/2011 | Hunter et al. |
| 2011/0157154 A1 | 6/2011 | Bernard et al. |
| 2011/0228992 A1 | 9/2011 | Wels et al. |
| 2011/0230758 A1 | 9/2011 | Eichler |
| 2011/0293163 A1 | 12/2011 | Kargar et al. |
| 2011/0319752 A1 | 12/2011 | Steinberg et al. |
| 2012/0004529 A1 | 1/2012 | Tolkowsky et al. |
| 2012/0004533 A1 | 1/2012 | Peng |
| 2012/0004537 A1 | 1/2012 | Tolkowsky et al. |
| 2012/0014574 A1 | 1/2012 | Ferschel et al. |
| 2012/0029339 A1 | 2/2012 | Cohen et al. |
| 2012/0051606 A1 | 3/2012 | Saikia |
| 2012/0059220 A1 | 3/2012 | Holsing |
| 2012/0059253 A1 | 3/2012 | Wang et al. |
| 2012/0065507 A1 | 3/2012 | Brunke |
| 2012/0069167 A1 | 3/2012 | Liu et al. |
| 2012/0072190 A1 | 3/2012 | Sharma et al. |
| 2012/0083696 A1 | 4/2012 | Kitamura |
| 2012/0123238 A1 | 5/2012 | Vaillant et al. |
| 2012/0130242 A1 | 5/2012 | Burgess |
| 2012/0140998 A1 | 6/2012 | Zhu |
| 2012/0207367 A1 | 8/2012 | Kneepkens |
| 2012/0215093 A1 | 8/2012 | Ji |
| 2012/0224751 A1 | 9/2012 | Kemp |
| 2012/0230565 A1 | 9/2012 | Steinberg et al. |
| 2012/0245460 A1 | 9/2012 | Slomka |
| 2012/0294498 A1 | 11/2012 | Popovic |
| 2012/0310081 A1 | 12/2012 | Adler et al. |
| 2013/0004044 A1 | 1/2013 | Ross |
| 2013/0030295 A1 | 1/2013 | Huennekens |
| 2013/0046167 A1 | 2/2013 | Shah |
| 2013/0053664 A1 | 2/2013 | Jian et al. |
| 2013/0109958 A1 | 5/2013 | Baumgart |
| 2013/0109959 A1 | 5/2013 | Baumgart |
| 2013/0120296 A1 | 5/2013 | Merrit |
| 2013/0120297 A1 | 5/2013 | Merrit |
| 2013/0123616 A1 | 5/2013 | Merrit |
| 2013/0308844 A1 | 11/2013 | Florent et al. |
| 2013/0329030 A1 | 12/2013 | Tolkowsky et al. |
| 2013/0329977 A1 | 12/2013 | Tolkowsky et al. |
| 2014/0094660 A1 | 4/2014 | Tolkowsky et al. |
| 2014/0094689 A1 | 4/2014 | Cohen et al. |
| 2014/0094690 A1 | 4/2014 | Tolkowsky et al. |
| 2014/0094691 A1 | 4/2014 | Steinberg et al. |
| 2014/0094692 A1 | 4/2014 | Tolkowsky et al. |
| 2014/0094693 A1 | 4/2014 | Cohen et al. |
| 2014/0100451 A1 | 4/2014 | Tolkowsky et al. |
| 2014/0107479 A1 | 4/2014 | Kleiman et al. |
| 2014/0111541 A1 | 4/2014 | Tolkowsky et al. |
| 2014/0112566 A1 | 4/2014 | Steinberg et al. |
| 2014/0114184 A1 | 4/2014 | Klaiman et al. |
| 2014/0114185 A1 | 4/2014 | Tolkowsky et al. |
| 2014/0114308 A1 | 4/2014 | Tolkowsky et al. |
| 2014/0114333 A1 | 4/2014 | Tolkowsky et al. |
| 2014/0121513 A1 | 5/2014 | Tolkowsky et al. |

FOREIGN PATENT DOCUMENTS

| | | |
|---|---|---|
| WO | 99/07354 A2 | 2/1999 |
| WO | 00/33755 A1 | 6/2000 |
| WO | 01/10313 A1 | 2/2001 |
| WO | 01/43642 | 6/2001 |
| WO | 03/043516 A2 | 5/2003 |
| WO | 03/096894 | 11/2003 |
| WO | 2005/026891 | 3/2005 |
| WO | 2005/051452 A2 | 6/2005 |
| WO | 2005/124689 | 12/2005 |
| WO | 2006/027781 A2 | 3/2006 |
| WO | 2006/066122 | 6/2006 |
| WO | 2006/066124 | 6/2006 |
| WO | 2006/076409 A2 | 7/2006 |
| WO | 2006/114721 A2 | 11/2006 |
| WO | 2006/121984 | 11/2006 |
| WO | 2007/002685 A2 | 1/2007 |
| WO | 2007/014028 A1 | 2/2007 |
| WO | 2007/015199 A2 | 2/2007 |
| WO | 2008/007350 A1 | 1/2008 |
| WO | 2008/062358 A1 | 5/2008 |
| WO | 2008/107905 | 9/2008 |
| WO | 2009/153794 | 12/2009 |
| WO | 2010/058398 A2 | 5/2010 |
| WO | 2011/046903 A2 | 4/2011 |

(56) References Cited

FOREIGN PATENT DOCUMENTS

| WO | 2011/046904 A1 | 4/2011 |
|---|---|---|
| WO | 2011128797 A1 | 10/2011 |
| WO | 2011/145094 A2 | 11/2011 |
| WO | 2012/014212 A1 | 2/2012 |
| WO | 2012/028190 A1 | 3/2012 |
| WO | 2012095755 A1 | 7/2012 |
| WO | 2012107857 A1 | 8/2012 |
| WO | 2012/138872 A2 | 10/2012 |
| WO | 2012/138874 A2 | 10/2012 |
| WO | 2012/176191 A1 | 12/2012 |
| WO | 2013/025602 A1 | 2/2013 |
| WO | 2013061225 A1 | 5/2013 |
| WO | 2013/084345 A1 | 6/2013 |
| WO | 2013/169814 A1 | 11/2013 |
| WO | 2013/175472 A2 | 11/2013 |
| WO | 2014/002095 A2 | 1/2014 |

OTHER PUBLICATIONS

Timinger et al., entitled "Motion compensated coronary interventional navigation by means of diaphragm tracking and elastic motion models" (Phys Med Biol. Feb. 7, 2005;50(3):491-503.

Timinger et al., entitled "Motion compensation for interventional navigation on 3D static roadmaps based on an affine model and gating" (Phys Med Biol. Mar. 7, 2004;49(5):719-32.

Turski et al., entitled "Digital Subtraction Angiography 'Road Map'" (American Journal of Roentgenology, 1982.

Iddan et al., entitled "3D imaging in the studio and elsewhere" (SPIE Proceedings vol. 4298, 2001.

"Catheter Insertion Simulation with Combined Visual and Haptic Feedback," by Zorcolo et al. (Center for Advanced Studies, Research and Development in Sardinia).

"4D-CT imaging of a volume influenced by respiratory motion on multi-slice CT Tinsu Pan," by Lee et al., (Medical Physics, Feb. 2004, vol. 31, Issue 2, pp. 333-340)—an abstract.

"New 4-D imaging for real-time intraoperative MRI: adaptive 4-D scan," by Tokuda et al. (Med Image Comput Assist Intenv Int Conf. 2006;9(Pt 1):454-61) an abstract.

"Real-time interactive viewing of 4D kinematic MR joint studies," by Schulz et al. (Med Image Comput Assist Intenv Int Conf. 2005;8(Pt 1):467-73.)—an abstract.

"4D smoothing of gated SPECT images using a left-ventricle shape model and a deformable mesh," by Brankov et al., (Nuclear Science Symposium Conference Record, 2004 IEEE, Oct. 2004, vol. 5, 2845-2848).

"Prospective motion correction of X-ray images for coronary interventions," by Shechter et al. (IEEE Trans Med Imaging. Apr. 2005;24(4):441-50).

"Cardiac Imaging: We Got the Beat!" by Elizabeth Morgan (Medical Imaging, Mar. 2005).

"Noninvasive Coronary Angiography by Retrospectively ECG-Gated Multislice Spiral CT," by Achenbach et al., (Circulation. Dec. 5, 2000;102(23):2823-8).

"Spatially-adaptive temporal smoothing for reconstruction of dynamic and gated image sequences," by Brankov et al., (Nuclear Science Symposium Conference Record, 2000 IEEE, 2000, vol. 2, 15/146-15/150)—an abstract.

"Full-scale clinical implementation of a video based respiratory gating system," by Ramsey et al., (Engineering in Medicine and Biology Society, 2000. Proceedings of the 22nd Annual International Conference of the IEEE, 2000, vol. 3, 2141-2144)—an abstract.

"Three-Dimensional Respiratory-Gated MR Angiography of the Coronary Arteries: Comparison with Conventional Coronary Angiography," by Post et al., (AJR, 1996; 166: 1399-1404).

Soffie Mansson, et al., "Dosimetric verification of breathing adapted radiotherapy using polymer gel", Journal of Physics: Conference series 56 (200) 300-303.

"From 2D to 4D" AXIOM Innovations—Mar. 2008, www.siemens.com/healthcare-magazine.

A Brochure: Impella® 2.5, Percutaneous Circulatory Support System, ABIOMED™, 2007.

Frangi et al., entitled "Multiscale vessel enhancement filtering" (Medical Image Computing and Computer Assisted Intervention—MICCAI 1998—Lecture Notes in Computer Science, vol. 1496, Springer Verlag, Berlin, Germany, pp. 130-137).

Dijkstra, entitled "A Note on Two Problems in Connexion with Graphs" (Numerische Mathematik I, 269-271, 1959).

Zarkh et al., entitled "Guide wire navigation and therapeutic device localization for catheterization procedure" (International Congress Series 1281 (2005) 311-316.

Brochure: At the Transvascular Cardiovascular Therapeutics (TCT) conference held in Washington DC, USA in Oct. 2008, Paieon Inc. demonstrated the CardiOp-THV system for real-time navigation and positioning of a trans-catheter heart valve.

Brochure: At the TCT conference held in San Francisco, USA in Sep. 2009, Paieon Inc. demonstrated the IC-PRO Comprehensive Imaging Workstation for providing assistance in cardiac catheterization procedures.

An International Search Report dated Sep. 8, 2009, which issued during the prosecution of Applicant's PCT/IL09/00610.

An International Search Report dated Jan. 15, 2009, issued during the prosecution of Applicant's PCT Patent Application No. PCT/IL08/000316.

An International Search Report dated May 19, 2010 issued during the prosecution of Applicant's PCT Patent Application No. PCT/IL2009/001089.

"A new point matching algorithm for non-rigid registration," by Chui (Computer Vision and Image Understanding 89 (2003) 114-141).

"Advanced and Challenges in Super-Resolution," by Farsiu (International Journal of Imaging Systems and Technology, vol. 14, No. 2, pp. 47-57, Special issue on high-resolution image reconstruction, Aug. 2004).

"Image Registration by Minimization of Residual Complexity," by Myronenko (CVPR 2009).

"Image inpainting," by Bertalmio (ACM Siggraph 2000, New Orleans, Louisiana, USA, Jul. 2000).

"Nonrigid registration using free-form deformations: application to breast MR images," by Rueckert, (IEEE Trans. Med. Img, vol. 18, No. 8, 1999).

"Unwarping of unidirectionally distorted EPI images," by Kybic (IEEE Trans. Med. Img., vol. 19, No. 2, 2000).

"Geometrically Correct 3-D Reconstruction of Intravascular Ultrasound Images by Fusion with Biplane Angiography—Methods and Validation," Andreas Wahle, IEEE Transactions on Medical Imaging, Final Manuscript #187/98, Jun. 30, 1999.

An International Search Report dated Jan. 6, 2012, which issued during the prosecution of Applicant's PCT Application No. PCT/IL11/00391.

An Official Action dated Nov. 28, 2011, which issued during the prosecution of Applicant's U.S. Appl. No. 12/075,252.

An Official Action dated Dec. 8, 2011, which issued during the prosecution of Applicant's U.S. Appl. No. 12/075,244.

U.S. Appl. No. 60/845,347 to Strommer et al., filed Sep. 2006.

International Search Report dated Mar. 2, 2012, issued in PCT/IL11/00612.

Office Action dated Mar. 14, 2012, issued in U.S. Appl. No. 12/075,214.

Office Action dated Mar. 15, 2012, issued in U.S. Appl. No. 12/649,944.

Office Action dated Mar. 15, 2012, issued in U.S. Appl. No. 12/650,152.

Office Action dated May 22, 2012, issued in U.S. Appl. No. 12/075,244.

Umeda, H. et al., "Promising efficacy of primary gradual and prolonged balloon angioplasty in small coronary arteries: A randomized comparison with cutting balloon angioplasty and conventional balloon angioplasty", 2004.

W. Santamore et al., "A microcomputer based automated quantative coronary angiographic analysis system," Annals of Biomedical Engineering, vol. 16, pp. 367-377, 1988.

(56) References Cited

OTHER PUBLICATIONS

V. Duddalwar, "Multislice CT angiography: a practical guide to CT angiography in vascular imaging and intervention," The British Journal of Radiology, 77 (2004), S27-S38.
Official Action dated Oct. 23, 2012, which issued during the prosecution of JP Application No. 2009-552328.
Official Action dated Nov. 23, 2012, which issued during the prosecution of U.S. Appl. No. 12/649,944.
Official Action dated Aug. 27, 2012, which issued during the prosecution U.S. Appl. No. 12/075,214.
International Search Report dated Oct. 10, 2012, which issued during the prosecution of PCT/IL2012/000246.
Communication dated Sep. 5, 2012, which issued during the prosecution of EP Application 09 766 329.8-1526.
Communication dated Oct. 29, 2012, which issued during the prosecution of EP Application 08 719941.0-1265/2129284.
Computer translation of JP 2010-253017 to Takeshi.
G. Mancini et al., "Automated quantitative coronary arteriography: morphologic and physiologic validation in vivo of a rapid digital angiographic method," Circulation 1987;75:452-460.
I. Kompatsiaris et al., "Deformable Boundary Detection of Stents in Angiographic Images," IEEE Transactions on Medical Imaging, vol. 19, No. 6, Jun. 2000.
L. Yaneza et al., "Atherosclerotic Plaque Can Be Quantified Using Multifractal and Wavelet Decomposition Techniques," Abstracts—Angiography & Interventional Cardiology, JACC Mar. 3, 2004.
Official Action dated Oct. 31, 2012, which issued during the prosecution U.S. Appl. No. 12/075,244.
Official Action dated Sep. 20, 2012, which issued during the prosecution of U.S. Appl. No. 12/649,955.
U.S. Appl. No. 61/359,431.
W. Goodman et al., "Coronary-Artery Calcification in Young Adults With End-Stage Renal Disease Who Are Undergoing Dialysis," The New England Journal of Medicine, vol. 342 No. 20.
W. Leung et al., "Coronary Artery Quantitation and Data Management System for Paired Cineangiograms," Catheterization and Cardiovascular Diagnosis 24:121-134 (1991).
A search report dated Nov. 23, 2012, which issued during the prosecution of Applicant's EP Application 09 827264.4-1265/2358269.
An examination report dated Dec. 5, 2012, which issued during the prosecution of Applicant's EP Application 09766329.8.
An Official Action dated Dec. 10, 2012, which issued during the prosecution of Applicant's U.S. Appl. No. 12/650,156.
An Official Action dated Dec. 11, 2012, which issued during the prosecution of Applicant's U.S. Appl. No. 12/650,152.
An Official Action dated Jan. 22, 2013, which issued during the prosecution of Applicant's U.S. Appl. No. 12/650,121.
An Official Action dated Jan. 28, 2013, which issued during the prosecution of Applicant's U.S. Appl. No. 12/781,366.
An Official Action dated Feb. 4, 2013, which issued during the prosecution of Applicant's U.S. Appl. No. 13/228,185.
Peng Wang et al.: "Image-Based Device Tracking for the Co-registration of Angiography and Intravascular Ultrasound Images", MICCAI 2011, Part I, LINCS 6891, pp. 161-168, 2011.
An Official Action dated Jul. 2, 2013, which issued during the prosecution of Applicant's U.S. Appl. No. 12/075,244.
An Official Action dated Jun. 19, 2013, which issued during the prosecution of Applicant's U.S. Appl. No. 12/075,214.
An Official Action dated May 31, 2013, which issued during the prosecution of Applicant's U.S. Appl. No. 12/075,252.
An Official Action dated May 6, 2013, which issued during the prosecution of Applicant's U.S. Appl. No. 12/487,315.
A Notice of Allowance dated Jun. 4, 2013, which issued in Applicant's U.S. Appl. No. 12/649,960.
An Official Action dated Sep. 6, 2013, which issued during the prosecution of Applicant's U.S. Appl. No. 12/650,605.
An Official Action dated Aug. 30, 2013, which issued during the prosecution of Applicant's U.S. Appl. No. 12/650,121.
An Official Action dated Sep. 12, 2013, which issued during the prosecution of Applicant's U.S. Appl. No. 12/781,260.
A Notice of Allowance in Applicant's U.S. Appl. No. 12/781,414.
An Official Action dated Aug. 3, 2012, which issued during the prosecution of Applicant's U.S. Appl. No. 12/781,294.
An Official Action dated Jun. 19, 2012, which issued during the prosecution of Applicant's U.S. Appl. No. 12/075,252.
An Official Action dated Jun. 18, 2012, which issued during the prosecution of Applicant's U.S. Appl. No. 12/781,366.
An Official Action dated Jun. 7, 2012, which issued during the prosecution of Applicant's U.S. Appl. No. 12/650,156.
An Official Action dated May 29, 2012, which issued during the prosecution of Applicant's U.S. Appl. No. 12/650,121.
Buddy D. Ratner, "Biomaterials Science: An Introduction to Materials in Medicine", Elsevier, chapter 7, 1996.
Gerald E. Miller, "Fundamentals of Biomedical Transport Processes, Morgan & Claypool Publishers", chapter 2, 2010.
Gerhard Albert ten Brinke, "Automated coronary flow reserve assessment using planar x-ray angiography", PhD dissertation, Universiteit Twente, 2011.
Jerry T. Wong et al., "Quantification of fractional flow reserve based on angiographic image data", Int J Cardiovasc Imaging 28:13-22, Jan. 7, 2011.
Kassab, G. S. et al., "Cross-sectional area and volume compliance of porcine left coronary arteries," Am. J. Physiol. Heart Circ. Physiol. 281, H623-H628, Aug. 2011.
Molloi S. et al., "Absolute volumetric coronary blood flow measurement with digital subtraction angiography". Int J Card Imaging 14:137-145, 1998.
Molloi, S. et al., "Estimation of coronary artery hyperemic blood flow based on arterial lumen volume using angiographic images," The International Journal of Cardiovascular Imaging, vol. 28, No. 1, 1-11, Jan. 7, 2011.
Molloi, S. et al., "Quantification of coronary artery lumen volume by digital angiography: in vivo validation," Circulation 104, 2351-2357, Nov. 6, 2001.
Molloi, S. et al., "Quantification of volumetric coronary blood flow with dual-energy digital subtraction angiography," Circulation 93, 1919-1927, May 15, 1996.
Molloi, S. et al., "Regional volumetric coronary blood flow measurement by digital angiography: in vivo validation," Acad. Radiol. 11, 7, 757-766, Jul. 2004.
Sian Sen et al., "Development and Validation of a New, Adenosine-Independent Index of Stenosis Severity From Coronary Wave—Intensity Analysis". Journal of the American College of Cardiology, vol. 59, Apr. 10, 2012.
Yunlong Huo et al., "A validated predictive model of coronary fractional flow reserve," J. R. Soc. Interface, Nov. 23, 2011.
A Notice of Allowance issued in Applicant's U.S. Appl. No. 13/965,893.
An Official Action dated Nov. 13, 2013, which issued during the prosecution of Applicant's U.S. Appl. No. 12/666,879.
An Official Action dated Oct. 2, 2013, which issued during the prosecution of Applicant's U.S. Appl. No. 13/228,211.
An Official Action dated Oct. 21, 2013, which issued during the prosecution of Applicant's U.S. Appl. No. 12/075,214.
An Official Action dated Oct. 23, 2013, which issued during the prosecution of Applicant's U.S. Appl. No. 12/648,913.
An Official Action dated Oct. 25, 2013, which issued during the prosecution of Applicant's U.S. Appl. No. 12/781,366.
An Official Action dated Oct. 3, 2013, which issued during the prosecution of Applicant's U.S. Appl. No. 13/228,185.
An Official Action dated Oct. 30, 2013, which issued during the prosecution of Applicant's U.S. Appl. No. 13/228,335.
An Official Action dated Oct. 4, 2013, which issued during the prosecution of Applicant's U.S. Appl. No. 12/649,955.
Correspondence from the International Searching Authority in Applicant's PCT/IL13/50549.
Correspondence from the International Searching Authority in Applicant's PCT/IL2013/050438.
International Search Report and Written Opinion for International Patent Application PCT/IL2013/050438 mailed Dec. 2, 2013.
Office Action, dated Jan. 7, 2014, issued by the United States Patent and Trademark Office, in counterpart U.S. Appl. No. 12/075,244.

(56) References Cited

OTHER PUBLICATIONS

Office Action, dated Feb. 12, 2014, issued by the United States Patent and Trademark Office, in counterpart U.S. Appl. No. 12/781,260.
Office Action, dated Dec. 31, 2013, issued by the United States Patent and Trademark Office, in counterpart U.S. Appl. No. 12/075,252.
Notice of Allowance, dated Jan. 3, 2014, issued by the United States Patent and Trademark Office, in counterpart U.S. Appl. No. 13/965,872.
Search Report, dated Jan. 22, 2014, issued by the International Searching Authority, in counterpart Application No. PCT/IL13/50549.
Written Opinion, dated Jan. 22, 2014, issued by the International Searching Authority, in counterpart Application No. PCT/IL13/50549.
An Official Action dated Feb. 20, 2014, which issued during the prosecution of Applicant's U.S. Appl. No. 12/075,214.
An Official Action dated May 6, 2014, which issued during the prosecution of Applicant's U.S. Appl. No. 12/075,252.
A Notice of Allowance issued in Applicant's U.S. Appl. No. 12/666,879.
An Official Action dated Mar. 21, 2014, which issued during the prosecution of Applicant's U.S. Appl. No. 12/648,913.
An Official Action dated Apr. 3, 2014, which issued during the prosecution of Applicant's U.S. Appl. No. 12/649,955.
An Official Action dated Mar. 14, 2014, which issued during the prosecution of Applicant's U.S. Appl. No. 12/650,605.
An Official Action dated Apr. 25, 2014, which issued during the prosecution of Applicant's U.S. Appl. No. 12/650,121.
An Official Action dated Apr. 24, 2014, which issued during the prosecution of Applicant's U.S. Appl. No. 12/781,366.
An Official Action dated Apr. 17, 2014, which issued during the prosecution of Applicant's U.S. Appl. No. 13/228,211.
An Official Action dated Apr. 28, 2014, which issued during the prosecution of Applicant's U.S. Appl. No. 13/228,185.
An Official Action dated May 5, 2014, which issued during the prosecution of Applicant's U.S. Appl. No. 14/096,968.
An Official Action dated Feb. 14, 2014, which issued during the prosecution of Applicant's U.S. Appl. No. 14/098,140.
Pyxaras et al., "Quantitative angiography optical coherence tomography for the functional assessment of nonobstructive coronary stenoses" (Medscape), Oct. 2013, 11 pages total.
Tu et al., "In vivo comparison of arterial lumen dimensions assessed by co-registered 3D quantitative coronary angiography intravascular ultrasound and optical coherence tomography.", Int J Cardiovasc Imaging (2012) 28:1315-1327, Jan. 20, 2012, DOI 10.1007/s10554-012-0016-6, 13 pages total.
Tu et al, "Fusion of 3D QCA and IVUS/OCT", Int J Cardiovasc Imaging (2011) 27:197-207, Jan. 25, 2011, DOI 10.1007/s10554-011-9809-2, 11 pages total.
An Official Action dated Jul. 3, 2014, which issued during the prosecution of Applicant's U.S. Appl. No. 12/648,913.
An Official Action dated Jul. 30, 2014, which issued during the prosecution of Applicant's U.S. Appl. No. 12/075,214.
An Official Action dated Jul. 31, 2014, which issued during the prosecution of Applicant's U.S. Appl. No. 12/649,944.
An Official Action dated Jun. 18, 2014, which issued during the prosecution of Applicant's U.S. Appl. No. 12/075,244.
An Official Action dated May 21, 2014, which issued during the prosecution of Applicant's U.S. Appl. No. 12/650,156.
An Official Action dated May 29, 2014, which issued during the prosecution of Applicant's U.S. Appl. No. 14/097,922.
An Official Action dated May 30, 2014, which issued during the prosecution of Applicant's U.S. Appl. No. 13/228,335.
An Official Action dated Jun. 3, 2014, which issued during the prosecution of Applicant's U.S. Appl. No. 12/781,260.

\* cited by examiner

DISPLAYING A DEVICE WITHIN AN ENDOLUMINAL IMAGE STACK

CROSS REFERENCES TO RELATED APPLICATIONS

The present application is a continuation of PCT Application no. PCT/IL2013/050438 to Steinberg (published as WO 13/175,472), filed May 21, 2013, which:

(i) claims the benefit of:
U.S. Provisional Patent Application 61/688,730, filed May 21, 2012; and
U.S. Provisional Patent Application 61/761,709, filed Feb. 7, 2013;
(ii) is a continuation-in-part of U.S. Ser. No. 13/228,229 to Tolkowsky (published as US 2012/0004537), filed Sep. 8, 2011, which is a continuation of International Application No. PCT/IL2011/000612 to Tolkowsky (published as WO 12/014,212), filed 28 Jul. 2011, which claims the benefit of:
U.S. Provisional Patent Application 61/344,464, filed 29 Jul. 2010;
U.S. Provisional Patent Application 61/344,875, filed 1 Nov. 2010;
U.S. Provisional Patent Application 61/457,339, filed 3 Mar. 2011;
U.S. Provisional Patent Application 61/457,455, filed 1 Apr. 2011;
U.S. Provisional Patent Application 61/457,780, filed 2 Jun. 2011; and
U.S. Provisional Patent Application 61/457,951, filed 15 Jul. 2011; and
(iii) is a continuation-in-part of U.S. patent application Ser. No. 12/666,879 to Steinberg (published as US 2012/0230565), which is the US national phase of PCT Application No. PCT/IL2009/001089 to Cohen (published as WO 10/058,398), filed Nov. 18, 2009, which claims the benefit of:
U.S. Provisional Patent Application 61/193,329, filed Nov. 18, 2008;
U.S. Provisional Patent Application 61/193,915, filed Jan. 8, 2009;
U.S. Provisional Patent Application 61/202,181, filed Feb. 4, 2009;
U.S. Provisional Patent Application 61/202,451, filed Mar. 2, 2009;
U.S. Provisional Patent Application 61/213,216, filed May 18, 2009;
U.S. Provisional Patent Application 61/213,534, filed Jun. 17, 2009;
U.S. Provisional Patent Application 61/272,210, filed Sep. 1, 2009; and
U.S. Provisional Patent Application 61/272,356, filed Sep. 16, 2009.

The present application is related to the following patent applications:
U.S. patent application Ser. No. 12/075,214 to Iddan (published as 2008/0221439), filed Mar. 10, 2008, entitled "Tools for use with moving organs."
U.S. patent application Ser. No. 12/075,252 to Iddan (published as US 2008/0221440), filed Mar. 10, 2008, entitled "Imaging and tools for use with moving organs."
U.S. patent application Ser. No. 12/075,244 to Tolkowsky (published as US 2008/0221442), filed Mar. 10, 2008, entitled "Imaging for use with moving organs."
U.S. patent application Ser. No. 12/781,260 to Blank (published as US 2010/0228076), filed May 17, 2010, entitled "Controlled actuation and deployment of a medical device."
U.S. patent application Ser. No. 12/487,315 to Iddan (published as US 2009/0306547), filed Jun. 18, 2009, entitled "Stepwise advancement of a medical tool," which claims the benefit of U.S. Provisional Patent Application No. 61/129,331 to Iddan, filed on Jun. 19, 2008, entitled "Stepwise advancement of a medical tool."

All of the above-mentioned applications are incorporated herein by reference.

FIELD OF EMBODIMENTS OF THE INVENTION

Some applications of the present invention generally relate to medical imaging. Specifically, some applications of the present invention relate to the co-use of endoluminal data and extraluminal imaging.

BACKGROUND

Vascular catheterizations, such as coronary catheterizations, are frequently-performed medical interventions. Such interventions are typically performed in order to diagnose the blood vessels for potential disease, and/or to treat diseased blood vessels. Typically, in order to enable observation of blood vessels, the catheterization is performed under extraluminal imaging. Additionally, for some procedures, an endoluminal data-acquisition device is used to perform endoluminal imaging and/or measurements. The extraluminal imaging and, where applicable, the endoluminal data are typically evaluated by the medical staff in combination with one another in the course of the intervention, as well as post procedurally.

SUMMARY OF EMBODIMENTS

Some applications of the present invention are applied to medical procedures performed, in whole or in part, on or within luminal structures. For some applications, apparatus and methods are provided for facilitating the co-use of extraluminal imaging and endoluminal data (i.e., data that are acquired using an endoluminal data-acquisition device), in performing medical procedures. Endoluminal data may include imaging data (e.g., imaging data acquired using an endoluminal imaging probe), data derived from measurements (e.g., measurements performed using an endoluminal sensor or measuring device), other data, and any combination thereof.

There is therefore provided, in accordance with some applications of the present invention, apparatus for use with an endoluminal device configured to be moved through a lumen of a subject's body, one or more extraluminal imaging devices configured to acquire extraluminal images of the lumen, and a display, the apparatus including:

at least one processor configured to receive from the one or more extraluminal imaging devices:
  a first set of extraluminal images of the lumen, the lumen being visible in at least some of the first set of images, and
  a second set of extraluminal images of the endoluminal device inside the lumen, the second set of extraluminal images being acquired while the endoluminal device is being moved through the lumen; the at least one processor including:
  roadmap-image-designation functionality configured to designate at least one of the first set of images as a roadmap image;

pathway-designation functionality configured to designate, within the lumen in the roadmap image, a roadmap pathway;

feature-identifying functionality configured for at least a portion of the images belonging to the second set of extraluminal images to identify within the image a plurality of the features that are visible within the image;

roadmap-mapping functionality configured for the at least a portion of the images belonging to the second set of extraluminal images:
to compare an arrangement of three or more of the features within the image to a shape of at least a portion of the roadmap pathway, and
based upon the comparing, to map the identified features to locations along the roadmap pathway within the roadmap image; and output-generation functionality configured, in response to the mapping of the identified features to locations along the roadmap pathway within the roadmap image, to generate an output on the display.

For some applications, the roadmap-mapping functionality is configured to compare the arrangement of three or more features within the image to the shape of the portion of the roadmap pathway by comparing vectors defined by pairs of the features within the image to vectors defined by pairs of locations on the roadmap pathway.

For some applications, the roadmap-mapping functionality is configured to compare the arrangement of three or more features within the image to the shape of the portion of the roadmap pathway by comparing an angle defined by vectors defined by pairs of the features within the image to an angle defined by the roadmap pathway.

For some applications, the roadmap-mapping functionality is configured to compare the arrangement of three or more features within the image to the shape of the portion of the roadmap pathway by comparing distances between by pairs of the features within the image to the shape of at least the portion of the roadmap pathway.

For some applications, the at least one processor further includes pathway-calibration functionality configured, based upon the mapping, to determine a plurality of local calibration factors associated with respective portions of the roadmap image.

For some applications,
the endoluminal device includes a first endoluminal data-acquisition device configured to acquire a plurality of endoluminal data points while the endoluminal data-acquisition device is being moved through the lumen from a starting location within the lumen,
the at least one processor further includes co-registration functionality configured to co-register respective endoluminal data points to respective locations within the roadmap image, by:
identifying the starting location of the endoluminal data-acquisition device in the roadmap image, and
determining a distance from the starting location at which respective endoluminal data points were acquired, based upon the speed at which the endoluminal data-acquisition device was moved through the lumen, the frame rate at which the endoluminal data points were acquired, and the local calibration factor associated with the respective portions of the roadmap image; and
the output-generation functionality is configured to generate an output on the display based upon the co-registration of the endoluminal data points to the respective locations within the roadmap image.

For some applications,
the apparatus is for use with a second endoluminal data-acquisition device configured to acquire an additional plurality of endoluminal data points while the second endoluminal data-acquisition device is being moved through the lumen, and
the co-registration functionality is configured to co-register respective endoluminal data points of the additional plurality of endoluminal data points acquired by the second endoluminal data-acquisition device to respective endoluminal data points of the plurality of endoluminal data points acquired by the first endoluminal data-acquisition device by co-registering the additional plurality of endoluminal data points acquired by the second endoluminal data-acquisition device to respective locations within the roadmap image.

For some applications, the endoluminal data-acquisition device includes an endoluminal optical coherence tomography device configured to acquire optical coherence tomography images, and the co-registration functionality is configured to co-register respective endoluminal data points to respective locations within the roadmap image by co-registering respective optical coherence tomography images to respective locations within the roadmap image.

For some applications, the at least one processor is configured, based upon the mapping, to determine locations of the endoluminal device in respective extraluminal images of the second set of extraluminal images with respect to the roadmap image.

For some applications, the at least one processor is configured, on-line with respect to acquisitions of the extraluminal images of the second set of extraluminal images, to determine locations of the endoluminal device in respective extraluminal images of the second set of extraluminal images with respect to the roadmap image, and the output-generation functionality is configured to generate an output that is indicative of the determined on-line location of the endoluminal device with respect to the roadmap image.

For some applications,
the endoluminal device includes a first endoluminal data-acquisition device configured to acquire a plurality of endoluminal data points while the endoluminal data-acquisition device is being moved through the lumen,
the at least one processor further includes co-registration functionality that is configured, based upon determining locations of the endoluminal device in respective extraluminal images of the second set of extraluminal images with respect to the roadmap image, to co-register respective endoluminal data points to respective locations within the roadmap image, and
the output-generation functionality is configured to generate an output on the display based upon the co-registration of the endoluminal data points to the respective locations within the roadmap image.

For some applications,
the apparatus is for use with a second endoluminal data-acquisition device configured to acquire an additional plurality of endoluminal data points while the second endoluminal data-acquisition device is being moved through the lumen, and
the co-registration functionality is configured to co-register respective endoluminal data points of the additional plurality of endoluminal data points acquired by the second endoluminal data-acquisition device to respective endoluminal data points of the plurality of endoluminal data points acquired by the first endoluminal data-acquisition device by co-registering the additional plurality of endoluminal data points acquired by the second endoluminal data-acquisition device to respective locations within the roadmap image.

For some applications, the endoluminal data-acquisition device includes an endoluminal imaging device that is configured to acquire a plurality of endoluminal images while the endoluminal imaging device is being moved through the lumen, and the co-registration functionality is configured to co-register respective endoluminal data points to respective locations within the roadmap image by co-registering respective endoluminal images to respective locations within the roadmap image.

For some applications, the endoluminal data-acquisition device includes an endoluminal data-acquisition device that is configured to acquire functional data regarding the lumen while the endoluminal data-acquisition device is being moved through the lumen, and the co-registration functionality is configured to co-register respective endoluminal data points to respective locations within the roadmap image by co-registering respective functional endoluminal data points to respective locations within the roadmap image.

For some applications, the at least one processor further includes stack-generation functionality that is configured, based upon the co-registration, to generate a stack of endoluminal data points, in which relative dispositions of endoluminal data points within the stack correspond to relative locations of the endoluminal data points with respect to the roadmap image.

For some applications,
the at least one processor further includes parameter-measurement functionality that is configured, based upon the co-registering of the endoluminal data points to respective locations within the roadmap image, to determine a parameter of a portion of the lumen that corresponds to a portion of the stack of endoluminal data points, and
the output-generation functionality is configured to generate the output in response to the determined parameter.

For some applications, the parameter-measurement functionality is configured to determine a length of a portion of the lumen that corresponds to a portion of the stack of endoluminal data points.

There is further provided, in accordance with some applications of the present invention, a method for use with an endoluminal device configured to be moved through a lumen of a subject's body, an extraluminal imaging device configured to acquire extraluminal images of the lumen, and a display, the method including:
using the extraluminal imaging device, acquiring a first set of extraluminal images of the lumen, the lumen being visible in at least some of the first set of images;
designating at least one of the first set of images as a roadmap image;
designating, within the lumen in the roadmap image, a roadmap pathway;
moving the endoluminal device through at least a portion of the lumen;
while the endoluminal device is being moved through the lumen, acquiring a second set of extraluminal images of the endoluminal device inside the lumen, using the extraluminal imaging device;
for at least a portion of the images belonging to the second set of extraluminal images:
identifying within the image a plurality of the features that are visible within the image;
comparing an arrangement of three or more of the features within the image to a shape of at least a portion of the roadmap pathway; and
based upon the comparing, mapping the identified features to locations along the roadmap pathway within the roadmap image; and in response thereto, generating an output on the display.

There is further provided, in accordance with some applications of the present invention, apparatus for use with an endoluminal device configured to be moved through a lumen of a subject's body, one or more extraluminal imaging devices configured to acquire extraluminal images of the lumen, and a display, the apparatus including:
at least one processor configured to receive from the one or more extraluminal imaging devices:
a first set of extraluminal images of the lumen, the lumen being visible in at least some of the first set of images, and
a second set of extraluminal images of the endoluminal device inside the lumen, the second set of extraluminal images being acquired while the endoluminal device is being moved through the lumen; the at least one processor including:
roadmap-image-designation functionality configured to designate at least one of the first set of images as a roadmap image;
feature-identifying functionality configured for at least a portion of the images belonging to the second set of extraluminal images to identify within the image a plurality of the features that are visible within the image;
pathway-calibration functionality configured, in response to the identified features in the images belonging to the second set of extraluminal images, to determine a plurality of local calibration factors associated with respective portions of the roadmap image; and
output-generation functionality configured, based upon one or more of the determined local calibration factors, to generate an output on the display.

For some applications, the pathway-calibration functionality is configured to determine the plurality of local calibration factors associated with respective portions of the roadmap image based upon a known speed at which the endoluminal device is moved through the lumen.

For some applications, the pathway-calibration functionality is configured to determine the plurality of local calibration factors associated with respective portions of the roadmap image by determining local relative calibration factors of the portions of the roadmap image with respect to each other.

For some applications, the pathway-calibration functionality is configured to determine the plurality of local calibration factors associated with respective portions of the roadmap image based upon a known physical dimension associated with one or more of the identified features.

For some applications, the pathway-calibration functionality is configured to determine the plurality of local calibration factors associated with respective portions of the roadmap image based upon a known physical distance between two or more of the identified features.

For some applications, the pathway-calibration functionality is configured to determine the plurality of local calibration factors associated with respective portions of the roadmap image based upon a known physical dimension of one or more of the identified features.

For some applications,
the at least one processor further includes:
pathway-designation functionality configured to designate, within the lumen in the roadmap image, a roadmap pathway; and roadmap-mapping functionality configured for the at least a portion of the images belonging to the second set of extraluminal images:
to compare an arrangement of three or more of the features within the image to a shape of at least a portion of the roadmap pathway, and
based upon the comparing, to map the identified features to locations along the roadmap pathway within the roadmap image; and
the pathway-calibration functionality is configured to determine the plurality of local calibration factors associated with respective portions of the roadmap image based upon the mapping.

For some applications, the pathway-calibration functionality is configured to determine the plurality of local calibration factors associated with respective portions of the roadmap image by determining a plurality of local calibration factors associated with respective portions of the roadmap pathway.

For some applications,
the endoluminal device includes a first endoluminal data-acquisition device configured to acquire a plurality of endoluminal data points while the endoluminal data-acquisition device is being moved through the lumen from a starting location within the lumen; and
the at least one processor further includes co-registration functionality configured to co-register respective endoluminal data points to respective locations within the roadmap image, by:
identifying the starting location of the endoluminal data-acquisition device in the roadmap image; and
determining a distance from the starting location at which respective endoluminal data points were acquired, based upon the speed at which the endoluminal data-acquisition device was moved through the lumen, the frame rate at which the endoluminal data points were acquired, and the local calibration factor associated with the respective portions of the roadmap image; and
the output-generation functionality is configured to generate an output on the display based upon the co-registration of the endoluminal data points to the respective locations within the roadmap image.

For some applications,
the apparatus is for use with a second endoluminal data-acquisition device configured to acquire an additional plurality of endoluminal data points while the second endoluminal data-acquisition device is being moved through the lumen, and
the co-registration functionality is configured to co-register respective endoluminal data points of the additional plurality of endoluminal data points acquired by the second endoluminal data-acquisition device to respective endoluminal data points of the plurality of endoluminal data points acquired by the first endoluminal data-acquisition device by co-registering the additional plurality of endoluminal data points acquired by the second endoluminal data-acquisition device to respective locations within the roadmap image.

For some applications, the endoluminal data-acquisition device includes an endoluminal optical coherence tomography device configured to acquire optical coherence tomography images, and the co-registration functionality is configured to co-register respective endoluminal data points to respective locations within the roadmap image by co-registering respective optical coherence tomography images to respective locations within the roadmap image.

For some applications, the at least one processor is configured, based upon the local calibration factors, to determine locations of the endoluminal device in respective extraluminal images of the second set of extraluminal images with respect to the roadmap image.

For some applications, the at least one processor is configured, on-line with respect to acquisitions of the extraluminal images of the second set of extraluminal images, to determine locations of the endoluminal device in respective extraluminal images of the second set of extraluminal images with respect to the roadmap image, and the output-generation functionality is configured to generate an output that is indicative of the determined on-line location of the endoluminal device with respect to the roadmap image.

For some applications,
the endoluminal device includes a first endoluminal data-acquisition device configured to acquire a plurality of endoluminal data points while the endoluminal data-acquisition device is being moved through the lumen,
the at least one processor further includes co-registration functionality that is configured, based upon determining locations of the endoluminal device in respective extraluminal images of the second set of extraluminal images with respect to the roadmap image, to co-register respective endoluminal data points to respective locations within the roadmap image, and
the output-generation functionality is configured to generate an output on the display based upon the co-registration of the endoluminal data points to the respective locations within the roadmap image.

For some applications,
the apparatus is for use with a second endoluminal data-acquisition device configured to acquire an additional plurality of endoluminal data points while the second endoluminal data-acquisition device is being moved through the lumen, and
the co-registration functionality is configured to co-register respective endoluminal data points of the additional plurality of endoluminal data points acquired by the second endoluminal data-acquisition device to respective endoluminal data points of the plurality of endoluminal data points acquired by the first endoluminal data-acquisition device by co-registering the additional plurality of endoluminal data points acquired by the second endoluminal data-acquisition device to respective locations within the roadmap image.

For some applications, the endoluminal data-acquisition device includes an endoluminal imaging device that is configured to acquire a plurality of endoluminal images while the endoluminal imaging device is being moved through the lumen, and the co-registration functionality is configured to co-register respective endoluminal data points to respective locations within the roadmap image by co-registering respective endoluminal images to respective locations within the roadmap image.

For some applications, the endoluminal data-acquisition device includes an endoluminal data-acquisition device that is configured to acquire functional data regarding the lumen while the endoluminal data-acquisition device is being moved through the lumen, and the co-registration functionality is configured to co-register respective endoluminal data points to respective locations within the roadmap image by co-registering respective functional endoluminal data points to respective locations within the roadmap image.

For some applications, the at least one processor further includes stack-generation functionality that is configured, based upon the co-registration, to generate a stack of endoluminal data points, in which relative dispositions of endoluminal data points within the stack correspond to relative locations of the endoluminal data points with respect to the roadmap image.

For some applications,
the at least one processor further includes parameter-measurement functionality that is configured, based upon the co-registering of the endoluminal data points to respective locations within the roadmap image, to determine a parameter of a portion of the lumen that corresponds to a portion of the stack of endoluminal data points, and the output-generation functionality is configured to generate the output in response to the determined parameter.

For some applications, the parameter-measurement functionality is configured to determine a length of a portion of the lumen that corresponds to a portion of the stack of endoluminal data points.

There is further provided, in accordance with some applications of the present invention, a method for use with an endoluminal device configured to be moved through a lumen of a subject's body, an extraluminal imaging device configured to acquire extraluminal images of the lumen, and a display, the method including:

using the extraluminal imaging device, acquiring a first set of extraluminal images of the lumen, the lumen being visible in at least some of the first set of images;

designating at least one of the first set of images as a roadmap image;

moving the endoluminal device through the lumen;

while the endoluminal device is being moved through the lumen, acquiring a second set of extraluminal images of the endoluminal device inside the lumen, using the extraluminal imaging device;

identifying, within each of at least a portion of the images belonging to the second set of extraluminal images, a plurality of features that are visible in the image;

in response to the identified features in the images belonging to the second set of extraluminal images, determining a plurality of local calibration factors associated with respective portions of the roadmap image; and generating an output on the display, based upon one or more of the determined local calibration factors.

There is further provided, in accordance with some applications of the present invention, apparatus for use with an endoluminal device the endoluminal device having at least one radiopaque portion associated therewith and being configured to be moved through a lumen of a subject, one or more extraluminal imaging devices configured to acquire extraluminal images of the lumen, and a display, the apparatus including:

a reference tool, the reference tool having coupled thereto radiopaque markers, a characteristic of the markers varying along a least a portion of the reference tool, the reference tool being configured to be inserted into the lumen; and at least one processor configured:
while the endoluminal device is being moved through the lumen, to operate the extraluminal imaging device to acquire a plurality of extraluminal images of the lumen; and
to determine that, at times corresponding to the acquisitions of respective extraluminal images of the lumen, the endoluminal device was at respective locations within the lumen, by determining, within the extraluminal images of the lumen, locations of the at least one radiopaque portion associated with the endoluminal device with respect to the radiopaque markers of the reference tool;

the processor including output-generation functionality configured to generate an output on the display in response to the determined locations of the endoluminal device within the lumen.

For some applications, the at least one processor is configured, on-line with respect to acquisitions of the extraluminal images of the lumen, to determine locations of the endoluminal device with respect to the lumen, the output-generation functionality being configured to generate the output by generating an output that is indicative of the determined on-line location of the endoluminal device with respect to the lumen.

For some applications, a distance between pairs of markers that are coupled to the reference tool varies along at least the portion of the reference tool.

For some applications, a shape of the markers that are coupled to the reference tool varies along at least the portion of the reference tool.

For some applications, a pattern of the markers that are coupled to the reference tool varies along at least the portion of the reference tool.

For some applications, the reference tool includes a guide tool configured to guide the movement of the endoluminal device within the lumen.

For some applications, the guide tool includes a tool selected from the group consisting of: a sheath, and a wire.

For some applications,
the endoluminal device includes a first endoluminal data-acquisition device configured to acquire a plurality of endoluminal data points while the endoluminal data-acquisition device is being moved through the lumen, the at least one processor includes co-registration functionality configures, based on determining that at times corresponding to the acquisitions of respective extraluminal images of the lumen the endoluminal device was at respective locations within the lumen, to co-register respective endoluminal data points to respective locations along the lumen, and the output-generation functionality is configured to generate the output by generating an output on the display based upon the co-registration of the endoluminal data points to the respective locations along the lumen.

For some applications,
the apparatus is for use with a second endoluminal data-acquisition device configured to acquire an additional plurality of endoluminal data points while the second endoluminal data-acquisition device is being moved through the lumen, and the co-registration functionality is configured to co-register respective endoluminal data points of the additional plurality of endoluminal data points acquired by the second endoluminal data-acquisition device to respective endoluminal data points of the plurality of endoluminal data points acquired by the first endoluminal data-acquisition device by co-registering the additional plurality of endoluminal data points acquired by the second endoluminal data-acquisition device to respective locations along the lumen.

For some applications, the endoluminal data-acquisition device includes an endoluminal imaging device that is configured to acquire a plurality of endoluminal images while the endoluminal imaging device is being moved through the lumen, and the co-registration functionality is configured to co-register respective endoluminal data points to respective locations along the lumen by co-registering respective endoluminal images to respective locations along the lumen.

For some applications, the endoluminal data-acquisition device includes an endoluminal data-acquisition device that is configured to acquire functional data regarding the lumen while the endoluminal data-acquisition device is being moved through the lumen, and the co-registration functionality is configured to co-register respective endoluminal data points to respective locations along the lumen by co-registering respective functional endoluminal data points to respective locations along the lumen.

For some applications, the at least one processor further includes stack-generation functionality that is configured, based upon the co-registration, to generate a stack of endoluminal data points, in which relative dispositions of endoluminal data points within the stack correspond to relative locations of the endoluminal data points with respect to the lumen.

For some applications,
the at least one processor further includes parameter-measurement functionality that is configured, based upon the co-registering of the endoluminal data points to respective locations along the lumen, to determine a parameter of a portion of the lumen that corresponds to a portion of the stack of endoluminal data points, and
the output-generation functionality is configured to generate the output in response to the determined parameter.

For some applications, the parameter-measurement functionality is configured to determine a length of a portion of the lumen that corresponds to a portion of the stack of endoluminal data points.

There is further provided, in accordance with some applications of the present invention, a method for use with an endoluminal device the endoluminal device being configured to be moved through a lumen of a subject and having at least one radiopaque portion associated therewith, an extraluminal imaging device configured to acquire extraluminal images of the lumen, and a display, the method including:
providing a reference tool, the reference tool having coupled thereto radiopaque markers, a characteristic of the markers varying along a least a portion of the reference tool;
inserting the reference tool into the lumen;
moving the endoluminal device through the lumen;
while the endoluminal device is being moved through the lumen, operating the extraluminal imaging device to acquire a plurality of extraluminal images of the lumen;
operating at least one processor to determine that, at times corresponding to the acquisitions of respective extraluminal images of the lumen, the endoluminal device was at respective locations within the lumen, by determining, within the extraluminal images of the lumen, locations of the at least one radiopaque portion associated with the endoluminal device with respect to the radiopaque markers of the reference tool; and
operating the processor to generate an output on the display in response thereto.

There is further provided, in accordance with some applications of the present invention, apparatus for use with an endoluminal data-acquisition device configured to acquire a plurality of endoluminal data points while moving through a lumen of a subject, and a display, the apparatus including:
at least one processor configured to determine that, at at least one location, an event occurred, the event being selected from the group consisting of: two or more endoluminal data points having been acquired, and no endoluminal data point having been acquired;
the at least one processor including:
stack-generation functionality configured to generate a stack of the endoluminal data points, in which the endoluminal data points are positioned at locations corresponding to relative locations within the lumen at which the endoluminal data points were acquired, and in which the event is accounted for; and
display-driving functionality configured to drive the display to display the stack.

For some applications, the display-driving functionality is configured to drive the display to display a length scale in relation to the displayed stack of the endoluminal data points.

For some applications, the endoluminal data-acquisition device includes an endoluminal imaging device that is configured to acquire a plurality of endoluminal images while the endoluminal imaging device is being moved through the lumen, and the stack-generation functionality is configured to generate the stack by generating an endoluminal image stack.

For some applications, the endoluminal data-acquisition device includes an endoluminal data-acquisition device that is configured to acquire functional data regarding the lumen while the endoluminal data-acquisition device is being moved through the lumen, and the stack-generation functionality is configured to generate the stack by generating a stack of functional endoluminal data points.

For some applications, the stack-generation functionality is configured to generate the stack of endoluminal data points by generating a stack of indications of the endoluminal data points, locations of the indications within the stack corresponding to relative locations within the lumen at which the endoluminal data points were acquired.

For some applications, the at least one processor is configured to determine that at the at least one location the event occurred by determining that at the at least one location two or more endoluminal data points were acquired.

For some applications, the stack-generation functionality is configured to account for the event by including in the stack only one of the endoluminal data points that was acquired at the location.

For some applications, the at least one processor is configured to determine that at the at least one location the event occurred by determining that at the at least one location no endoluminal data point was acquired.

For some applications, the stack-generation functionality is configured to account for the event by including in the stack a gap at a location within the stack that corresponds to the location within the lumen at which no endoluminal data point was acquired.

For some applications, the at least one processor further includes parameter-measurement functionality configured to measure a parameter of a portion of the lumen, based upon the stack of the endoluminal data points.

For some applications, the parameter-measurement functionality is configured to measure a length of the portion of the lumen, based upon the stack of the endoluminal data points.

There is further provided, in accordance with some applications of the present invention, a method for use with an endoluminal data-acquisition device configured to acquire endoluminal data points while moving through a lumen of a subject, including:
while the endoluminal data-acquisition device is being moved through the lumen, acquiring a plurality of endoluminal data points of the lumen using the endoluminal data-acquisition device;
determining that, at at least one location, an event occurred, the event being selected from the group consisting of: two or more endoluminal data points having been acquired, and no endoluminal data point having been acquired; and
displaying the endoluminal data points in a stack, in which the endoluminal data points are positioned at locations corresponding to relative locations within the lumen at which the endoluminal data points were acquired, and in which the event is accounted for.

There is further provided, in accordance with some applications of the present invention, apparatus for use with an endoluminal data-acquisition device configured to acquire a plurality of endoluminal data points while moving through a lumen of a subject, and a display, the apparatus including:

at least one processor configured to determine that, at at least one location, an event occurred, the event being selected from the group consisting of: two or more endoluminal data points having been acquired, and no endoluminal data point having been acquired;

the at least one processor including:
stack-generation functionality configured to generate a stack of the endoluminal data points, in which the endoluminal data points are positioned at locations corresponding to relative locations within the lumen at which the endoluminal data points were acquired, and in which the event is accounted for;
parameter-measurement functionality configured to measure a parameter of a portion of the lumen, based upon the stack of the endoluminal data points; and
output-generation functionality configured to generate an output on the display based upon the measured length.

For some applications, the endoluminal data-acquisition device includes an endoluminal imaging device that is configured to acquire a plurality of endoluminal images while the endoluminal imaging device is being moved through the lumen, and the stack-generation functionality is configured to generate the stack by generating an endoluminal image stack.

For some applications, the endoluminal data-acquisition device includes an endoluminal data-acquisition device that is configured to acquire functional data regarding the lumen while the endoluminal data-acquisition device is being moved through the lumen, and the stack-generation functionality is configured to generate the stack by generating a stack of functional endoluminal data points.

For some applications, the stack-generation functionality is configured to generate the stack of endoluminal data points by displaying a stack of indications of the endoluminal data points, locations of the indications within the stack corresponding to relative locations within the lumen at which the endoluminal data points were acquired.

For some applications, the at least one processor is configured to determine that at the at least one location the event occurred by determining that at the at least one location two or more endoluminal data points were acquired.

For some applications, the stack-generation functionality is configured to account for the event by including in the stack only one of the endoluminal data points that was acquired at the location.

For some applications, the at least one processor is configured to determine that at the at least one location the event occurred by determining that at the at least one location no endoluminal data point was acquired.

For some applications, the stack-generation functionality is configured to account for the event by including in the stack a gap at a location within the stack that corresponds to the location within the lumen at which no endoluminal data point was acquired.

For some applications, the parameter-measurement functionality is configured to measure a length of the portion of the lumen, based upon the stack of the endoluminal data points.

For some applications, the output-generation functionality is configured to drive the display to display the stack of endoluminal data points and to display a length scale in relation to the displayed stack of the endoluminal data points.

There is further provided, in accordance with some applications of the present invention, a method for use with an endoluminal data-acquisition device configured to acquire endoluminal data points while moving through a lumen of a subject, including:

while the endoluminal data-acquisition device is being moved through the lumen, acquiring a plurality of endoluminal data points of the lumen using the endoluminal data-acquisition device;

determining that, at at least one location, an event occurred, the event being selected from the group consisting of: two or more endoluminal data points having been acquired, and no endoluminal data point having been acquired;

displaying the endoluminal data points in a stack, in which the endoluminal data points are positioned at locations corresponding to relative locations within the lumen at which the endoluminal data points were acquired, and in which the event is accounted for; and determining a parameter of a portion of the lumen based upon the displayed stack of endoluminal data points.

There is further provided, in accordance with some applications of the present invention, apparatus for use with an endoluminal data-acquisition device configured to acquire a plurality of endoluminal data points while moving through a lumen of a subject, and a display, the apparatus including:

at least one processor including:
stack-generation functionality configured to generate a stack of the endoluminal data points;
co-registration functionality configured to co-register the endoluminal data points to respective locations along the lumen in an extraluminal image of the lumen;
parameter-measurement functionality configured, based upon the co-registering of the endoluminal data points to respective locations along the lumen in the extraluminal image of the lumen, to determine a parameter of a portion of the lumen that corresponds to a portion of the stack of endoluminal data points; and
output-generation functionality configured to generate an output on the display, in response to the measured parameter.

For some applications, the endoluminal data-acquisition device includes an endoluminal imaging device that is configured to acquire a plurality of endoluminal images while the endoluminal imaging device is being moved through the lumen, and the stack-generation functionality is configured to generate the stack by generating an endoluminal image stack.

For some applications, the endoluminal data-acquisition device includes an endoluminal data-acquisition device that is configured to acquire functional data regarding the lumen while the endoluminal data-acquisition device is being moved through the lumen, and the stack-generation functionality is configured to generate the stack by generating a stack of functional endoluminal data points.

For some applications, the stack-generation functionality is configured to generate the stack of endoluminal data points by displaying a stack of indications of the endoluminal data points, locations of the indications within the stack corresponding to relative locations within the lumen at which the endoluminal data points were acquired.

For some applications, the stack-generation functionality is configured to include in the stack a gap at a location within the stack that corresponds to a location within the lumen at which no endoluminal data point was acquired.

For some applications, the stack-generation functionality is configured to not include within the stack at least one endoluminal data point that was acquired at a location along the lumen at which another endoluminal data point was acquired.

For some applications, the parameter-measurement functionality is configured to determine the parameter of the portion of the lumen that corresponds to the portion of the stack of endoluminal data points by determining a length of the portion of the lumen that corresponds to the portion of the stack.

For some applications, the output-generation functionality is configured to drive the display to display the stack of endoluminal data points and to display a length scale in relation to the displayed stack of the endoluminal data points.

There is further provided, in accordance with some applications of the present invention, a method for use with an endoluminal data-acquisition device configured to acquire endoluminal data points while moving through a lumen of a subject, including:

while the endoluminal data-acquisition device is being moved through the lumen, acquiring a plurality of endoluminal data points of the lumen using the endoluminal data-acquisition device;

displaying the endoluminal data points in a stack;

co-registering the endoluminal data points to respective locations along the lumen in an extraluminal image of the lumen;

based upon the co-registering of the endoluminal data points to respective locations along the lumen in the extraluminal image of the lumen, determining a parameter of a portion of the lumen that corresponds to a portion of the stack of endoluminal data points; and generating an output in response thereto.

There is further provided, in accordance with some applications of the present invention, apparatus for use with an endoluminal data-acquisition device configured to acquire a plurality of endoluminal data points while moving through a lumen of a subject, and a display, the apparatus including:

at least one processor configured to determine that, at at least one location, no endoluminal data point was acquired;

the at least one processor including output-generation functionality configured to generate an output on the display using at least a portion of the plurality of endoluminal data points of the lumen acquired using the endoluminal data-acquisition device, the output including an indication that no endoluminal data point was acquired at the location.

For some applications, the endoluminal data-acquisition device includes an endoluminal imaging device that is configured to acquire a plurality of endoluminal images while the endoluminal imaging device is being moved through the lumen, and the output-generation functionality is configured to generate the output using a plurality of acquired endoluminal images of the lumen.

For some applications, the endoluminal data-acquisition device includes an endoluminal data-acquisition device that is configured to acquire functional data regarding the lumen, while the endoluminal data-acquisition device is being moved through the lumen, and the output-generation functionality is configured to generate the output using a plurality of acquired functional endoluminal data points regarding the lumen.

For some applications, the at least one processor includes stack-generation functionality configured to generate a stack of the endoluminal data points, in which the endoluminal data points are positioned at locations corresponding to relative locations within the lumen at which the endoluminal data points were acquired, the stack including a gap in the stack at a location within the stack that corresponds to the location within the lumen at which no endoluminal data point was acquired; and the output-generation functionality is configured to generate the output by driving the display to display the stack of endoluminal data points.

For some applications, the at least one processor further includes parameter-measurement functionality configured to measure a length of a portion of the lumen, based upon the stack of the endoluminal data points.

For some applications, the output-generation functionality is configured to drive the display to display a length scale in relation to the displayed stack of the endoluminal data points.

There is further provided, in accordance with some applications of the present invention, a method for use with an endoluminal data-acquisition device configured to acquire endoluminal data points while moving through a lumen of a subject's body, including:

while the endoluminal data-acquisition device is being moved through the lumen, acquiring a plurality of endoluminal data points of the lumen using the endoluminal data-acquisition device;

determining that, at at least one location, no endoluminal data point was acquired;

generating an output using at least a portion of the plurality of endoluminal data points of the lumen acquired using the endoluminal data-acquisition device, the output including an indication that no endoluminal data point was acquired at the location.

There is further provided, in accordance with some applications of the present invention, apparatus for use with an endoluminal data-acquisition device configured to acquire a plurality of endoluminal data points while moving through a lumen of a subject's body, and a display, the apparatus including:

at least one processor including:

stack-generation functionality configured to:

determine that the endoluminal data points are not aligned with each other due to non-longitudinal motion undergone by the endoluminal data-acquisition device with respect to the lumen, between acquisitions of respective endoluminal data points; and in response thereto, align the endoluminal data points with each other, to at least partially account for the non-longitudinal motion undergone by the endoluminal data-acquisition device; and output generation functionality configured to generate an output on the display based upon the aligned endoluminal data points.

For some applications, the stack-generation functionality is configured to determine that the endoluminal data points are not aligned with each other by determining that the endoluminal data points are not aligned with each other due to a portion of the endoluminal data-acquisition device having rotated about a longitudinal axis of the endoluminal data-acquisition device, between acquisitions of respective endoluminal data points.

For some applications, the stack-generation functionality is configured to determine that the endoluminal data points are not aligned with each other by determining that the endoluminal data points are not aligned with each other due to a portion of the endoluminal data-acquisition device having become tilted, between acquisitions of respective endoluminal data points.

For some applications, the stack-generation functionality is configured to determine that the endoluminal data points are not aligned with each other by determining that the endoluminal data points are not aligned with each other due to a portion of the endoluminal data-acquisition device having moved axially, between acquisitions of respective endoluminal data points.

For some applications, the apparatus further includes a sensor coupled to a portion of the data-acquisition device and configured to detect a non-longitudinal orientation of the portion of the data-acquisition device, and the stack-generation functionality is configured to determine that the endoluminal data points are not aligned with each other by detecting the non-longitudinal orientation of the portion of the data-acquisition device via the sensor.

For some applications, the stack-generation functionality is configured to align the endoluminal data points with each other by aligning the endoluminal data points with each other using image processing.

For some applications, the endoluminal data points include endoluminal images, and the stack-generation functionality is configured to align the endoluminal data points with each other by:

identifying a region of one of the endoluminal images as having a given characteristic;

identifying a region in an adjacent endoluminal image that has the same characteristic; and aligning the adjacent images with one another by aligning the regions of each of the images.

For some applications, the at least one processor is further configured to receive a plurality of extraluminal images of the lumen while the endoluminal data-acquisition device is being moved through the lumen, the endoluminal data-acquisition device includes at least a portion thereof that is visible in the extraluminal images, and the stack-generation functionality is configured to determine that the endoluminal data points are not aligned with each other, by determining a disposition of the endoluminal data-acquisition device with respect to the lumen at times at which respective extraluminal images were acquired, by performing image processing on the extraluminal images.

For some applications, the visible portion of the endoluminal data-acquisition device includes a portion that is asymmetric with respect to a longitudinal axis of the endoluminal data-acquisition device, and the stack-generation functionality is configured to determine the disposition of the endoluminal data-acquisition device with respect to the lumen at times at which respective extraluminal images were acquired by analyzing an appearance of the asymmetric portion in the respective extraluminal images.

For some applications, the stack-generation functionality is configured to align the endoluminal data points with each other by determining a centerline of the lumen and aligning the endoluminal data points with respect to the centerline.

For some applications, the stack-generation functionality is configured to determine the centerline of the lumen by determining a straightened centerline of the lumen, and the stack-generation functionality is configured to align the endoluminal data points with respect to the centerline by aligning the endoluminal data points with respect to the straightened centerline.

For some applications, the stack-generation functionality is configured to generate a stack of the endoluminal data points, based upon the alignment of the endoluminal data points, and the output generation functionality is configured to generate the output on the display by generating a display of the stack of endoluminal data points on the display.

For some applications, the endoluminal data-acquisition device includes an endoluminal imaging device that is configured to acquire a plurality of endoluminal images while the endoluminal imaging device is being moved through the lumen, and the stack-generation functionality is configured to generate the stack by generating an endoluminal image stack.

For some applications, the endoluminal data-acquisition device includes an endoluminal data-acquisition device that is configured to acquire functional data regarding the lumen while the endoluminal data-acquisition device is being moved through the lumen, and the stack-generation functionality is configured to generate the stack by generating a stack of functional endoluminal data points.

For some applications, the stack-generation functionality is configured to generate the stack by generating a stack of indications of the endoluminal data points, locations of the indications within the stack corresponding to relative locations within the lumen at which the endoluminal data points were acquired.

There is further provided, in accordance with some applications of the present invention, a method for use with an endoluminal data-acquisition device configured to acquire endoluminal data points while moving through a lumen of a subject's body, and a display, the method including:

while the endoluminal data-acquisition device is being moved through the lumen, acquiring a plurality of endoluminal data points of the lumen using the endoluminal data-acquisition device;

determining that the endoluminal data points are not aligned with each other due to non-longitudinal motion undergone by the endoluminal data-acquisition device with respect to the lumen, between acquisitions of respective endoluminal data points;

in response thereto, aligning the endoluminal data points with each other, to at least partially account for the non-longitudinal motion undergone by the endoluminal data-acquisition device; and generating an output on the display based upon the aligned endoluminal data points.

There is further provided, in accordance with some applications of the present invention, apparatus for use with an endoluminal data-acquisition device configured to acquire a plurality of endoluminal data points while moving through a lumen of a subject's body, a second endoluminal device configured to be moved through the lumen, and a display, the apparatus including:

at least one processor configured to:

determine that respective endoluminal data points correspond to respective locations along the lumen, and to determine a current location of the second endoluminal device with respect to the lumen;

the at least one processor including:

stack-generation functionality configured to generate a stack of the endoluminal data points, in which the endoluminal data points are positioned at locations corresponding to relative locations within the lumen at which the endoluminal data points were acquired; and display-driving functionality configured to drive the display to display the stack, and to display within the stack an image of the second endoluminal device at a location within the stack corresponding to the current location of the second endoluminal device.

For some applications, the display-driving functionality is configured to drive the display to display the image of the second endoluminal device within the stack by driving the display to display a virtual representation of the second endoluminal device within the stack.

For some applications, the display-driving functionality is configured to drive the display to display the image of the second endoluminal device within the stack by driving the display to display a real image of the second endoluminal device within the stack.

There is further provided, in accordance with some applications of the present invention, a method for use with an endoluminal data-acquisition device configured to acquire endoluminal data points while moving through a lumen of a subject's body, and a display, the method including:

while the endoluminal data-acquisition device is being moved through the lumen, acquiring a plurality of endoluminal data points of the lumen using the endoluminal data-acquisition device;

determining that respective endoluminal data points correspond to respective locations along the lumen;

driving the display to display at least some of the plurality of endoluminal data points in a stack;

while a second endoluminal device is inside the lumen, determining a current location of at least a portion of the second endoluminal device with respect to the lumen; and in response thereto, displaying within the stack an image of the second endoluminal device at a location within the stack corresponding to the current location of the second endoluminal device.

The present invention will be more fully understood from the following detailed description of embodiments thereof, taken together with the drawings, in which:

DETAILED DESCRIPTION OF EMBODIMENTS

Figure 1A:
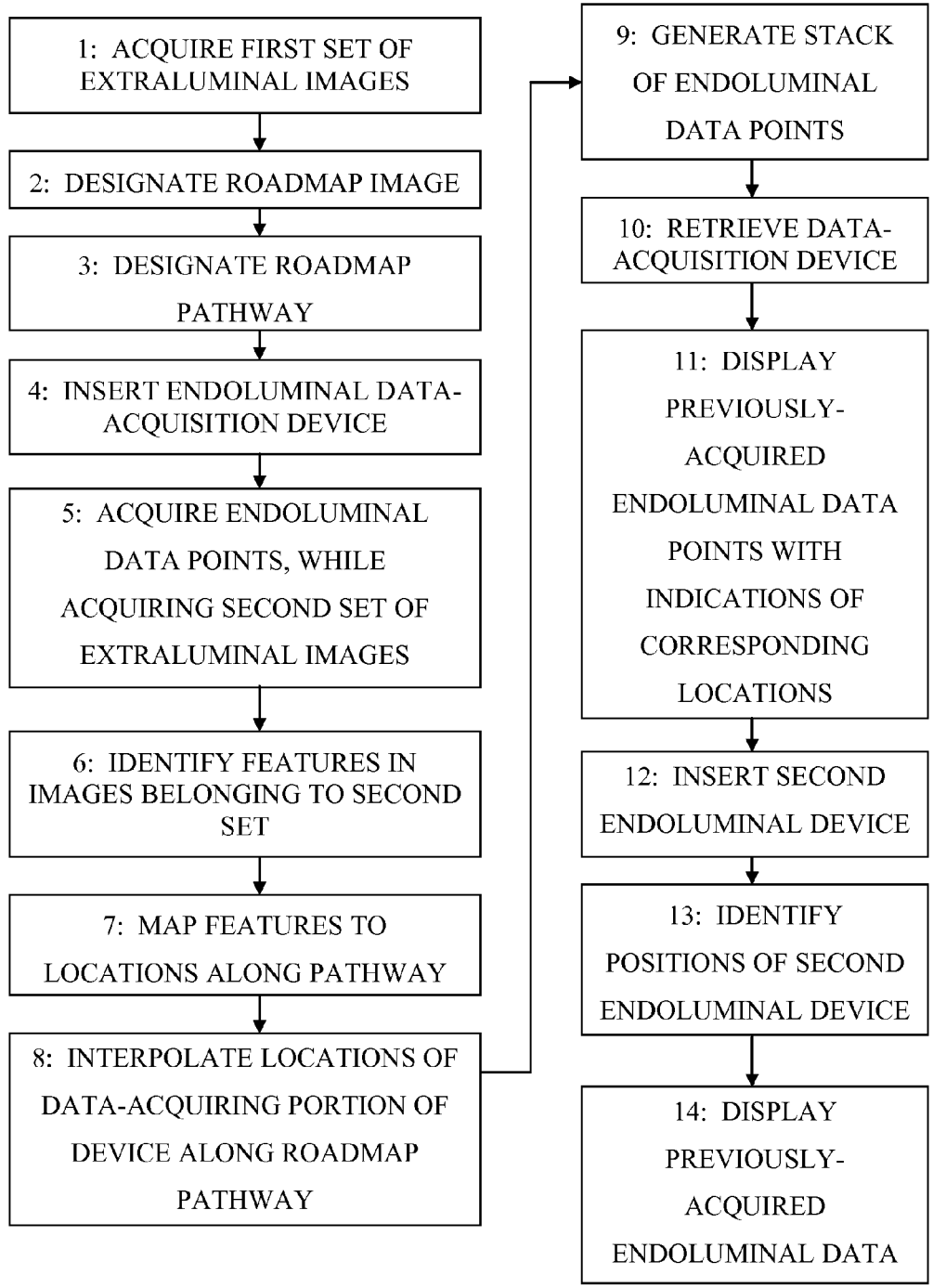
FIG. 1A is a flow chart, at least some of the steps of which are used in procedures that utilize co-use of endoluminal data and extraluminal imaging, in accordance with some applications of the present invention.

The terms "medical tool," "tool", "device," and "probe" refer to any type of a diagnostic or therapeutic or other functional tool including, but not limited to, a cardiovascular catheter, a stent delivery, placement and/or retrieval tool, a balloon delivery and/or placement and/or retrieval tool, a valve delivery and/or repair and/or placement and/or retrieval tool, a graft delivery and/or placement and/or retrieval tool, a tool for the delivery and/or placement and/or retrieval of an implantable device or of parts of such device, an implantable device or parts thereof, a tool for closing a gap, a tool for closing a septal defect, a guide wire, a marker wire, a suturing tool, a clipping tool (such as a valve-leaflet-clipping tool), a biopsy tool, an aspiration tool, a navigational tool, a localization tool, a probe comprising one or more location sensors, a tissue characterization probe, a probe for the analysis of fluid, a measurement probe, an electrophysiological probe, a stimulation probe, an ablation tool, a tool for penetrating or opening partial or total occlusions in blood vessels, a drug or substance delivery tool, a chemotherapy tool, a photodynamic therapy tool, a brachytherapy tool, a local irradiation tool, a laser device, a tool for delivering energy, a tool for delivering markers or biomarkers, a tool for delivering biological glue, an irrigation device, a suction device, a ventilation device, a device for delivering and/or placing and/or retrieving a lead of an electrophysiological device, a lead of an electrophysiological device, a pacing device, a coronary sinus device, an imaging device, a sensing probe, a probe comprising an optical fiber, a robotic tool, a tool that is controlled remotely, an excision tool, a plaque excision tool (such as a plaque excision catheter), or any combination thereof.

The terms "image" and "imaging" refer to any type of medical images or imaging, typically resulting in the generation of a sequence of images and including, but not limited to, imaging using ionizing radiation, imaging using non-ionizing radiation, video, fluoroscopy, angiography, ultrasound, CT, MR, PET, PET-CT, CT angiography, SPECT, Gamma camera imaging, Optical Coherence Tomography (OCT), Near-Infra-Red Spectroscopy (NIRS), Vibration Response Imaging (VRI), optical imaging, infrared imaging, electrical mapping imaging, other forms of functional imaging, Focused Acoustic Computed Tomography (FACT), Optical Frequency Domain Imaging (OFDI), or any combination or fusion thereof. Examples of ultrasound imaging include Endo-Bronchial Ultrasound (EBUS), Trans-Thoracic Echo (TTE), Trans-Esophageal Echo (TEE), Intra-Vascular Ultrasound (IVUS), Intra-Cardiac Ultrasound (ICE), or any combination thereof.

The term "contrast agent," when used in reference to its application in conjunction with imaging, refers to any substance that is used to highlight, and/or enhance in another manner, the anatomical structure, functioning, and/or composition of a bodily organ while the organ is being imaged.

The term "stabilized," when used in the context of displayed images, means a display of a series of images in a manner such that periodic, cyclical, and/or other motion of the body organ(s) being imaged, and/or of a medical tool being observed, is partially or fully reduced, with respect to the entire image frame, or at least a portion thereof.

The term "automatic," when used for describing the generation and utilization of the roadmap, means "without necessitating user intervention or interaction." (Such interaction or intervention may still however be optional in some cases.)

The term "real-time" means without a noticeable delay.

The term "near real-time" means with a short noticeable delay (such as approximately one or two motion cycles of the applicable organ, and, in the case of procedures relating to organs or vessels the motion of which are primarily a result of the cardiac cycle, less than two seconds).

The term "on-line," when used in reference to image processing, or to measurements being made on images, means that the image processing is performed, and/or the measurements are made, intra-procedurally, in real-time or near real-time.

Applications of the present invention are typically used during medical procedures that are performed, in whole or in part, on or within luminal structures. For some applications, apparatus and methods provided herein facilitate the co-use of extraluminal imaging and endoluminal data in performing such medical procedures. Endoluminal data may include imaging data, data derived from measurements, other data, or any combination thereof.

For some applications, the co-use of the endoluminal data and the extraluminal images is performed in the following manner. Endoluminal data are acquired by positioning an endoluminal data-acquisition device along a luminal segment of interest that includes a designated luminal site. Subsequently, while observing extraluminal images of the luminal segment, one or more locations along that segment are indicated by a user input device. In response to the indication of the one or more locations by the user input device, the corresponding, previously-acquired endoluminal images are displayed.

Typically, the designated luminal site includes a site being diagnosed, at which, subject to the outcome of the diagnosis, a therapeutic device will be positioned and deployed, e.g., the site of an anatomical feature, the implantation site of a previously-implanted device, and/or a site at a defined location with respect to the implantation site. For example, the designated luminal site may include a portion of the lumen that is narrow with respect to surrounding portions of the lumen, and/or the site of a lesion.

For some applications, the co-use of the endoluminal data and the extraluminal images is performed in the following manner. Endoluminal data are acquired by positioning an endoluminal data-acquisition device at a designated luminal site. Subsequently, an endoluminal therapeutic device is positioned and deployed at the designated luminal site under extraluminal imaging, while concurrently viewing on-line the endoluminal data that were previously acquired by the endoluminal data-acquisition device at the current location of the therapeutic device. Typically, endoluminal data are acquired at respective endoluminal sites in the vicinity of the designated endoluminal site. Subsequently, when the endoluminal therapeutic device is placed inside the lumen, previously-acquired endoluminal data are displayed and updated, typically automatically and typically on-line, to correspond to the current location of the therapeutic device (or of a portion thereof), the location of the therapeutic device typically changing during the positioning of the therapeutic device.

For some applications, extraluminal imaging and the previously-acquired endoluminal data are co-used such that it is as if the therapeutic device is being positioned and deployed under both real-time extraluminal imaging and real-time endoluminal data acquisition. This is because (a) the extraluminal imaging is performed in real-time, and (b), although the endoluminal data are not acquired in real-time, endoluminal data are displayed that correspond to the current location of the therapeutic device.

In accordance with some applications of the present invention, when the therapeutic device is disposed inside the lumen, the location of the device within the lumen is determined by performing image processing on the extraluminal image of the device inside the lumen.

For some applications, the image processing includes tracking of one or more visible portions of a moving therapy-applying portion of the device in the extraluminal images. Typically, the tracking is performed in real-time, and, typically, in accordance with techniques described in US 2010/0228076 to Blank, which is incorporated herein by reference.

For some applications, the image processing includes stabilization of an image stream produced by the extraluminal imaging. Typically, the stabilization is performed in real-time, and typically in accordance with techniques described in US 2008/0221442 to Tolkowsky, or US 2010/0228076 to Blank, both of which applications are incorporated herein by reference. Typically, the stabilization facilitates the co-use of the endoluminal data with the extraluminal images (particularly in cases of intense organ motion). This is because it is typically easier to determine the luminal location of the therapeutic device based upon a stabilized image stream than to determine the luminal location of the therapeutic device on a native, non-stabilized image stream.

For some applications, the stabilized image stream is also enhanced, typically in real-time, typically in accordance with techniques described in US 2010/0228076 to Blank.

For some applications, during the acquisition of the endoluminal data by the endoluminal data-acquisition device, the location of the endoluminal data-acquisition device is determined by moving the endoluminal data-acquisition device under extraluminal imaging and image processing the extraluminal images to determine the location of a moving data-acquiring portion of the endoluminal data-acquisition device. For some applications, during this stage, the extraluminal image stream is stabilized and/or enhanced, as described hereinabove, to facilitate the determination of the location of the endoluminal data-acquisition device, based upon the extraluminal images. Alternatively, other techniques are used for determining the location of the endoluminal data-acquisition device, as described hereinbelow.

For some applications, the luminal structure to which the apparatus and methods described herein are applied includes a lumen in the vascular system, the respiratory tract, the digestive tract, the urinary tract, or any other luminal structure within a patient's body.

For some applications, the endoluminal data-acquisition device is an imaging probe. For some applications, the imaging probe is an IVUS probe, an EBUS probe, another ultrasound probe, an OCT probe, an NIRS probe, an MR probe, a FACT probe, an OFDI probe, or any combination thereof.

For some applications, the endoluminal data-acquisition device performs additional functions. For example, the endoluminal data-acquisition device may comprise a probe, such as the VIBE(™) RX Vascular Imaging Balloon Catheter, marketed by Volcano Corporation (San Diego, USA), that includes both IVUS and coronary balloon functionalities.

For some applications, the endoluminal data-acquisition device acquires data in a form other than images. For example, the data may include data related to pressure, flow, temperature, electrical activity, oxygenation, biochemical composition, or any combination thereof. For some applications, and typically when data are acquired with respect to a coronary vessel, the endoluminal data-acquisition device is a Fractional Flow Reserve (FFR) probe, and/or an instantaneous wave-free ratio (iFR) probe. For some applications, FFR and/or iFR measurements are determined by performing image-processing on extraluminal images, and the derived FFR and/or iFR measurements are co-registered with endoluminal images of the lumen, using techniques described herein. For some applications, FFR and/or iFR measurements are determined by performing image-processing on endoluminal images, and the derived FFR and/or iFR measurements are co-registered with extraluminal images of the lumen, using techniques described herein. For some applications, endoluminal images are co-registered with extraluminal images of the lumen, using techniques described herein, and FFR and/or iFR measurements are determined by performing image-processing on the co-registered images.

For some applications, the extraluminal imaging is fluoroscopy, CT, MR, PET, SPECT, ultrasound, or any combination thereof.

For some applications, the apparatus and methods described herein are used with a therapeutic device that is positioned and/or deployed at an anatomical feature that requires or potentially requires treatment, such as a partial or total occlusion, a native valve, an aneurism, a dissection, a malformation, a septal defect, a mass suspected of being malignant, a mass suspected of being inflammatory, etc. The endoluminal data are typically acquired at, and/or in the vicinity of, the anatomical feature.

For some applications, apparatus and methods described herein are used with a therapeutic device that is positioned and/or deployed at an implantation site of a previously-implanted device such as a stent, a graft or a replacement valve. The endoluminal data are determined at, and/or in the vicinity of, the implantation site. For example, the techniques described herein may be used during the placement of a new prosthetic aortic valve at the site of (e.g., inside) a previously implanted prosthetic aortic valve that is no longer functioning.

For some applications, apparatus and methods described herein are used with a therapeutic device that is positioned and/or deployed at a defined location relative to a previously-implanted device such as a stent, a graft or a replacement valve. The endoluminal data are determined at and in the vicinity of the defined location. For example, the techniques described herein may be used during the placement of a coronary stent such that the new stent overlaps with or is adjacent to a previously-implanted stent, in order to treat a long lesion and/or a lesion that has diffused along a coronary artery.

Reference is now made to FIG. 1A, which is a flow chart, at least some of the steps of which are used in the course of co-use of endoluminal data and extraluminal imaging, in accordance with some applications of the current invention. It is noted that, for some applications, some of the steps shown in FIG. 1A may be practiced, without all of the steps shown in FIG. 1A necessarily being practiced in combination.

Figure 1B:
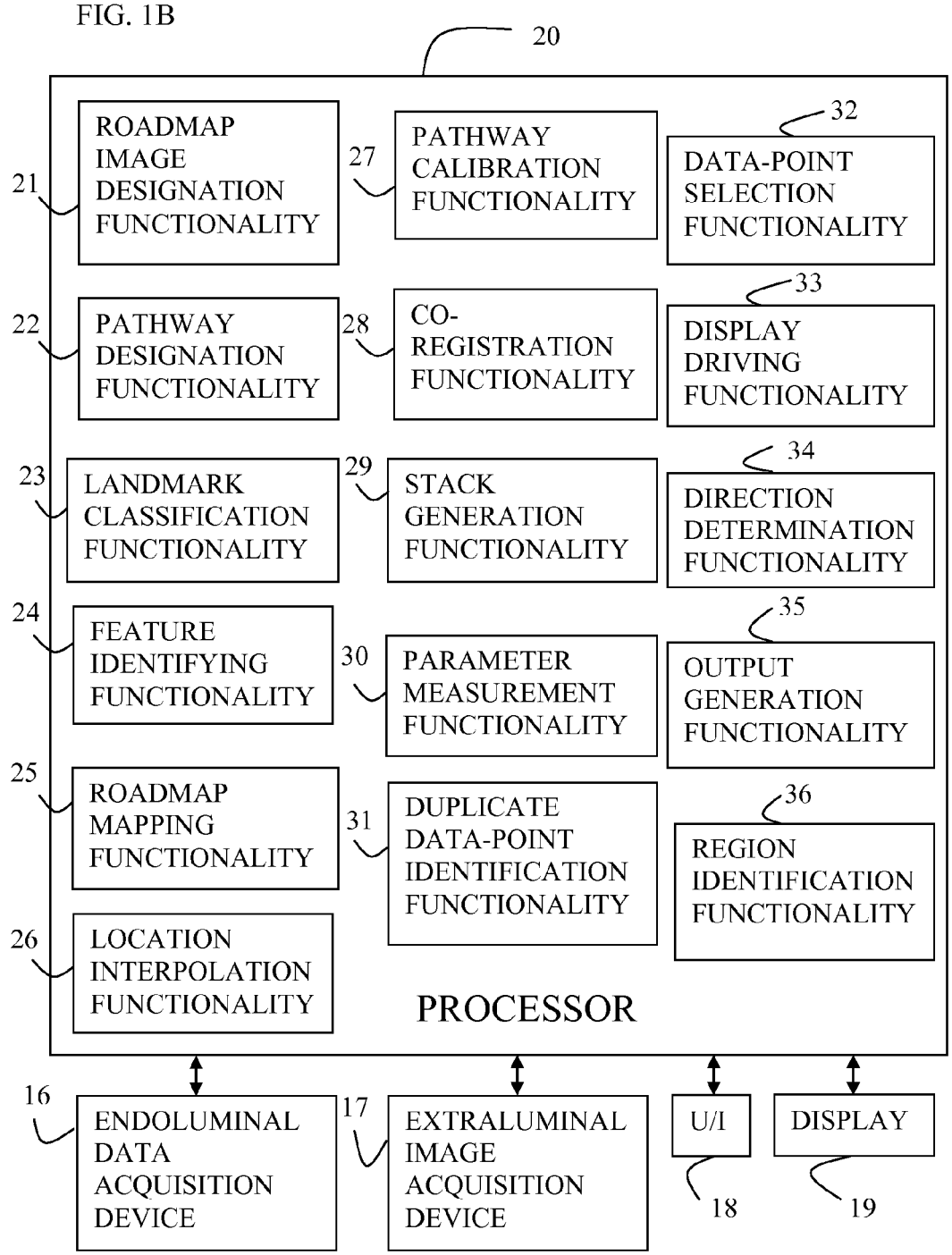
FIG. 1B is a block diagram of an endoluminal data-acquisition device, an extraluminal image acquisition device, a user interface, a display, and a processor that are used, in accordance with some applications of the present invention.

Reference is also made to FIG. 1B, which is a block diagram of an endoluminal data-acquisition device 16, an extraluminal image acquisition device 17, a user interface 18, a display 19, and a processor 20. Processor 20 is typically used to perform the procedure described with respect to FIG. 1A. Processor 20 typically receives inputs via the image acquisition device and the user interface, and generates an output on display 19. For some applications, the user interface includes a keyboard, a mouse, a trackball, a joystick, a touchscreen monitor, a touchpad, a voice-command interface, and/or other types of user interfaces that are known in the art. Typically, the display includes a monitor. For some applications, the display includes a head-up display and/or a head-mounted display, such as Google Glass. Processor 20 typically includes at least some of the following functionalities, the functions of which are described in further detail hereinbelow: roadmap-image-designation functionality 21, pathway-designation functionality 22, landmark-classification functionality 23, feature-identifying functionality 24, roadmap-mapping functionality 25, location-interpolation functionality 26, pathway-calibration functionality 27, co-registration functionality 28, stack-generation functionality 29, parameter-measurement functionality 30, duplicate-data-point-identification functionality 31, data-point-selection functionality 32, display-driving functionality 33, direction-determination functionality 34, output-generation functionality 35, and/or region-identification functionality 36. It is noted that, for some applications, processor 20 does not include all of the above-listed functionalities, but rather includes only some of the above-listed functionalities. It is further noted that, for some applications, more than one processor is used to perform the above-listed functionalities, or a portion thereof. For some applications, more than one extraluminal imaging device is used with processor 20. For example, a first extraluminal imaging device may be used to acquire a first set of extraluminal images (e.g., as described hereinbelow with reference to phase 1 of FIG. 1A), and a second extraluminal imaging device may be used to acquire a second set of extraluminal images (e.g., as described hereinbelow with reference to phase 5 of FIG. 1A).

In phase 1, a first set of extraluminal images is acquired, in which the lumen is visible. Typically, an angiographic image sequence is acquired, while there is contrast agent inside the lumen.

In phase 2, roadmap-image-designation functionality 21 of processor 20 selects an image from the first set of extraluminal images, and designates the selected image as the roadmap image. For some applications, the image is selected from the first set of extraluminal images manually by a user. Alternatively, the image is selected automatically. For some applications, a roadmap image is automatically selected by processor 20, but the processor allows a user to override the automatically-selected roadmap image, by manually designating a roadmap image.

For some applications, the automatic selection of an image frame is performed using techniques described in US 2012/0230565, WO 10/058,398, WO 12/014,212, and/or US 2012/0004537, all of which applications are incorporated herein by reference. For example, the image may be selected based upon the following criteria: (a) the image is acquired at a desired cardiac phase (typically end diastole) and (b) in the image, the contrast agent highlights the lumen. For procedures in which the techniques described herein are performed on a subject's coronary arteries, an image may be selected from the set of images based upon visibility of at least a portion of the coronary arteries in the set of images. For some applications, the angiogram with the greatest visibility of coronary arteries is selected, with such selection typically being automatic. The greatest visibility is typically determined based upon the greatest total number of arteries observed, the greatest number of image pixels attributed to an artery, and/or the greatest image contrast in the appearance of specific arteries. For some applications, an extraluminal image that is based upon a plurality of extraluminal images (e.g., an image that is based upon averaging a plurality of images) is selected and designated as the roadmap image.

Figure 2A:
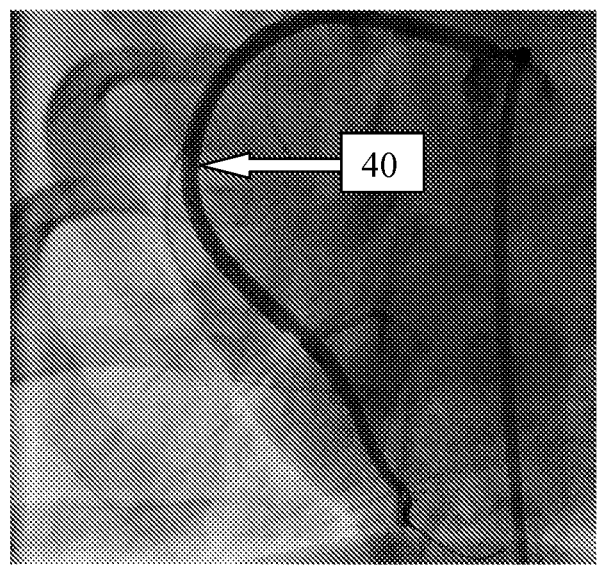
FIGS. 2A-E are schematic illustrations of images of a lumen of a subject, in accordance with some applications of the present invention.

Reference is now made to FIG. 2A, which shows an image of a subject's arteries that has been designated as a roadmap image, in accordance with some applications of the present invention. It may be observed that in the roadmap image, an artery 40, through which an endoluminal data-acquisition device will be inserted, is visible.

Referring again to FIG. 1A, in phase 3, pathway-designation functionality 22 of processor 20 designates a roadmap pathway within the lumen in the roadmap image.

Figure 2B:
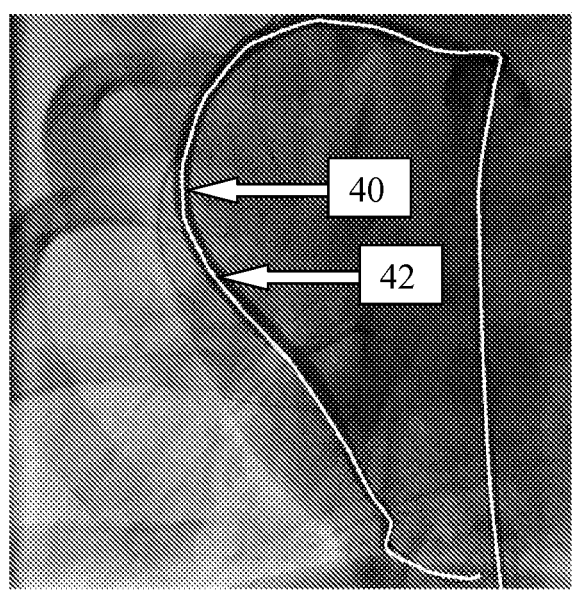

Reference is now made to FIG. 2B, which shows the roadmap image of FIG. 2A, with a roadmap pathway 42 having been designated within artery 40. It is noted that although, in FIG. 2B, path 42 is displayed within the roadmap image, for some applications, the roadmap pathway is designated without the path actually being displayed on a display. Path-designation functionality 22 designates the roadmap pathway in response to a manual user input, and/or automatically. For example, the path may be designated by the user indicating some points along the path and the processor completing the path, based upon the manually-indicated points. For some applications, the roadmap pathway is at least partially determined by determining the centerlines of the lumen. For example, the centerlines of the lumen may be determined using techniques for determining the centerline of a lumen described in US 2012/0230565, WO 10/058,398, WO 12/014,212, and/or US 2012/0004537, all of which applications are incorporated herein by reference.

Typically, the roadmap pathway includes at least a portion of the lumen through which the endoluminal data-acquisition device will be moved. Further typically, the roadmap pathway is designated in such a manner as to facilitate mapping to the pathway a plurality of features that are typically visible in extraluminal images of the lumen that are acquired during the movement of the endoluminal data-acquisition device through the lumen, as described in further detail hereinbelow with reference to phase 7 of the procedure. For some applications, such features include features associated with the endoluminal data-acquisition device such as a data-acquiring portion of the endoluminal data-acquisition device (e.g., the endoluminal data-acquisition device head), radiopaque markers that are disposed at a fixed location with respect to the data-acquiring portion of the endoluminal data-acquisition device (e.g., endoluminal data-acquisition device head), a guiding catheter through which the endoluminal data-acquisition device is inserted, the distal end of the guiding catheter, a catheter through which the data-acquiring portion of the endoluminal data-acquisition device is moved and/or a portion thereof, and/or a guidewire over which the endoluminal data-acquisition device is inserted and/or a portion thereof, etc. For some applications, such features include anatomical features, such as bifurcations, lesions, calcifications, etc. Alternatively or additionally, such features include previously-implanted medical devices, such as a stent, or a valve. Such features may be disposed within the lumen through which the endoluminal data-acquisition device is moved, or in a portion of the subject's body in the vicinity of the lumen, e.g., in a lumen that branches from the lumen through which the endoluminal data-acquisition device is inserted. For applications in which some of the features are disposed in a portion of the subject's body in the vicinity of the lumen, the roadmap pathway in the roadmap image typically extends to the portion of the subject body, even if the portion of the subject's body is not within the lumen. In accordance with respective applications, the roadmap pathway may be shaped as a curve, a polygon, a branching set of lines and/or curves, and/or another shape.

For some applications, processor 20 includes landmark-classification functionality 23. The landmark-classification functionality classifies regions within the roadmap image as corresponding to locations within the roadmap image within which given features are likely to be. For some applications, such features include features associated with the endoluminal device such as a data-acquiring portion of the endoluminal data-acquisition device (e.g., the endoluminal data-acquisition device head), radiopaque markers that are disposed at a fixed location with respect to the data-acquiring portion of the endoluminal data-acquisition device (e.g., the endoluminal data-acquisition device head), a guiding catheter through which the endoluminal data-acquisition device is inserted, the distal end of the guiding catheter, a catheter through which the data-acquiring portion of the endoluminal data-acquisition device is moved and/or a portion thereof, and/or a guidewire over which the endoluminal data-acquisition device is inserted and/or a portion thereof, etc. For some applications, such features include anatomical features, such as bifurcations, lesions, calcifications, etc. Alternatively or additionally, such features include previously-implanted medical devices, such as a stent, or a valve. Such features may be disposed within the lumen through which the endoluminal data-acquisition device is moved, or in a portion of the subject's body in the vicinity of the lumen, e.g., in a lumen that branches from the lumen through which the endoluminal data-acquisition device is inserted.

For some applications, the landmark-classification functionality classifies landmarks in response to a manual input from a user. Alternatively or additionally, the landmark-classification functionality classifies landmarks automatically. For example, the landmark-classification functionality may analyze the angiographic sequence from which the roadmap was generated. In some of the frames of the angiographic sequence, a portion of the above-described features may be visible, and in other frames of the angiographic sequence, portions of the lumen may be visible. Thus, the landmark-classification functionality may determine where respective features are with respect to the vessel, and, in response thereto, may classify regions within the roadmap image as corresponding to locations within the roadmap image within which respective features are likely to be. Alternatively or additionally, the landmark-classification functionality may classify regions within the roadmap image as corresponding to locations within the roadmap image within which the above-described features are likely to be, by analyzing extraluminal images that are acquired subsequent to the generation of the roadmap (e.g., extraluminal images that are acquired in phase 5 of the procedure).

Referring again to FIG. 1A, in phase 4, the endoluminal data-acquisition device is inserted toward a designated site. For some applications, the site is a site being diagnosed, at which, subject to the outcome of such diagnosis, a therapeutic device will be positioned and deployed, e.g., the site of an anatomical feature, the implantation site of a previously-implanted device, and/or a site at a defined location with respect to the implantation site, as described hereinabove.

In phase 5, a plurality of endoluminal data points (e.g., images), are acquired by the endoluminal data-acquisition device, while the endoluminal data-acquisition device is being moved through the lumen. At the same time, while the endoluminal data-acquisition device is being moved through the lumen, a second set of extraluminal images are acquired of the endoluminal data-acquisition device within the lumen. Typically, the second set of extraluminal images are acquired while there is an absence of contrast agent within the lumen. For example, a set of fluoroscopic images of the lumen may be acquired. Alternatively, the second set of extraluminal images are acquired in the presence of contrast agent in the lumen.

It is noted that, in general, the scope of the present application includes performing the techniques described herein with an endoluminal data-acquisition device that acquires data points while the data-acquisition device is being advanced distally through the lumen, and/or an endoluminal data-acquisition device that acquires data points while the data-acquisition device is being refracted proximally through the lumen. It is further noted that, in general, the scope of the present application includes performing the techniques described herein with an endoluminal data-acquisition device that acquires images of the lumen and/or a data-acquisition device that acquires functional data regarding the lumen.

Typically, data are acquired at and/or in the vicinity of the designated site. Typically, a plurality of data points (e.g., images) are acquired at respective locations along the lumen. It is noted that, for some applications, data are acquired subsequent to the initial insertion of the data-acquisition device into the lumen. For example, when data are acquired from blood vessels, the data-acquisition device is typically inserted into the blood vessel to beyond the site of interest under extraluminal imaging (e.g., fluoroscopy), and data acquisition is performed during (manual or automated) pullback of the data-acquisition device through the blood vessel. In alternative applications, e.g., when data are acquired from an endobronchial airway, data are typically acquired by the data-acquisition device during insertion of the data-acquisition device into the airway.

For some applications, the commencement and/or termination of pullback are identified, typically automatically and typically on-line, by means of image processing. For some applications, the image processing is performed by an image comparator which identifies a change (such as in the color of image pixels or in the geometry of image features) in the sequentially-acquired endoluminal images, and interprets the change as indicating the commencement of pullback. For some applications, the image processing is performed by an image comparator which identifies a diminishing change in the sequentially-acquired endoluminal images, and interprets the diminishing change as indicating the termination of pullback.

For some applications, the commencement and/or termination of pullback are identified by means of a signal transmitted by the pullback unit and/or by the endoluminal data-acquisition system. For some applications, the commencement and/or termination of pullback are indicated by means of user input.

In phase 6, feature-identifying functionality 24 of processor 20 identifies, within at least a portion of the images belonging to the second set of extraluminal images, a plurality of features that are visible within the images. The feature-identifying functionality classifies the features as potentially being a given type of feature. For some applications, such feature types include features associated with the endoluminal device such as a data-acquiring portion of the endoluminal data-acquisition device (e.g., the endoluminal data-acquisition device head), radiopaque markers that are disposed at a fixed location with respect to the data-acquiring portion of the endoluminal data-acquisition device (e.g., the endoluminal data-acquisition device head), a guiding catheter through which the endoluminal data-acquisition device is inserted, the distal end of the guiding catheter, a catheter through which the data-acquiring portion of the endoluminal data-acquisition device is moved and/or a portion thereof, and/or a guidewire over which the endoluminal data-acquisition device is inserted and/or a portion thereof, etc. For some applications, such features include anatomical features, such as bifurcations, lesions, calcifications, etc. Alternatively or additionally, such features include previously-implanted medical devices, such as a stent, or a valve. Such features may be disposed within the lumen through which the endoluminal data-acquisition device is moved, or in a portion of the subject's body in the vicinity of the lumen, e.g., in a lumen that branches from the lumen through which the endoluminal data-acquisition device is inserted.

For some applications, features are identified in accordance with techniques described in US 2012/0230565, WO 10/058,398, WO 12/014,212, and/or US 2012/0004537, all of which applications are incorporated herein by reference. For some applications, feature-identifying functionality 24 of processor 20 uses one or more of the following techniques to identify and/or classify the above-described features within the images belonging to the second set of extraluminal images:

a. Identifying features using image processing techniques (e.g., detecting vesselness, using a hessian filter, using corner detection, using directional filters, etc.)

b. Optionally, radiopaque markers can be detected using techniques described in US 2012/0230565 and/or in WO 10/058,398, both of which applications are incorporated herein by reference. For example, the automatic identification of markers may include some or all of the following phases, which are typically performed in real-time:

1. Pre-processing: Individual image frames (or a region of interest (ROI) within such frames) are pre-processed in order to facilitate the subsequent identification of markers. Such pre-processing typically comprises the reduction of static and/or dynamic noise, background removal, or a combination thereof. For some applications, a median filter, a Mexican hat filter, a directional Mexican hat filter, and/or a low-pass filter is applied to the individual image frames. For some applications, the preprocessing includes the detection and removal from the image frames of CABG wires, wires and/or electrodes of implanted tools such as pacemakers or defibrillators, and/or wires and/or electrodes of external devices such as an ECG monitor, and/or an external defibrillator.

2. Filtering of non-marker-like features: Individual image frames (or a region of interest within such frames) are processed to filter out remaining features that are clearly not markers. For some applications, the filtering includes the application to the image frames of a median filter, a Mexican hat filter, a directional Mexican hat filter, a maximal stable external regions (MSER) filter, an MSER-like filter, a Hessian filter, or a combination thereof.

3. For some applications, Hessian eigenvalues are calculated for each pixel in each image frame, or for all pixels within an ROI of the image frame. Typically, local clusters of pixels with high minimal eigenvalues represent a "paraboloid-like" area in the image and are identified as potential radiopaque markers.

4. Scoring: Remaining features in individual image frames (or a region of interest within such frames) are assigned a "fitness" score (i.e., a "markerness" score, or a "dotness" score in the case of the most common markers), describing the likelihood that they are markers. For some applications, the score is calculated from the abovementioned filtering.

5. Matching: Remaining features in individual image frames (or a region of interest within such frames) are analyzed for matching with one another. For example, in the case of aiming to detect the two radiopaque markers of a coronary balloon, pair matching is performed. Such matching is typically performed based upon relative location, distance, orientation, visual similarity, and/or other factors.

6. Detection: For some applications, once a pair of clusters (the clusters within the set being strong candidates to be tool markers) has been identified as being at a similar distance from one another and/or relative angle to one another in several consecutive image frames, the pair of clusters is determined to be the markers.

c. Optionally, the guiding catheter, the guidewire, and elongated objects such as the endoluminal data-acquisition device head, can be detected using techniques described in US 2012/0230565, and/or in WO 10/058,398, both of which applications are incorporated herein by reference. For example, the image frame may be analyzed such that the extent to which a given pixel is likely to be an element of an image of an object in applicable areas of the image frame is determined. For example, this may be determined by means of a filter, such as the filter described in an article by Frangi et al., entitled "Multi-scale vessel enhancement filtering" (Medical Image Computing and Computer Assisted Intervention—MICCAI 1998—Lecture Notes in Computer Science, vol. 1496, Springer Verlag, Berlin, Germany, pp. 130-137), which is incorporated herein by reference, by means of a filter that performs enhancement, and/or by detection and/or segmentation of curvilinear structures. For some applications, a filter is used that is similar to the filter described by Frangi, but that differs from the filter described by Frangi (a) in that a homogeneous function is used, and/or (b) in the multipliers employed for the normalization of scales.

d. Classifying features using machine learning techniques. For example, one or more of the following machine learning techniques may be used: Support Vector Machine (SVM), Deep Believe Networks, Neural Networks, and/or Random Decision Forest.

Figure 2C:
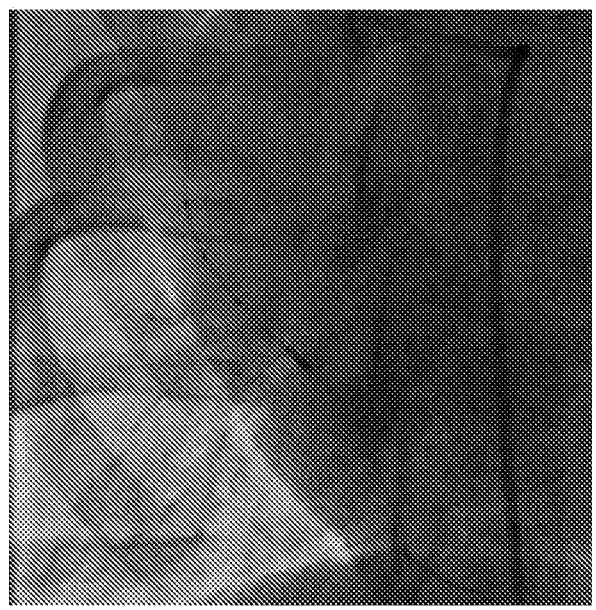
Figure 2D:
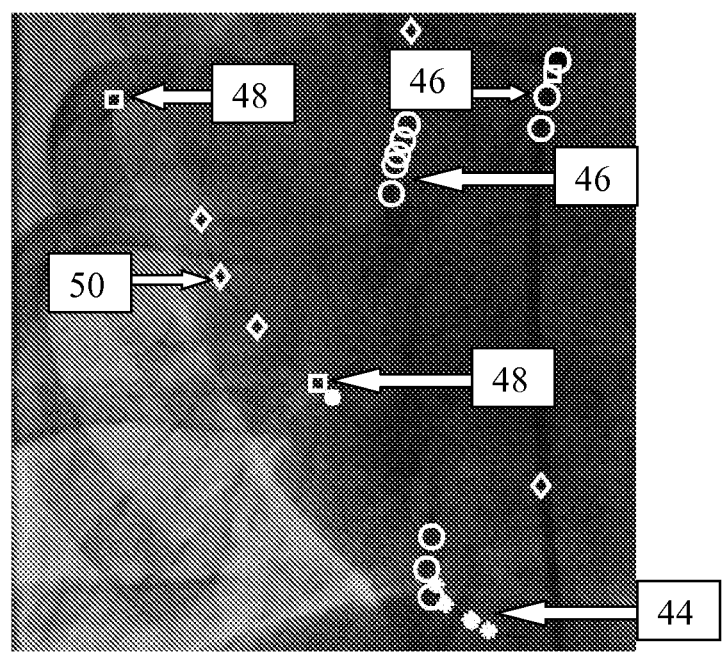

Reference is now made to FIGS. 2C and 2D, which show, respectively, an example of a raw fluoroscopic image frame, and the fluoroscopic image frame with a plurality of features identified and classified therein, in accordance with some applications of the present invention. As indicated by the shapes of the features shown in FIG. 2D, the feature-identifying functionality of the processor typically classifies the identified features as potentially being a given type of feature. For example, the features indicated by stars 44 are classified as corresponding to the radiopaque tip of the guidewire, the features indicated by circles 46 are classified as corresponding to the guiding catheter, the features indicated by squares 48 are classified as corresponding to the device head, and the features indicated by diamonds 50 are classified as corresponding to the radiopaque markers that are typically disposed proximally to an IVUS device head. As described hereinabove, the classification is typically performed using machine learning techniques such as SVM, Deep Believe Networks, Neural Networks, and/or Random Decision Forest.

It is noted that typically, at this stage in the procedure, some of the features classified as potentially being a given type of feature are false. Such false features are typically identified based upon the mapping that is performed in phase 7 of the procedure, as described in further detail hereinbelow.

Referring again to FIG. 1A, in phase 7 of the procedure, roadmap-mapping functionality 25 of processor 20 maps at least a portion of the identified features of given images of the second set of extraluminal images to locations along the roadmap pathway on the roadmap image. For some applications, an arrangement of two features within the image is compared to a shape of at least a portion of the roadmap pathway. Typically, the mapping is performed by comparing an arrangement of three or more of the features within the image to a shape of at least a portion of the roadmap pathway. For example, the roadmap-mapping functionality may determine vector(s) defined by pair(s) of features in the image belonging to the second set of extraluminal images (e.g., a vector defined by a radiopaque marker of the guidewire tip and a radiopaque marker of the endoluminal data-acquisition device head). Alternatively or additionally, the roadmap-mapping functionality may determine distance(s) between by pair(s) of features in the image belonging to the second set of extraluminal images (e.g., a vector defined by a radiopaque marker of the guidewire tip and a radiopaque marker of the endoluminal data-acquisition device head). Further alternatively or additionally, the roadmap-mapping functionality may determine an arrangement of vectors defined by two or more pairs of features in the image belonging to the second set of extraluminal images (e.g., by determining an angle between (a) a vector defined by a radiopaque marker of the guidewire tip and a radiopaque marker of the endoluminal data-acquisition device head, and (b) a vector defined by the radiopaque marker of the endoluminal data-acquisition device head and the guiding catheter).

The arrangement of features within the image belonging to the second set of extraluminal images is compared to a shape of at least a portion of the roadmap pathway. For some applications, the arrangement of features within the image belonging to the second set of extraluminal images is compared to an arrangement of two or more locations within the roadmap pathway. Typically, the arrangement of features within the image belonging to the second set of extraluminal images is compared to an arrangement of three or more locations within the roadmap pathway. For example, the roadmap-mapping functionality may compare the arrangement of features within the image belonging to the second set of extraluminal images to vector(s) defined by pair(s) of points that are disposed on the roadmap pathway. Or, the roadmap-mapping functionality may compare the arrangement of features within the image belonging to the second set of extraluminal images to an arrangement of vectors defined by two or more pairs of points that are disposed on the roadmap pathway.

Typically, between the acquisition of the roadmap image, and the acquisition of a given image belonging to the second set of extraluminal images, the lumen has undergone changes in location and shape (e.g., due to the subject's respiratory cycle, due to the subject's cardiac cycle, due to other movement of the subject, and/or due to the devices within the lumen having moved the lumen). Typically, by performing the above-described comparison, the roadmap-mapping functionality determines an estimated measure of a transformation (e.g., stretching, rotation, shrinking, etc.) that should be applied to the given extraluminal image, such that a best fit of the identified features within the extraluminal image to the roadmap pathway is determined. Based upon the determined transformation, the roadmap-mapping functionality determines locations of portions of the extraluminal image (e.g., features corresponding to the endoluminal data-acquisition device) with respect to the roadmap image, by applying the transformation to at least some points on the extraluminal image. In particular, the roadmap-mapping functionality determines where, on the roadmap pathway within the roadmap image, respective features associated with the endoluminal device were disposed, at the time when the extraluminal image was acquired.

For some applications, the mapping is performed using the following technique:

Assuming:

$q_j$ is the $\{x,y\}$ coordinate of feature j in one of the second set of extraluminal images (i.e., one of the extraluminal images that was acquired during the data-acquisition by the endoluminal data-acquisition device), where $1 \le j \le m$; and $p_i$ is the $\{x,y\}$ coordinate of a general point along the roadmap pathway within the roadmap image, where $1 \le i \le n$;

the mapping provides T: $\{1 \ldots m\} \to \{1 \ldots n\}$.

Thus, the mapping maps feature $q_j$ (in the extraluminal image) to position $P_{T(j)}$ (in the roadmap image).

As described hereinabove, typically, body lumens undergo various deformations, such as due to the cardiac cycle, respiration, and other possible movements of the subject. For some applications, in order to perform the mapping, the mapping functionality assumes that the general shape of the lumen, and the relationships among features along the lumen, are generally preserved throughout the motion of the lumen. In order to find the desired index mapping, a deformation measure is defined for each mapping T. The desired index mapping is obtained by minimizing the deformation measure.

Assuming that the vectors $q_{j1}-q_{j2}$ and $P_{T(j1)}-P_{T(j2)}$ are similar, for all $j_1, j_2$, the deformation measure is defined by:

$$\sum_{1 \le j_1, j_2 \le m} C_{j_1 j_2} \cdot \text{Similarity}(q_{j_1} - q_{j_2}, p_{T(j_1)} - p_{T(j_2)}) \quad \text{(equation 1)}$$

where the coefficients $C_{j_1 j_2} \ge 0$

For example, the similarity function may be defined in one of the following ways:

$$\text{Similarity}(u, v) = \|u - v\|^2 \quad \text{(equation 2)}$$

$$\text{Similarity}(u, v) = \alpha \frac{(\|v\| - \|u\|)^2}{\|u\|} + \beta \frac{\|u - v\|^2}{\|u\|} \quad \text{(equation 3)}$$

$$\alpha, \beta \ge 0$$

The deformation measure provided by equation 1 is computed using the similarity provided by equation 2 or equation 3, such as to provide transformation T. Thus, the location of each feature from the extraluminal image within the roadmap image is provided by $P_{T(j)}$. The transformation that minimizes the deformation measure is typically computed.

The effect of performing the above-described mapping algorithm is to compare vectors defined by respective pairs of the identified features to vectors defined by respective pairs of locations within the roadmap pathway. For example, the mapping algorithm may compare a vector defined by the spacing between the two stars at the bottom of FIG. 2D to a vector defined by a pair of locations along the roadmap pathway. For some applications, the mapping algorithm compares a plurality of vectors defined by respective pairs of the identified features to a plurality of vectors defined by respective pairs of locations within the roadmap pathway. By performing the minimizing of the deformation measure, the algorithm finds a way of best fitting the identified features within a given extraluminal image to the roadmap pathway.

Figure 2E:
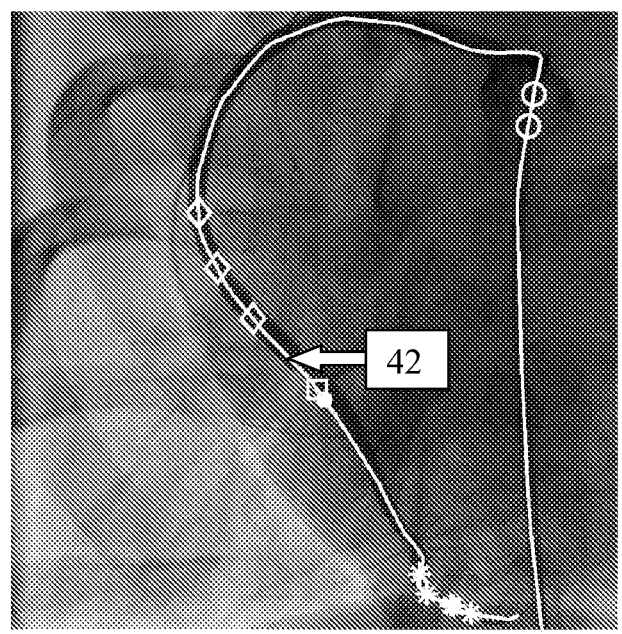

Reference is now made to FIG. 2E, which demonstrates, figuratively, the result of performing the minimizing of the deformation measure. As shown in FIG. 2E, features that were identified in the extraluminal image have been mapped to locations on roadmap pathway 42 of the roadmap image in such a manner as to minimize the deformation measure (i.e., in a manner that minimizes the extent to which the arrangement of identified features must be deformed, in order that the identified features fit upon the roadmap pathway). It is noted that typically, the features identified in the extraluminal image are not actually displayed upon the roadmap image, as shown in FIG. 2E. Rather, as stated above, FIG. 2E demonstrates, figuratively, the result of performing the minimizing of the deformation measure. Based upon the above-described mapping procedure, it is determined where, on the roadmap pathway in the roadmap image, respective features associated with the endoluminal device were disposed, at the time when the extraluminal image was acquired.

For some applications, in performing the mapping, one or more of the following restrictions are applied such as to restrict the possible locations on the roadmap pathway to which a given feature of the extraluminal image may be mapped:

1) As described hereinabove, for some applications, landmark-classification functionality 22 classifies regions within the roadmap image as corresponding to locations within the roadmap image within which features are likely to be. For some applications, in performing the mapping, the roadmap-mapping functionality restricts the mapping of features in an extraluminal image, such that a given feature is only allowed to be mapped to the corresponding region of the roadmap image. Thus, for example, if a region of the roadmap image has been classified as corresponding to the guiding catheter, the roadmap-mapping functionality will not allow features that are identified as portions of the guidewire to be mapped to that region.

2) For given images of the second set of extraluminal images that are acquired in temporal proximity to one another, features of a given type (e.g., the endoluminal data-acquisition device head) are classified by assuming that, in each of the extraluminal images, the features of the given type must be in close proximity to each other. This is because it is assumed that since the extraluminal images were acquired in temporal proximity to one another, the features could not have moved by more than a given distance between the acquisitions of the respective images. For some applications, in determining the extent to which the features of the given type must be in close proximity to each other in the extraluminal images, the expected velocity of the endoluminal data-acquisition device, and/or the expected foreshortening of the endoluminal data-acquisition device are accounted for.

3) For given images of the second set of extraluminal images that are acquired in temporal proximity to one another, the roadmap mapping functionality will only allow features of a given type (e.g., the endoluminal data-acquisition device head) within the respective extraluminal images to be mapped to locations that are in close proximity to one another along the roadmap pathway. This is because it is assumed that since the extraluminal images were acquired in temporal proximity to one another, the features could not have moved along the roadmap pathway by more than a given distance between the acquisitions of the respective images. For some applications, in determining the extent to which the features of the given type must be in close proximity to each other along the roadmap pathway, the expected velocity of the endoluminal data-acquisition device, and/or the expected foreshortening of the endoluminal data-acquisition device are accounted for.

4) In performing the mapping, the roadmap-mapping functionality accounts for known dimensions associated with the features. For example, by way of illustration, the roadmap-mapping functionality may account for the known separation between adjacent markers, the known length of the endoluminal data-acquisition device head, a known dimension of the guide catheter, and/or a known dimension of the guidewire. The roadmap-mapping functionality restricts the mapping of features in an extraluminal image to the roadmap pathway, by only allowing mapping that does not change the known dimensions (and/or the relative dimensions) associated with the features by more than a threshold amount.

5) Given features must be placed in a given order along the roadmap pathway. For example, the guidewire distal tip must typically be the distal-most feature, and the endoluminal data-acquisition device head must be distal to the guide catheter, etc.

The result of performing the mapping on images belonging to the second set of extraluminal images is typically that, for each of the extraluminal images to which the mapping is applied, an estimate is determined of where, at the time when the extraluminal image was acquired, respective features associated with the endoluminal device were disposed upon the roadmap pathway. In particular, for each of the extraluminal images to which the mapping is applied, an estimate is determined of where, at the time when the extraluminal image was acquired, the data-acquiring portion of the data-acquisition device (e.g., the endoluminal data-acquisition device head) was disposed upon the roadmap pathway.

Typically, processor 20 determines which endoluminal data points were acquired at the same time as respective extraluminal images. For example, a single computer (or two or more computers that are time-synchronized) may operate both the extraluminal imaging and the endoluminal data-acquisition, and the computer may log the times at which extraluminal images and endoluminal data-points were acquired. Or, the processor may determine which endoluminal data points were acquired at the same time as respective extraluminal images based upon known frame rates at which the extraluminal images and the endoluminal data points are acquired. By determining an estimate of where, at the time when the extraluminal image was acquired, the data-acquiring portion of the data-acquisition device (e.g., the endoluminal data-acquisition device head) was disposed upon the roadmap pathway, the processor determines the location with respect to the roadmap pathway of the endoluminal data point that was acquired at the same time as the extraluminal image.

Referring again to FIG. 1A, in phase 8 of the procedure, location-interpolation functionality 26 of processor 20 performs interpolation on the determined locations of the data-acquiring portion of the endoluminal data-acquisition device along the roadmap pathway, such as to determine the location of the data-acquiring portion of the endoluminal data-acquisition device along the roadmap pathway at any time during the movement of the endoluminal data-acquisition device with respect to the lumen (i.e., even at times between acquisitions of extraluminal images belonging to the second set of extraluminal images). Typically, the interpolation is performed by optimizing a cost of a trajectory of the endoluminal data-acquisition device, throughout the pullback. The cost includes parameters such as maintaining a given separation between given features (e.g., between pairs of markers), the velocity of the endoluminal data-acquisition device, movement continuity, and quality of the mapping of the guide catheter. The resulting trajectory is smoothed and the result is a floating point model index of endoluminal data-acquisition device locations along the roadmap pathway. For some applications, the location-interpolation functionality applies parameter estimation techniques to the determined locations of the data-acquiring portion of the endoluminal data-acquisition device along the roadmap pathway. For example, temporal filtration techniques, and/or outlier removal techniques may be applied to the determined locations of the data-acquiring portion of the endoluminal data-acquisition device along the roadmap pathway.

For some applications, in order to perform the interpolation, the roadmap pathway is first calibrated using pathway-calibration functionality 27 of processor 20. The pathway-calibration functionality calibrates the roadmap pathway by determining the relationship between the physical dimension of a portion of the lumen and a number of pixels in a portion of the roadmap pathway that corresponds to the portion of the lumen (e.g., the length in mm along the lumen, per pixel along the roadmap pathway). It is noted that typically, the calibration factors associated with respective portions of a lumen in an image varies, due to respective portions of the lumen being disposed at respective angles with respect to the extraluminal imaging device. Therefore, typically, the pathway calibration functionality determines a plurality of local calibration factors along the roadmap pathway.

For some applications, the calibration is performed based upon known dimensions associated with the features that are identified in the images belonging to the second set of extraluminal images. For example, the pathway-calibration functionality may use a known separation between adjacent markers, the known length of the endoluminal data-acquisition device head, a known dimension of the guide catheter, a known dimension of a radiopaque marker, and/or a known dimension of the guidewire. Since the features are mapped to locations along the roadmap pathway (in accordance with the techniques described hereinabove), the pathway-calibration functionality is able to determine at any given location along the roadmap pathway a calibration factor associated with that location by identifying the number of pixels within the portion of the roadmap pathway that correspond to the known dimension associated with the features.

For some applications, even if the actual dimensions associated with features are not known, the pathway-calibration functionality determines the relative calibration factors of respective portions of the roadmap pathway, based upon the relative number of pixels that a given feature or set of features occupy while the feature or set of features is disposed within the respective portions of the pathway. For some applications, the pathway-calibration functionality determines the calibration factors of respective portions of the roadmap pathway based upon a velocity at which one of the features is known to move. For example, if an endoluminal data-acquisition device is known to be pulled through the lumen (or pushed through the lumen) at a given speed, the pathway-calibration functionality may determine that, over a given time interval, the device moved through a given number of pixels along a given portion of the roadmap pathway. In response thereto, the roadmap-calibration functionality determines the calibration factor associated with the portion of the pathway. For some applications, a scale is placed along the roadmap pathway of the roadmap image based upon the calibration.

For some applications, the calibration is performed using the following technique, the goal of the calibration being to determine the distance between any two points along the roadmap pathway:

1. The roadmap pathway is denoted as a sequence of points $p_i = (x_i, y_i)$, $i = 0, 1 \ldots, n$
2. The calibration is achieved if the distances from $p_0$ to $p_i$ are determined for $i = 0, 1 \ldots, n$.
3. The distances are denoted as $d_i$ ($d_0 = 0$)
4. Using linear interpolation the pathway is parameterized by a continuous parameter $t \in [0, n]$ as follows:

$$x_t = (1 - \alpha(t)) * x_{i(t)} + \alpha(t) * x_{i(t)+1}$$
$$y_t = (1 - \alpha(t)) * y_{i(t)} + \alpha(t) * y_{i(t)+1}$$

-continued where:

$$i = \begin{cases} [t] & \text{if } 0 \le t < n \\ n-1 & \text{if } t = n \end{cases}$$

$$\alpha(t) = t - i(t)$$

$[t]$ is the integer part of t.

5. For pairs of features in the images belonging to the second set of extraluminal images that are disposed at a known physical distance from each other, each mapping to the roadmap pathway yields an equation. If the first feature of the pair is mapped to $(x_t, y_t)$ and the second feature is mapped to $(x_s, y_s)$ and the known distance between the pair of features is denoted as r, the equation can be written as follows:

$$((1-a(s))*d_{i(s)} + a(s)*d_{i(s)+1}) -$$

$$((1-a(t))*d_{i(t)} + a(t)*d_{i(t)+1}) = r$$

(Without loss of generality, it is assumed that s>t.)
(If $d_0$ appears in the equation, it is replaced with 0.)

6. The following regularization equations are generated:

$$W\left(\frac{d_i}{\|p_i - p_{i-1}\|} - \frac{d_{i+1}}{\|p_{i+1} - p_i\|}\right) = 0, i = 1, 2 \ldots, n-1$$

where W is the regularization weight.

7. All the equations generated by steps (5) and (6) are solved by a least square method.

8. The solution yields $d_i$, i=1, 2 . . . , n−1, from which the distance between any two points on the roadmap pathway is calculated, since the distance between two points $p_i$ and $p_j$ can be computed from the estimated distances $d_i$ and $d_j$ as $|d_i - d_j|$.

For some applications, based upon the interpolation of the locations of the endoluminal data-acquisition device along the roadmap pathway (and, optionally, calibration of the roadmap pathway), co-registration functionality 28 of the processor co-registers respective endoluminal data points to respective locations within the roadmap image.

Referring again to FIG. 1A, in phase 9 of the procedure, stack-generation functionality 29 of processor 20 generates a stack of endoluminal data points, based upon the output of phase 8 of the procedure. For some applications, the endoluminal data points include endoluminal images, and the endoluminal images are arranged in an image stack. Typically, the endoluminal image stack is generated by extracting an endoluminal image at regular intervals of length along the roadmap pathway, and from each image, extracting a cross section of the image (typically, one line of pixels) and placing the cross section in the stack. Thus, the images are positioned at locations within the stack corresponding to relative locations along the roadmap pathway within the lumen at which the images were acquired. For some applications, the endoluminal data points are functional endoluminal data points, and a display of the endoluminal data points is generated, in which the endoluminal data points are positioned at locations corresponding to relative locations within the lumen at which the endoluminal data points were acquired. Typically, the functional endoluminal data points are displayed in the stack by displaying a stack of indications of the functional endoluminal data points, locations of the indications within the stack corresponding to relative locations within the lumen at which the endoluminal data points were acquired. For example, numerical indications of the functional endoluminal data points may be displayed and/or representations of the functional endoluminal data points (which may be based upon a color-code, for example) may be displayed. For some applications, indications of non-functional endoluminal data points are displayed in the described manner.

Figure 3A:
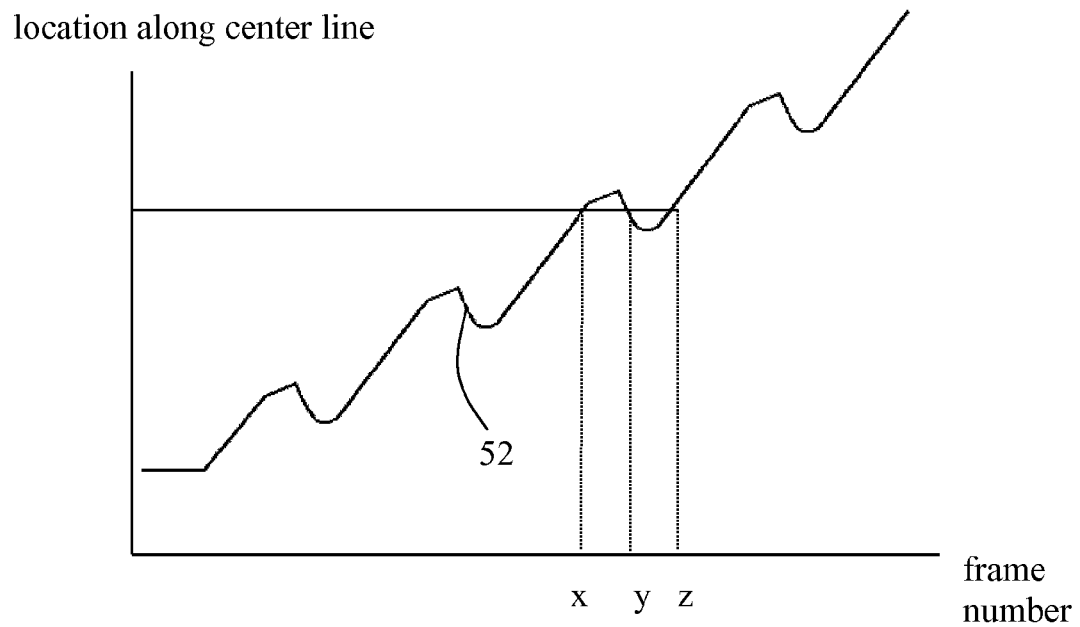
FIG. 3A is a graph indicating a typical type of movement of an endoluminal data-acquisition device during pullback of the device.

Reference is now made to FIG. 3A, which is a graph showing the location along a lumen (e.g., along the center line of the lumen) of a data-acquiring portion (e.g., the head) of an endoluminal data-acquisition device, versus the frame numbers of the endoluminal data points acquired by the data-acquisition device, during pullback of the data-acquisition device. Typically, even during automated pullback of the data-acquisition device, the relative speed at which the data-acquiring portion of the device moves with respect to the lumen, and, in some cases, the direction in which the data-acquiring portion moves with respect to the lumen, varies over the course of the cardiac cycle, due to pulsation of the lumen. As shown on portion 52 of the graph (which typically corresponds to a systolic phase of the cardiac cycle, or a portion thereof), in some cases, the data-acquiring portion of an endoluminal data-acquisition device moves forward (i.e., distally) with respect to the lumen during certain phases of the cardiac cycle, even during pullback (pullback generally being in a distal to proximal direction).

Further typically, as a result of the data-acquiring portion moving forward with respect to the lumen, in some cases, two or more endoluminal data points are acquired at a single location along the lumen. For example, as shown in FIG. 3A, frames x, y, and z are acquired at a single location along the lumen. Frame x is acquired pre-systole, while the data-acquisition device is moving in a distal to proximal direction with respect to the lumen, frame y is acquired during systole, while the data-acquisition device is moving in a proximal to distal direction with respect to the lumen, and frame z is acquired post-systole, while the data-acquisition device is moving back past the same location in a distal to proximal direction with respect to the lumen.

For some applications, manual pullback of the endoluminal data-acquisition device is performed by an operator. In some cases, during manual pullback, the operator pushes the data-acquisition device forward at times in order to view a given region for a second time. As a result, the data-acquisition device typically acquires a plurality of endoluminal data points of given locations within the region. For example, a first data point may be acquired during the initial pullback past the location in the distal to proximal direction, a second data point may be acquired when the data-acquisition device is pushed forward by the operator in the proximal to distal direction, and a third data point may be acquired when the data-acquisition device is, subsequently, pulled back past the location in the distal to proximal direction for a second time.

Figure 3B:
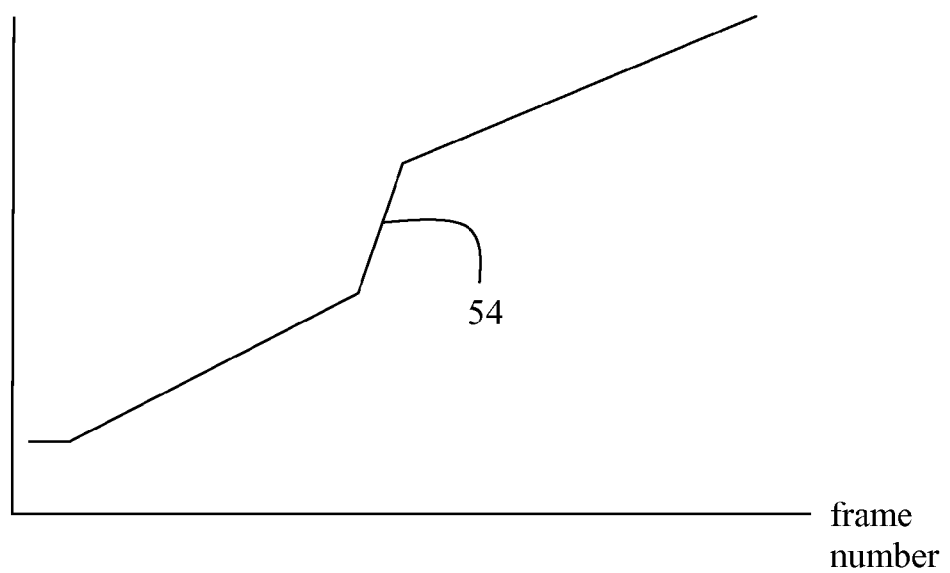
FIG. 3B is a graph indicating another typical type of movement of an endoluminal data-acquisition device during pullback of the device.

Reference is now made to FIG. 3B, which is a graph showing the location along a lumen (e.g., along the center line of the lumen) of a data-acquiring portion of an endoluminal data-acquisition device, versus the frame numbers of the endoluminal data points acquired by the data-acquisition device, during pullback of the data-acquisition device. As indicated in FIG. 3B, for some applications, during some of the pullback of the endoluminal data-acquisition device (e.g., along portion 54 of the graph), the data-acquisition device moves at a greater speed than the regular pullback speed of the data-acquisition device, such that the location of the endoluminal data-acquisition device within the extraluminal images of the lumen cannot be determined by performing image processing on the extraluminal images. For example, a region (such as a narrow region) of the lumen may provide resistance to the pullback of the data-acquisition device, such that the data-acquisition device becomes stuck for a period of time, following which the data-acquisition device pulls back quickly from the region of resistance. If, by way of example, the extraluminal imaging device acquires an extraluminal image once every 1/15th of a second, and the data-acquisition device pulls back from an area of resistance at a speed of 150 mm/s, then this may result in there being no extraluminal image of the data-acquisition device within a 10 mm section of the lumen. Thus, endoluminal data points that were acquired within the 10 mm section cannot be accurately co-registered to corresponding locations within the lumen in the extraluminal image.

Typically, stack-generation functionality 29 generates a corrected stack of endoluminal data points (e.g., endoluminal images) in which:

(a) there are one or more gaps in the stack at a portion of the stack corresponding to a region within the lumen within which the endoluminal data-acquisition device has not been imaged by the extraluminal imaging device;

(b) endoluminal data points that were acquired during forward motion of the endoluminal data-acquisition device are either rejected, or are appropriately placed within the stack; and/or (c) at least one data point corresponding to a location along the lumen that has two or more endoluminal data point corresponding thereto is rejected from being used in the stack.

Figure 3C:
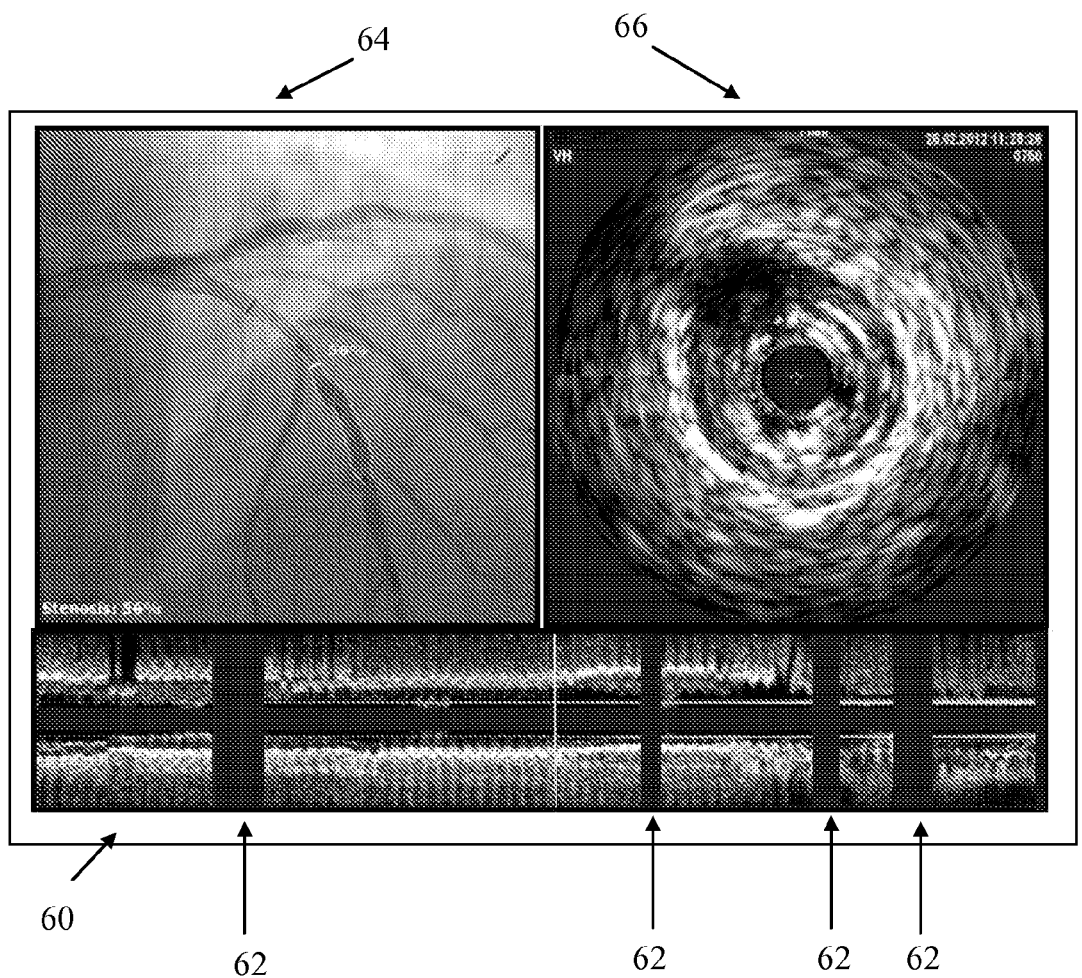
FIG. 3C is a schematic illustration of an endoluminal image stack that includes gaps therein, in accordance with some applications of the present invention.

Reference is now made to FIG. 3C, which shows an endoluminal image stack 60 that has gaps 62 therein, in accordance with some applications of the present invention. Typically, as shown, the endoluminal image stack is shown on the same screen as the roadmap image 64. Further typically, an endoluminal image 66 corresponding to a location along the roadmap pathway that is selected by the user is shown on the screen. For some applications, processor 20 identifies regions of the lumen within which the endoluminal data-acquisition device has not been imaged by the extraluminal imaging device (e.g., due to the endoluminal data-acquisition device moving through the region too quickly). In response to a user selecting a location on the roadmap image that is within such a region, the processor generates an indication that there is no endoluminal image corresponding to that location. For example, in response to the user selecting the location, the processor may not display any endoluminal image, or the system may display an endoluminal image corresponding to a location adjacent to the selected location, and generate an indication that this is the case. Alternatively, the processor may display an endoluminal image that was acquired by the endoluminal data-acquisition device while the data-acquisition device moved through the region, and generate an indication that the precise location within the region of the lumen corresponding to the endoluminal image is not known.

It is noted that although FIG. 3C and the description thereof relate to endoluminal images, the scope of the present invention includes applying similar techniques to other forms of endoluminal data points (e.g., functional endoluminal data points), mutatis mutandis.

For some applications, the processor identifies regions of the lumen within which the endoluminal data-acquisition device has not been imaged by the extraluminal imaging device. In response thereto, the processor displays gaps in the endoluminal image stack at the locations within the stack corresponding to the regions within the lumen, as shown in FIG. 3C. For some applications, the processor assumes that the endoluminal data-acquisition device moved through the region at a constant speed. The processor interpolates locations of the endoluminal images that were acquired by the endoluminal data-acquisition device while the data-acquisition device moved through the region, along the length of the portion within the endoluminal image stack that corresponds to the region.

For some applications, processor 20 includes parameter-measurement functionality 30. In response to a user designating a portion of the stack of endoluminal data points, the parameter-measurement functionality determines a parameter of the portion of the roadmap pathway corresponding to the designated portion of the stack, based upon the co-registration of the stack to the roadmap pathway. For some applications, the parameter-measurement functionality determines the length of the portion of the roadmap pathway corresponding to the designated portion of the stack, based upon the co-registration of the stack to the roadmap pathway. For example, a user may designate a portion of an endoluminal data stack that contains a lesion, and in response thereto, the parameter-measurement functionality determines a length of the portion of the roadmap pathway corresponding to the designated portion of the stack, based upon the co-registration of the stack to the roadmap pathway. For some applications, the parameter-measurement functionality performs the aforementioned measurements, even if the endoluminal data stack that is displayed to the user has not been corrected (to account for duplicate data points and gaps), as described hereinabove. Typically, length measurements that are performed with respect to the roadmap pathway are more accurate than if the length measurements were performed upon a raw data stack, inter alia, because local calibration factors along the roadmap pathway are known, as described hereinabove.

For some applications, length measurements are displayed on the endoluminal data stack. For some applications, measurements are automatic. For some applications, measurements are performed interactively by the user. For some applications, measurement of a different parameter (e.g., lumen diameter) is performed in a generally similar manner to that described above with respect to length measurement, mutatis mutandis. For some applications, a scale (or some other known dimension) presented on the endoluminal data stack provides a reference dimension for calibrating the measurements. For some applications, based upon the co-registration of the endoluminal data stack to the roadmap image, a scale is displayed with reference to the endoluminal data stack.

For some applications, forward motion of the endoluminal data-acquisition device that is (a) due to pulsation of the lumen, and/or (b) due to an operator of the data-acquisition device pushing the data-acquisition device forward, is accounted for in order to facilitate co-registration of the endoluminal data points to an extraluminal image. Typically, in order to facilitate co-registration, the system identifies redundant data points (i.e., data points that are not required because they are acquired at a location at which one or more additional data points are acquired), and rejects at least some of the redundant data points from being used for the co-registration, as described in further detail hereinbelow.

For some applications, forward motion of the data-acquisition device is detected by acquiring images of the endoluminal device within the lumen, and performing image processing on the images in order to determine locations of the endoluminal device with respect to the lumen at the time of the acquisition of respective endoluminal image frames, e.g., in accordance with the techniques described hereinabove.

For some applications, forward motion of the endoluminal device is determined by performing the above-described mapping procedure.

For some applications, angiographic images of the data-acquisition device within the lumen are acquired in the presence of contrast agent (which makes the lumen visible in the angiographic images), and the angiographic images are image processed in order to determine locations of the endoluminal data-acquisition device marker with respect to the lumen at the time of the acquisition of respective endoluminal data points. Typically, image processing of angiographic images of the data-acquisition device within the lumen is used to identify forward motion of the data-acquisition device that is (a) due to pulsation of the lumen, or (b) due to an operator of the data-acquisition device pushing the data-acquisition device forward. This is because, in the angiographic images, the system typically identifies a visible moving portion of the endoluminal data-acquisition device (e.g., a radiopaque marker on the data-acquiring portion). Using image processing, the system tracks the motion of the visible, moving portion of the endoluminal data-acquisition device with respect to the lumen. Thus, motion of the visible, moving portion of the data-acquisition device with respect to the lumen is identifiable in the angiographic images, irrespective of the cause of the motion.

For some applications, fluoroscopic images of the data-acquisition device within the lumen are acquired in the absence of contrast agent, and the fluoroscopic images are image processed in order to determine locations of the endoluminal data-acquisition device marker with respect to the lumen at the time of the acquisition of respective endoluminal data points. For some applications, as described hereinabove, the location of a moving, visible portion of the endoluminal data-acquisition device (e.g., a radiopaque marker on the data-acquiring portion of the endoluminal data-acquisition device) is determined according to its distance along a guide wire along which the data-acquisition device is inserted, the distance typically being measured relative to the distal tip of a guiding catheter through which the guidewire and the data-acquisition device were previously inserted, and/or relative to radiopaque distal portion(s) (e.g., a radiopaque distal tip) of the guidewire. For some applications, the endoluminal data-acquisition device includes a portion that substantially does not move with respect to the lumen during pullback, such as an insertion sheath. The location of a moving, visible portion of the data-acquisition device is determined, via image processing, with reference to the portion of the device that substantially does not move with respect to the lumen during pullback. For some applications, the location of a moving, visible portion of the endoluminal data-acquisition device is determined with respect to a marker wire, over which the endoluminal data-acquisition device is inserted, in accordance with the techniques described hereinabove.

Typically, image processing of fluoroscopic images of the data-acquisition device within the lumen can be used to identify forward motion of the data-acquisition device that is due to an operator of the data-acquisition device pushing the data-acquisition device forward.

For some applications, forward motion of the endoluminal data-acquisition device that is caused by an operator pushing the data-acquisition device forward is determined using a longitudinal position/movement sensor coupled to apparatus through which the endoluminal data-acquisition device is inserted. Alternatively or additionally, forward motion of the endoluminal data-acquisition device that is caused by an operator pushing the data-acquisition device forward is determined by performing the mapping procedure described hereinabove with reference to FIG. 1A.

In response to determining that two or more endoluminal data points correspond to the same location along the lumen due to forward motion of the data-acquisition device with respect to the lumen, at least one of the data points is not used for the co-display of the endoluminal data points with an extraluminal image of the lumen. For some applications, only the first endoluminal data point that was acquired at the location is used for the co-display of the endoluminal data points with an extraluminal image of the lumen. For some applications, it is determined which at least one of the two or more endoluminal data points that correspond to the same location along the lumen was acquired during forward motion of the data-acquisition device, and this data point is rejected from being used in the co-display. Alternatively or additionally, another at least one of the two or more endoluminal data points that correspond to the same location along the lumen is rejected from being used in the co-display.

For some applications, during pullback of the endoluminal imaging device, the subject's ECG signal is detected. Respective endoluminal data points are identified as corresponding to the period in the subject's cardiac cycle at the time when the data point was acquired, based upon the detected ECG signal (e.g., by indexing the image frames with respect to the subject's ECG signal). For some applications, based upon the identified correspondence, the system determines which of the endoluminal data points were acquired in a given period of the subject's cardiac cycle, such as at least a portion of systole, and these data points are not used for the co-display of the endoluminal data points with an extraluminal image of the lumen. For example, frames corresponding to at least a portion of the subject's ECG signal between the S and T waves may be rejected from being used in the co-display. Typically, associating endoluminal data points with phases of the subject's cardiac cycle (e.g., by indexing with respect to the subject's ECG signal) can be used to account for forward motion of the endoluminal data-acquisition device that is caused by motion of the data-acquisition device with respect to the lumen due to pulsation of the lumen that is due to the subject's cardiac cycle.

For some applications, techniques described herein are used to account for the forward motion of the endoluminal data-acquisition device in order to facilitate the generation of an endoluminal data stack, the forward motion of the data-acquisition device typically being (a) due to pulsation of the lumen, and/or (b) due to an operator of the data-acquisition device pushing the data-acquisition device forward. Typically, in order to facilitate generation of an endoluminal data stack, the system identifies redundant data points (i.e., data points that are not required because they are acquired at a location at which one or more additional data points are acquired), and rejects at least some of the redundant data points from being used in the endoluminal data stack, as described in further detail hereinbelow. For some applications, in response to determining that some of the data points were acquired during forward motion of the data-acquisition device, the system places the data points in order within the data stack, and/or re-orders data points in a data stack that has already been generated, such that the data points within the stack are placed in the correct order. For some applications, the system indicates data points within a data stack that were acquired during forward motion of the data-acquisition device, for example, by highlighting portions of the data stack that were acquired during the forward motion.

For some applications, forward motion of the data-acquisition device is detected by acquiring angiographic images or fluoroscopic images of the data-acquisition device within the lumen, and performing image processing on the angiographic images in order to determine locations of the endoluminal data-acquisition device marker with respect to the lumen at the time of the acquisition of respective endoluminal data points, as described hereinabove. Typically, as described hereinabove, image processing of angiographic images is used to identify forward motion of the data-acquisition device that is caused by (a) pulsation of the lumen, or (b) an operator of the data-acquisition device pushing the data-acquisition device forward. Further typically, image processing of fluoroscopic images is used to identify forward motion of the data-acquisition device that is caused by an operator of the data-acquisition device pushing the data-acquisition device forward. For some applications, forward motion of the endoluminal data-acquisition device that is caused by an operator pushing the data-acquisition device forward is determined using a longitudinal position/movement sensor coupled to apparatus through which the endoluminal data-acquisition device is inserted. Alternatively or additionally, forward motion of the endoluminal data-acquisition device that is caused by an operator pushing the data-acquisition device forward is determined by performing the mapping procedure described hereinabove with reference to FIG. 1A.

For some applications, during pullback of the endoluminal imaging device, the subject's ECG signal is detected. Respective endoluminal data points are identified as corresponding to the period in the subject's cardiac cycle at the time when the data point was acquired, based upon the detected ECG signal (e.g., by indexing the data points with respect to the subject's ECG signal). For some applications, based upon the identified correspondence, the system determines which of the endoluminal data points were acquired in a given period of the subject's cardiac cycle, such as at least a portion of systole. Typically, associating endoluminal data points with phases of the subject's cardiac cycle (e.g., by indexing with respect to the subject's ECG signal) can be used to account for forward motion of the endoluminal data-acquisition device that is caused by motion of the data-acquisition device with respect to the lumen due to pulsation of the lumen that is due to the subject's cardiac cycle.

For some applications, in order to generate the data stack, it is determined which data points were acquired during forward motion of the endoluminal data-acquisition device (e.g., based upon image processing of angiographic or fluoroscopic images of the device inside the lumen, or based upon associating the data points with respective phases of the subject's cardiac cycle, such as, by indexing the data points with respect to the subject's ECG signal), and, in response thereto, those data points are either rejected, or are appropriately placed within the stack. For some applications, in order to generate the stack it is determined which locations along the lumen have two or more endoluminal data points corresponding thereto, and, in response thereto, at least one of the data points corresponding to the location is rejected from being used in the endoluminal data stack. Typically, only the first imaging frame to have been acquired at each location along the lumen is used in the data stack, and the other data points acquired at the location are rejected from being used in the data stack. Further typically, it is determined which at least one of the two or more endoluminal data points that correspond to the same location along the lumen was acquired during forward motion of the data-acquisition device, and this data point is rejected from being used in the data stack. Alternatively or additionally, another at least one of the two or more endoluminal data points that correspond to the same location along the lumen is rejected from being used in the data stack.

It is noted that some applications of the present invention have been described with respect to an endoluminal data-acquisition device that acquires data points while moving generally in a distal to proximal direction (i.e., during pullback of the data-acquisition device), but that experiences some movement in a proximal to distal direction. The scope of the present invention includes applying the techniques described herein to an endoluminal data-acquisition device that acquires data points while moving generally in a proximal to distal direction (i.e., while the data-acquisition device is being pushed forward through the lumen), but that experiences some movement in a distal to proximal direction, mutatis mutandis.

For some applications, in order to perform the above-described techniques, processor 20 includes (a) duplicate-data-point-identification functionality 31 configured to determine that, at at least one location, two or more endoluminal data points were acquired by the endoluminal data-acquisition device, (b) data-point-selection functionality 32 configured to generate an output using a portion of the plurality of endoluminal data points of the lumen acquired using the endoluminal data-acquisition device, by using only a single data point corresponding to the location, and (c) display-driving functionality 33 configured to drive a display to display the output.

For some applications, the processor includes (a) direction-determination functionality 34 configured to determine that, while acquiring at least one of the endoluminal data points, the endoluminal data-acquisition device was moving in a second direction that is opposite to the first direction, (b) output-generation functionality 35 configured, in response to the determining, to generate an output using at least some of the plurality of endoluminal data points of the lumen acquired using the endoluminal data-acquisition device, and (c) display-driving functionality 33 configured to drive a display to display the output.

For some applications, typically in order to facilitate co-registration of endoluminal data points to one or more extraluminal images, during (manual or automatic) pullback of an endoluminal data-acquisition device, extraluminal images of the data-acquisition device within the lumen are acquired. Image processing is performed on the extraluminal images in order to determine locations of the endoluminal data-acquisition device marker with respect to the lumen at the time of the acquisition of respective endoluminal data points, e.g., in accordance with the techniques described hereinabove. As described hereinabove, for some applications, angiographic images of the data-acquisition device within the lumen are acquired in the presence of contrast agent (which makes the lumen visible in the angiographic images), and the angiographic images are image processed in order to determine locations of the endoluminal data-acquisition device marker with respect to the lumen at the time of the acquisition of respective endoluminal data points. Alternatively or additionally, fluoroscopic images of the data-acquisition device within the lumen are acquired in the absence of contrast agent, and the fluoroscopic images are image processed in order to determine locations of the endoluminal data-acquisition device marker with respect to the lumen at the time of the acquisition of respective endoluminal data points.

For some applications, as described hereinabove, the location of a moving, visible portion of the endoluminal data-acquisition device (e.g., a radiopaque marker on the data-acquiring portion of the endoluminal data-acquisition device) is determined according to its distance along a guide wire along which the data-acquisition device is inserted, the distance typically being measured relative to the distal tip of a guiding catheter through which the guidewire and the data-acquisition device were previously inserted, and/or relative to radiopaque distal portion(s) (e.g., a radiopaque distal tip) of the guide wire. For some applications, the endoluminal data-acquisition device includes a portion that substantially does not move with respect to the lumen during pullback, such as an insertion sheath. The location of a moving, visible portion of the data-acquisition device is determined, via image processing, with reference to the portion of the device that substantially does not move with respect to the lumen during pullback. For some applications, the location of a moving, visible portion of the data-acquisition device is determined with respect to a marker wire, over which the data-acquisition device is inserted, in accordance with the techniques described hereinabove.

For some applications, motion of the data-acquisition device with respect to the lumen is determined by performing the above-described mapping procedure.

For some applications, during some of the pullback of the endoluminal data-acquisition device, the data-acquisition device moves at a different speed than the regular pullback speed of the data-acquisition device. For some applications, during some of the pullback of the endoluminal data-acquisition device, the data-acquisition device moves at a greater speed than the regular pullback speed of the data-acquisition device, such that the location of the endoluminal data-acquisition device within the extraluminal images of the lumen cannot be determined by performing image processing on the extraluminal images. For example, a region (such as a narrow region) of the lumen may provide resistance to the pullback of the data-acquisition device, such that the data-acquisition device becomes stuck for a period of time, following which the data-acquisition device pulls back quickly from the region of resistance. If, by way of example, the extraluminal imaging device acquires an extraluminal image once every ¹⁄₁₅th of a second, and the data-acquisition device pulls back from an area of resistance at a speed of 150 mm/s, then this may result in there being no extraluminal image of the data-acquisition device within a 10 mm section of the lumen. Thus, endoluminal data points that were acquired within the 10 mm section cannot be accurately co-registered to corresponding locations within the lumen in the extraluminal image. For some applications, the system identifies regions of the lumen within which the endoluminal data-acquisition device has not been imaged by the extraluminal imaging device (e.g., due to the endoluminal data-acquisition device moving through the region too quickly). In response to a user selecting a location on an extraluminal image that is within such a region, the system generates an indication that there is no endoluminal data point corresponding to that location. For example, in response to the user selecting the location, the system may not display any endoluminal data point, or the system may display an endoluminal data point corresponding to a location adjacent to the selected location, and generate an indication that this is the case. Alternatively, the system may display an endoluminal data point that was acquired by the endoluminal data-acquisition device while the data-acquisition device moved through the region, and generate an indication that the precise location within the region of the lumen corresponding to the endoluminal data point is not known.

For some applications, processor 20 identifies regions of the lumen within which the endoluminal data-acquisition device has not been imaged by the extraluminal imaging device. In response thereto, the processor displays gaps in the endoluminal data stack (e.g., the endoluminal image stack) at the locations within the stack corresponding to the regions of the lumen. Such an endoluminal image stack is shown in FIG. 3C. For some applications, the system assumes that the endoluminal data-acquisition device moved through the region at a constant speed. The system interpolates locations of endoluminal data points that were acquired by the endoluminal data-acquisition device while the data-acquisition device moved through the region, along the length of the portion of the endoluminal data stack that corresponds to the region.

For some applications, techniques described herein (e.g., techniques described with reference to FIG. 3C) are performed by a system that includes at least one processor, for use with an endoluminal data-acquisition device that acquires a plurality of endoluminal data points of a lumen of a body of a subject while being moved through the lumen generally in a first direction with respect to the lumen, and an extraluminal imaging device that images the endoluminal data-acquisition device while the endoluminal data-acquisition device is moved through the lumen. For some applications, the processor includes (a) region-identification functionality 36 configured to identify regions of the lumen within which the endoluminal data-acquisition device has not been imaged by the extraluminal imaging device, (b) output-generation functionality 35 configured to generate an output that indicates that the endoluminal data-acquisition device has not been imaged by the extraluminal imaging device within the region, and (c) display-driving functionality 33 configured to drive a display to display the output.

For some applications, the processor includes (a) region-identification functionality 36 configured to identify regions of the lumen within which the endoluminal data-acquisition device has not been imaged by the extraluminal imaging device, (b) stack-generation functionality 29 configured to generate endoluminal data stack using the plurality of endoluminal data points, and, in response to the identifying, to generate a gap in the endoluminal data stack at a portion of the stack corresponding to the region within the lumen, and (c) display-driving functionality 33 configured to drive a display to display the endoluminal data stack.

Typically, as described hereinabove, stack-generation functionality 29 is configured to generate an endoluminal data stack in which:

(a) there is at least one gap in the endoluminal data stack at a portion of the stack corresponding to a region of the lumen within which the endoluminal data-acquisition device was not imaged by the extraluminal imaging device;

(b) endoluminal data points that were acquired during forward motion of the endoluminal data-acquisition device (e.g., as determined based upon image processing of angiographic or fluoroscopic images of the device inside the lumen, or based upon associating the frames with respective phases of the subject's cardiac cycle, such as, by indexing the frames with respect to the subject's ECG signal) are either rejected, or are appropriately placed within the stack; and/or (c) at least one data point corresponding to a location along the lumen that has two or more endoluminal data points corresponding thereto is rejected from being used in the endoluminal data stack.

Typically, while an endoluminal data-acquisition device is moved through a lumen (e.g., while an IVUS probe is pulled back or pushed forward through a blood vessel), the device undergoes non-longitudinal motion. For example, the data-acquiring portion of the device (e.g., the head of the device) typically moves in an axial direction, rotates about the longitudinal axis of the device, and/or becomes tilted. For some applications, stack-generation functionality 29 determines that endoluminal data points are not aligned with each other due to non-longitudinal motion undergone by a portion of the endoluminal data-acquisition device with respect to the lumen, between acquisitions of respective endoluminal data points. In response thereto, stack-generation functionality 29 aligns the endoluminal data points with each other, to account for the non-longitudinal motion undergone by the portion of the endoluminal data-acquisition device.

For some applications, techniques are used for generating a stack of endoluminal data points (e.g., endoluminal images) in which non-uniform longitudinal motion of a portion of the endoluminal data-acquisition device is accounted for, as described in US 2012/0230565, WO 10/058,398, US 2012/0004537 and/or WO 12/014,212, all of which applications are incorporated herein by reference.

For some applications, in order to determine the angular orientation of the portion of the data-acquisition device with respect to the lumen at the time of the acquisition of respective endoluminal data points, an asymmetrically-shaped radiopaque marker that is visible in extraluminal images (e.g., angiographic or fluoroscopic images) of the lumen is disposed on the data-acquiring portion (e.g., the imaging head) of the endoluminal data-acquisition device. Alternatively or additionally, the marker may be disposed asymmetrically with respect to the longitudinal axis of the data-acquiring portion of the endoluminal data-acquisition device. During the acquisition of endoluminal data points by the endoluminal data-acquisition device, extraluminal images are acquired of the endoluminal data-acquisition device within the lumen. Image processing is applied to the fluoroscopic images in order to determine the angular orientation of the data-acquiring portion of the data-acquisition device with respect to the lumen at the time of the acquisition of respective endoluminal data points, typically automatically and typically on-line, in accordance with techniques described herein.

For some applications, endoluminal data points (e.g., images) are aligned with each other in the stack, using image processing techniques. For example, stack-generation functionality 29 may identify a region of one of the endoluminal images as having a given characteristic (e.g., being lighter than the surrounding regions). Stack-generation functionality 29 may then search for a region in an adjacent endoluminal image that has the same characteristic, and may align the adjacent image frames by aligning the regions of each of the image frames.

For some applications, endoluminal data points that are indicative of functional characteristics of the lumen are aligned with each other to account for non-longitudinal motion undergone by a portion of the endoluminal data-acquisition device with respect to the lumen, between acquisitions of respective endoluminal data points. For some applications, a sensor is coupled to the data-acquiring portion of the endoluminal data-acquisition device, and the sensor is used to determine the non-longitudinal orientation of the data-acquiring portion at times at which respective endoluminal data points are acquired.

For some applications, the aforementioned techniques are applied in order to account for unintentional rotation (typically, roll) of a portion of the endoluminal data-acquisition device with respect to the lumen, due to pulsation of the lumen, for example. For some applications, the aforementioned techniques are applied in order to facilitate the generation of an endoluminal image stack, in which the images that comprise the stack are correctly rotationally aligned. Alternatively or additionally, the aforementioned techniques are applied to determine the orientation with respect to each other of vessels that appear in the endoluminal images.

Referring again to FIG. 1A, in phase 10, the endoluminal data-acquisition device is typically retrieved from the designated site (and, further typically, withdrawn from the lumen), in order to accommodate the insertion of an endoluminal device (e.g., an endoluminal therapeutic device) into the lumen.

In phase 11, while observing an extraluminal image (and typically the roadmap image) of the luminal segment comprising the designated location, one or more locations along that segment are indicated by a user input device. In response thereto, the previously-acquired endoluminal data points (e.g., images) corresponding to the one or more locations are displayed. For some applications, the user input device is used to select the one or more locations. Typically, the user designates a location using the user input device, and, in response thereto, typically automatically and on-line, the system identifies a location along the lumen (typically along the roadmap pathway) as corresponding to the designated location, and retrieves and displays a corresponding endoluminal data point (e.g., image).

Alternatively or additionally, by observing an angiogram frame side by side with endoluminal image frames of the luminal segment comprising the designated location, one or more locations along the segment are indicated by a user input device with respect to endoluminal imaging data.

For some applications, the user indication is made upon the endoluminal image stack. For some applications, the processor generates a virtual device inside the endoluminal image stack in response to a user input. For example, a user may wish to generate an image of a device (e.g., a balloon, a stent, or a valve) inside an endoluminal image stack that has been generated in accordance with the techniques described hereinabove. The image stack has typically been (a) corrected to show gaps in the stack, (b) corrected to remove duplicate endoluminal images, (c) corrected to account for the non-longitudinal motion undergone by the endoluminal data-acquisition device, and/or (d) calibrated with respect to physical dimensions of the lumen, in accordance with the techniques described hereinabove. Thus, the endoluminal image stack typically provides to the user a representation of a cross section of the lumen that is calibrated with respect to physical dimensions of the lumen. For some applications, the user places a virtual device within the endoluminal image stack, and modifies dimensions of the device in order to determine suitable dimensions for a physical device that is to be placed inside the lumen.

For some such applications, a baseline extraluminal image (typically the roadmap image) is selected for lesion analysis and a lesion is selected by the physician for therapy. The physician then generates an indication of a desired location for placement of the endoluminal therapeutic tool on the baseline image, e.g., by virtually placing an endoluminal therapeutic tool (e.g., a balloon, a stent, or a valve) in the baseline image, by marking a target line in the baseline image, and/or by marking distal and proximal marking lines in the baseline image.

For some applications, the user indication is made by browsing through the endoluminal images. In response to receiving the user indication, the location along the lumen (e.g., along the luminal center line) within the angiogram corresponding to the location indicated with respect to an endoluminal image or the endoluminal image stack is determined and indicated.

Typically, a clinical diagnosis is facilitated by a user viewing previously-acquired endoluminal images corresponding to the one or more locations selected on extraluminal images of the luminal segment, or by the user viewing indications of locations on an extraluminal image that correspond to one or more locations selected with respect to endoluminal images or an endoluminal image stack, as described with reference to phase 11. Alternatively, a clinical diagnosis is made by the user reviewing the extraluminal images and/or the endoluminal data (and/or by reviewing other data), without performing phase 11. Typically, a therapeutic process, such as the one described in phase 12 and beyond, is performed based upon the clinical diagnosis made by the user.

In phase 12, a second endoluminal device (e.g., a diagnostic device, a second endoluminal data-acquisition device, or a therapeutic endoluminal device) is moved toward the designated location under real-time extraluminal imaging. Typically, stabilization (and optionally also enhancement) is applied, typically on-line and typically automatically, to the extraluminal image stream.

In phase 13, using the above-described mapping algorithm, the current location of the second endoluminal device, determined via image-processing that is performed on the current extraluminal images, is mapped to the roadmap image. The current device location is indicated in the roadmap image. Typically, in cases in which the second device is a therapeutic device, in response to the mapping, the physician deploys the endoluminal therapeutic device, in response to the roadmap image indicating that the mapped location of the therapeutic device within the roadmap image corresponds to the desired location of the device as indicated within the roadmap image.

It is noted that, in general, the scope of the present invention includes using the technique of mapping extraluminal images of a device inside a lumen to a baseline roadmap image of the lumen (using the techniques described hereinabove with respect to phases 6-7), in order to determine the location of a device with respect to the roadmap image at times corresponding to respective extraluminal images, and generating an output in response thereto. Although with reference to FIG. 1A, the mapping is described as being performed for the purpose of co-registering endoluminal images to an extraluminal roadmap image, for some applications, in response to the mapping, the on-line location of an endoluminal device with respect to the roadmap pathway is determined and is displayed upon the roadmap. For example, the on-line location of the endoluminal data-acquisition device with respect to the roadmap pathway may be determined, by mapping an on-line extraluminal image of the endoluminal data-acquisition device inside the lumen to the roadmap image using the mapping technique described hereinabove. In response thereto, the on-line location of the endoluminal data-acquisition device may be displayed upon the roadmap image. Alternatively or additionally, the on-line location of a different endoluminal device (e.g., the endoluminal therapeutic device) with respect to the roadmap pathway may be determined, by mapping an on-line extraluminal image of the endoluminal device inside the lumen to the roadmap image using the mapping technique described hereinabove. In response thereto, the on-line location of the endoluminal device may be displayed upon the roadmap image. Further alternatively or additionally, the location of the endoluminal data-acquisition device with respect to the roadmap pathway may be determined, and in response thereto, endoluminal data points may be co-registered to locations along the roadmap pathway, in accordance with the techniques described hereinabove.

It is noted that, in general, the scope of the present invention includes determining a plurality of local calibration factors associated with respective locations on a roadmap image (using the techniques described hereinabove with respect to phase 8), and generating an output in response thereto. Typically, the local calibration factors are determined based upon known dimensions associated with features that are identified in images belonging to a second set of extraluminal images, in accordance with the techniques described hereinabove. Although with reference to FIG. 1A, the mapping is described as being performed for the purpose of co-registering endoluminal images to an extraluminal roadmap image, for some applications, based upon the local calibration factors, the on-line location of an endoluminal device with respect to the roadmap pathway is determined and is displayed upon the roadmap. For example, the on-line location of the endoluminal data-acquisition device with respect to the roadmap pathway may be determined, by mapping an on-line extraluminal image of the endoluminal data-acquisition device inside the lumen to the roadmap image, using the mapping technique described hereinabove, and based upon determined local calibration factors associated with the roadmap image. In response thereto, the on-line location of the endoluminal data-acquisition device may be displayed upon the roadmap image. Alternatively or additionally, the on-line location of a different endoluminal device (e.g., the endoluminal therapeutic device) with respect to the roadmap pathway may be determined, by mapping an on-line extraluminal image of the endoluminal device inside the lumen to the roadmap image, using the mapping technique described hereinabove, and based upon determined local calibration factors associated with the roadmap image. In response thereto, the on-line location of the endoluminal device may be displayed upon the roadmap image. Further alternatively or additionally, the location of the endoluminal data-acquisition device with respect to the roadmap pathway may be determined, using the mapping technique described hereinabove, and based upon determined local calibration factors associated with the roadmap image. In response thereto, endoluminal data points may be co-registered to locations along the roadmap pathway, in accordance with the techniques described hereinabove.

Data points (e.g., images) that were previously acquired by the endoluminal data-acquisition device at or near the location are retrieved and associated, typically on-line and typically automatically, with the extraluminal imaging, while the device is at or near the same location.

In phase 14, data points (e.g., images) that were previously acquired by the endoluminal data-acquisition device at or near the location are displayed together with the extraluminal imaging. Typically, data points are displayed that correspond to the current location of the endoluminal therapeutic device (as determined in phase 9). Typically, phases 13 and 14 are performed in real-time with respect to phases 11 and 12. Thus, while the endoluminal therapeutic device is at respective current locations inside the lumen, the location of the device is determined, and the endoluminal data points associated with the location are retrieved and displayed.

For some applications, data acquired by a first endoluminal modality (e.g., IVUS) are co-registered with the roadmap image, in accordance with the techniques described hereinabove. Subsequently, data acquired by a second endoluminal modality (e.g., OCT) are co-registered with the roadmap image, in accordance with the applications described hereinabove. Consequently, due to both data sets being co-registered with the roadmap image, the two data sets are co-registered to one another. For some applications, the two endoluminal data sets are displayed as overlaid or otherwise merged with one another.

For some applications, in response to determining the current location of the second endoluminal device with respect to the roadmap pathway, the display-driving functionality is configured to drive a display to display an image of the second endoluminal device at the corresponding location within the endoluminal image stack. In accordance with respective applications, a virtual image of the second device, or a real image of the second device, is displayed within the endoluminal image stack.

Figure 4:
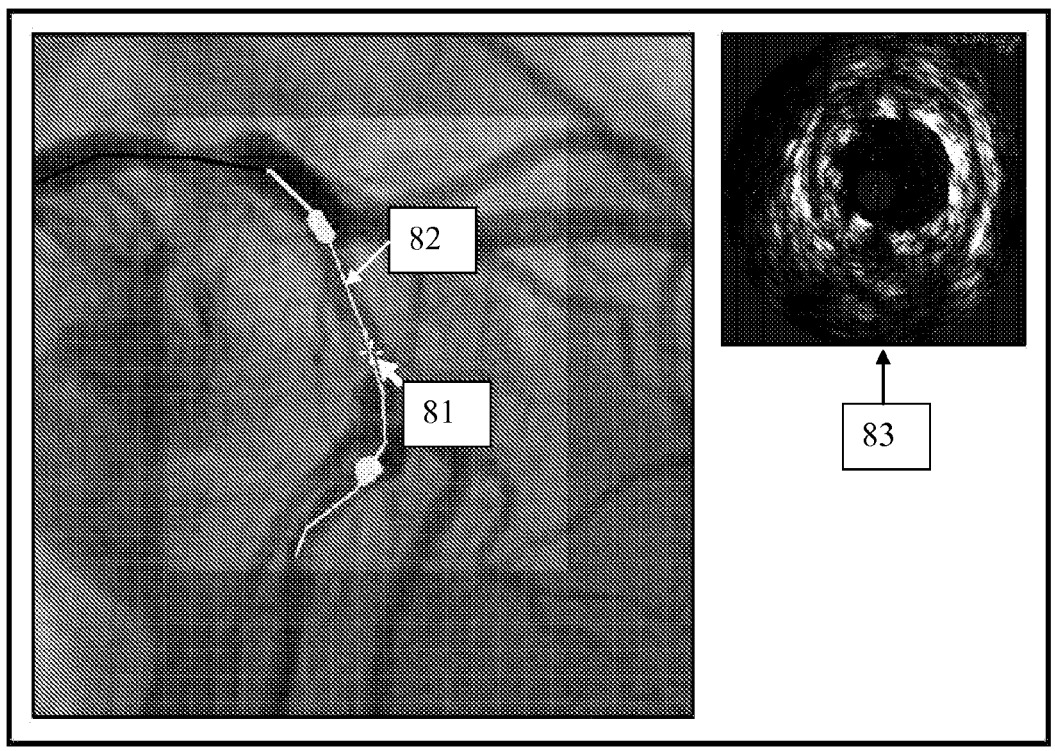
FIG. 4 shows the co-use of previously-acquired endoluminal images and an extraluminal fluoroscopic image, in accordance with some applications of the present invention.

Reference is now made to FIG. 4, which is schematic illustration of a screen on which an IVUS image 83 is displayed, in accordance with some applications of the present invention. Typically, upon receiving an indication from the user of a location along the lumen (e.g., along the luminal center line 82, for example, by the user pointing cursor 81 to a location on the screen, and the system determining a location along the center line corresponding to the location), IVUS image 83 which was previously acquired at that location is displayed. For some applications, an IVUS stack comprising data from IVUS images that were previously acquired along a section of the lumen (e.g., along a section of center line 82) of which the user-indicated location is a middle point or one of the end points, is displayed. For some applications, an IVUS stack comprising data from IVUS images that were previously acquired between two user-indicated locations along the lumen (e.g., along center line 82) is displayed. For some applications, similar techniques are performed using an endoluminal imaging modality other than IVUS.

For some applications, a three-dimensional "tunnel-like" reconstruction of the IVUS images of the vessel (or a section thereof, such as those corresponding to the longitudinal section between the current locations of the proximal and distal markers of the balloon/stent) is generated and displayed. For some applications, the IVUS images are overlaid on the fluoroscopic images. For some applications, the IVUS images are fused with the fluoroscopic images. For some applications, a combination of the aforementioned display techniques is applied. For some applications, an indication of the motion range of the balloon/stent relative to the lumen, resulting from the cardiac cycle, is displayed in conjunction with any of the aforementioned displays of the IVUS images. For some applications, such an indication is generated and/or displayed in accordance with embodiments of US 2010/0222671 to Cohen, which is incorporated herein by reference. For some applications, similar techniques are performed using an endoluminal imaging modality other than IVUS.

It is noted that in applying any of the techniques described hereinabove for associating endoluminal images with respective locations along the lumen, the system typically accounts for a known offset between the location of the moving, visible portion of the endoluminal data-acquisition devices (e.g., a radiopaque marker), and the location of the data-acquiring portion of the probe (e.g., the ultrasound transducer, in the case of an IVUS probe).

It is noted that some of the techniques described hereinabove for associating endoluminal images with respective locations along the lumen are described with reference to an endoluminal data-acquisition device that acquires endoluminal data points during pullback of the device. The scope of the present invention includes applying any of the techniques described hereinabove for associating endoluminal data points with respective locations along the lumen to an endoluminal data-acquisition device that acquires endoluminal data points during insertion and advancement of the device through the lumen (e.g., when images are acquired from an endobronchial airway), mutatis mutandis.

For some applications, pullback of the endoluminal data-acquisition device is performed in the course of a continuous injection of contrast agent performed under fluoroscopic imaging. For example, the endoluminal data-acquisition device may be an OCT probe, the image acquisition of which typically requires concurrent flushing of the lumen, in order to remove blood from the lumen, the blood interfering with the OCT imaging. Furthermore, contrast agent highlights the lumen and facilitates angiographic imaging of the lumen. Still furthermore, for some applications, the presence of contrast agent in the lumen facilitates acquisition of OCT data. Therefore, typically, during endoluminal imaging with an OCT probe, contrast agent is continuously injected into the lumen. In addition, the pullback of the OCT probe is typically performed rapidly relative to the pullback of an IVUS probe, and the frame acquisition rate of the OCT probe is typically greater than that of an IVUS probe.

For some applications, a procedure is performed in order to co-register OCT images to an extraluminal image of the lumen, the procedure including at least some of the following steps:

1) The OCT probe is inserted under extraluminal fluoroscopic imaging. The OCT probe typically includes one or more radiopaque portions that move in conjunction with the data-acquiring portion (e.g., the head) of the probe, and that have a known dimension associated therewith. For example, the data-acquiring portion of the probe itself is typically radiopaque and has a known dimension. In addition, the probe may have radiopaque markers that move in conjunction with the data-acquiring portion of the probe and that are separated from each other by a known distance. Typically, the one or more radiopaque portions are identified in the extraluminal fluoroscopic images.

2) Pullback of the OCT probe commences at a known and steady speed (typically by means of automated pullback), in conjunction with contrast agent injection performed under angiographic imaging. The image slices generated by the OCT along the pullback are recorded and stored together with an indication of the time of acquisition and/or the frame number of each of the images.

3) A roadmap image is selected from the angiographic sequence, in accordance with the techniques described hereinabove. A roadmap pathway is designated within the roadmap image, in accordance with the techniques described hereinabove.

4) The fluoroscopic images that were acquired during the insertion of the OCT probe are mapped to the roadmap image, in accordance with the techniques described hereinabove. Local calibration factors along the roadmap pathway are determined, based upon the mapping, in accordance with the techniques described hereinabove.

5) The starting location along the roadmap pathway at which the probe was disposed at the initiation of the pullback of the probe is determined.

6) The pullback speed of the OCT probe is known. In addition, the frame rate of the OCT probe is known. Therefore, the distance along the lumen between adjacent OCT images is known. Furthermore, the local calibration factors for calibrating pixels along the roadmap pathway to the physical dimensions of the lumen are typically known (based upon implementing the above-described techniques). Thus, for any one of the OCT frames, the distance from the starting location at which the OCT frame was acquired is determined, based upon the speed at which the endoluminal data-acquisition device was moved through the lumen, the frame rate at which the endoluminal data points were acquired, and the local calibration factors associated with the respective locations within the lumen. For example, if it is known, based upon the speed of the pullback and the frame rate, that images are acquired at intervals of 0.25 mm, then it is determined that the OCT image corresponding to a location that is 15 mm along the lumen from the pullback starting location is the 60th image frame. Thus, for some applications, co-registration functionality 28 of processor 20 co-registers respective endoluminal data points to respective locations within the roadmap image, by (a) identifying the starting location of the endoluminal data-acquisition device in the roadmap image, and (b) determining a distance from the starting location at which respective endoluminal data points were acquired, based upon the speed at which the endoluminal data-acquisition device was moved through the lumen, the frame rate at which the endoluminal data points were acquired, and the local calibration factor associated with the respective portions of the roadmap image.

7) Based upon the co-registering of the OCT images to the roadmap image, techniques as described hereinabove for displaying endoluminal images in conjunction with extraluminal images are performed. For example, in response to a user indicating a location along the lumen on an extraluminal image, the corresponding OCT image may be displayed. Or, an OCT image stack may be corrected using the techniques described hereinabove, and may then be displayed, and/or used to facilitate length measurements along the roadmap pathway. For some applications, length measurements are displayed on the OCT image stack. For some applications, measurements are automatic. For some applications, measurements are performed interactively by the user. For some applications, a scale (or some other known dimension) presented on the OCT images provides a reference dimension for calibrating the measurements. For some applications, a virtual device (e.g., a stent, a balloon, and/or a valve) is displayed a upon the OCT image stack, typically at a user-indicated location.

It is noted that although the above-described technique was described with respect to OCT imaging, the scope of the present invention includes performing the above-described technique using other endoluminal imaging modalities (such as IVUS and/or other imaging techniques described hereinabove), mutatis mutandis. It is further noted that although the above-described technique was described with respect to endoluminal images that are acquired during pullback of the device, the scope of the present invention includes performing the above-described technique using endoluminal images that are acquired while the imaging device is advanced through the lumen, mutatis mutandis. It is still further noted that although in the above-described technique, step (1) is described as being performed before steps (2) and (3), the scope of the present invention includes performing steps (2) and (3) and, subsequently, performing step (1).

For some applications, data acquired by a first endoluminal modality (e.g., IVUS) are co-registered with the fluoroscopic image stream, in accordance with the applications described hereinabove. Subsequently, data acquired by a second endoluminal modality (e.g., OCT) are co-registered with the fluoroscopic image stream, in accordance with the applications described hereinabove. Consequently, due to both data sets being co-registered with the fluoroscopic image stream, the two data sets are co-registered to one another. For some applications, the two endoluminal data sets are displayed overlaid or otherwise merged with one another.

For some applications, generally similar steps to those described with reference to FIG. 1A are performed, except for the following differences. In phase 12, instead of a therapeutic endoluminal device (e.g., a treatment catheter) being inserted into the lumen, a second endoluminal data-acquisition device is inserted into the lumen. Typically, the first and second endoluminal data-acquisition devices acquire endoluminal images using respective imaging modalities. For example, in phase 1, an IVUS probe may be inserted into the lumen, and in phase 12 an OCT probe may be inserted into the lumen, or vice versa.

The current location of the second endoluminal data-acquisition device is determined, for example, using any of the techniques described herein (such as, by performing image processing on extraluminal images of the second endoluminal data-acquisition device inside the lumen). Endoluminal images which were previously acquired using the first data-acquisition device at the current location of the second endoluminal data-acquisition device are retrieved and displayed, typically on-line and typically automatically.

Typically, the endoluminal images which were acquired using the first data-acquisition device at the current location of the second endoluminal data-acquisition device are displayed together with endoluminal images that are being acquired in real-time by the second endoluminal data-acquisition device, while the second endoluminal data-acquisition device is at the current location. For some applications, endoluminal images that are acquired in real-time by the second endoluminal data-acquisition device, while the second endoluminal data-acquisition device is at the current location, are displayed together with an indication of the current location of the second endoluminal data-acquisition device with respect to an endoluminal image stack generated using endoluminal images that were previously acquired by the first endoluminal data-acquisition device. For some applications, using the above-described technique, data acquired by first and second endoluminal data-acquisition devices are registered with respect to one another, and the co-registered data are displayed subsequent to termination of the acquisition of endoluminal images by both the first and the second endoluminal data-acquisition devices. For some applications, endoluminal images corresponding to the current location of the second endoluminal data-acquisition device that were acquired by the first endoluminal data-acquisition device and/or by the second endoluminal data-acquisition device are co-displayed with an indication of the current location of the second endoluminal data-acquisition device on an extraluminal image of the lumen, using the techniques described herein.

For some applications, locations along the lumen of an endoluminal data-acquisition device associated with a first endoluminal data-acquisition modality (e.g., IVUS) are identified as corresponding to respective endoluminal data points of the first data-acquisition modality, in accordance with the techniques described hereinabove. Subsequently, locations along the lumen of an endoluminal data-acquisition device associated with a second data-acquisition modality (e.g., OCT) are identified as corresponding to respective endoluminal data points of the second data-acquisition modality, in accordance with the techniques described hereinabove. For example, forward motion of one or both of the endoluminal data-acquisition devices may be accounted for in associating the locations of the endoluminal data-acquisition devices with the image frames, in accordance with techniques described hereinabove. Consequently, the two data sets are co-registered to one another. For some applications, the two endoluminal data sets are displayed overlaid or otherwise merged with one another.

Figure 5:
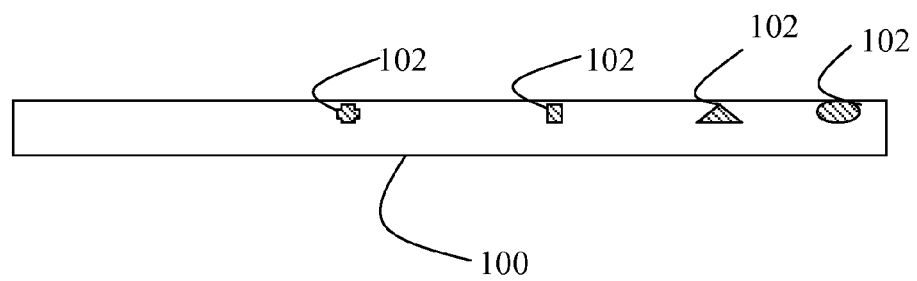
FIG. 5 is a schematic illustration of a reference tool having markers coupled thereto, a characteristic of the markers varying along the length of at least a portion of the reference tool, in accordance with some applications of the present invention.

Reference is now made to FIG. 5, which is schematic illustration of a reference tool 100 having coupled thereto radiopaque markers 102, a characteristic of the markers varying along a least a portion of the reference tool, in accordance with some applications of the present invention. For example, as shown, the separation between adjacent markers may vary along at least a portion of the reference tool. Alternatively or additionally, also as shown, shapes of the markers may vary along at least a portion of the reference tool. For some applications, the reference tool is a wire (e.g., a guidewire), or a sheath that is used to facilitate the insertion of an endoluminal device (e.g., an endoluminal data-acquisition device) into a lumen.

For some applications, reference tool 100 is inserted into a lumen. An endoluminal device (e.g., an endoluminal data-acquisition device) is inserted into the lumen under extraluminal imaging (e.g., fluoroscopic imaging), the endoluminal device having a radiopaque portion (e.g., a radiopaque marker) associated therewith. For example, the data-acquiring portion of an endoluminal data-acquisition device may be radiopaque, and/or may have radiopaque markers coupled thereto. The location of the endoluminal device within the lumen is determined by determining, via image processing, the location of the radiopaque portion that is associated with the endoluminal device, with reference to the radiopaque markers of the reference tool. For some applications, by determining the location of the radiopaque portion that is coupled to the endoluminal device with reference to the radiopaque markers of the reference tool, errors in the determination of the location of the endoluminal device with respect to the lumen (e.g., errors that are caused by foreshortening of the lumen) are reduced, relative to if the system were not to use the radiopaque markers of the reference tool as reference points.

For some applications, the distances between respective pairs of markers that are adjacent to one another varies along the length of the reference tool, and/or a shape or pattern of the markers varies along the length of the reference tool. For some applications, using such a reference tool facilitates determining the location of the endoluminal device with reference to the radiopaque markers of the reference tool, even if only a portion, and not all, of the markers on the wire are visible to the extraluminal imaging system. For example, the shapes or patterns of the markers and/or the distances between respective pairs of markers that are adjacent to one another may vary such that any set of markers (e.g., any pair, or set of three or four of the markers) has a unique appearance. Thus, when the radiopaque portion that is coupled to the endoluminal device appears in an image in a vicinity of a given set of markers, the location of the device along the lumen with respect to the reference tool may be determined by the system.

For some applications, reference tool 100 is used together with an endoluminal data-acquisition device in order to facilitate registration of endoluminal data points that are acquired by the data-acquisition device to an extraluminal image of the lumen, for example, using generally similar techniques to those described herein and/or generally similar techniques to those described in US 2012/0004537 and/or WO 12/014,212, both of which applications are incorporated herein by reference.

It is noted that although some techniques for co-using extraluminal images and endoluminal data are described hereinabove primarily with respect to extraluminal fluoroscopic/angiographic images and endoluminal IVUS images, the scope of the present invention includes applying the techniques described herein to other forms of extraluminal and endoluminal images and/or data, mutatis mutandis. For example, the extraluminal images may include images generated by fluoroscopy, CT, MRI, ultrasound, PET, SPECT, other extraluminal imaging techniques, or any combination thereof. Endoluminal images may include images generated by optical coherence tomography (OCT), near-infrared spectroscopy (NIRS), intravascular ultrasound (IVUS), endobronchial ultrasound (EBUS), magnetic resonance (MR), other endoluminal imaging techniques, or any combination thereof. Endoluminal data may include data related to pressure (e.g., fractional flow reserve), flow, temperature, electrical activity, or any combination thereof. Examples of the anatomical structure to which the aforementioned co-registration of extraluminal and endoluminal images may be applied include a coronary vessel, a coronary lesion, a vessel, a vascular lesion, a lumen, a luminal lesion, and/or a valve. It is noted that the scope of the present invention includes applying the techniques described herein to lumens of a subject's body other than blood vessels (for example, a lumen of the gastrointestinal or respiratory tract).

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
    an endoluminal data-acquisition device configured to acquire a plurality of endoluminal data points while moving through a lumen of a subject's body;
    a second endoluminal device configured to be moved through the lumen;
    a display; and
    at least one processor configured to:
        determine that respective endoluminal data points correspond to respective locations along the lumen,
        generate a stack of the endoluminal data points, in which the endoluminal data points are positioned at locations corresponding to relative locations within the lumen at which the endoluminal data points were acquired,
        while the second endoluminal device is inside the lumen, and while the endoluminal data-acquisition device is in a retrieved state with respect to the lumen, subsequent to the endoluminal data-acquisition device having acquired the plurality of endoluminal data points while moving through the lumen,
        determine a current location of the second endoluminal device with respect to the lumen, and
        drive the display to display the stack, and to display within the stack an image of the second endoluminal device at a location within the stack corresponding to the current location of the second endoluminal device.

2. The apparatus according to claim 1, wherein the processor is configured to drive the display to display the image of the second endoluminal device within the stack by driving the display to display a virtual representation of the second endoluminal device within the stack.

3. The apparatus according to claim 1, wherein the processor is configured to drive the display to display the image of the second endoluminal device within the stack by driving the display to display a real image of the second endoluminal device within the stack.

4. The apparatus according to claim 1, wherein the second endoluminal device comprises a therapeutic endoluminal device.

5. The apparatus according to claim 1, wherein the endoluminal data-acquisition device comprises an endoluminal imaging device that is configured to acquire a plurality of endoluminal images while the endoluminal imaging device is being moved through the lumen, and wherein the processor is configured to generate the stack by generating an endoluminal image stack.

6. The apparatus according to claim 1, wherein the endoluminal data-acquisition device comprises an endoluminal data-acquisition device that is configured to acquire functional data regarding the lumen while the endoluminal data-acquisition device is being moved through the lumen, and wherein the processor is configured to generate the stack by generating a stack of functional endoluminal data points.

7. The apparatus according to claim 1, wherein the processor is configured to generate the stack of endoluminal data points by generating a stack of indications of the endoluminal data points, locations of the indications within the stack corresponding to relative locations within the lumen at which the endoluminal data points were acquired.

8. The apparatus according to claim 1, wherein the processor is configured to generate the stack of the endoluminal data points, by generating a stack of endoluminal data points that includes a gap at a location within the stack corresponding to a location within the lumen at which no endoluminal data points were acquired.

9. The apparatus according to claim 1, wherein the processor is configured to generate the stack of the endoluminal data points, by generating a stack of endoluminal data points in which duplicate endoluminal data points are removed from the stack at locations within the stack corresponding to locations within the lumen at which more than one endoluminal data point was acquired.

10. The apparatus according to claim 1, wherein the processor is configured to generate the stack of the endoluminal data points, by generating a stack of endoluminal data points, by accounting for non-longitudinal motion undergone by the endoluminal data-acquisition device, while acquiring the plurality of endoluminal data points, while moving through the lumen.

11. The apparatus according to claim 1, wherein the processor is configured to generate the stack of the endoluminal data points, by generating a stack of endoluminal data points that is calibrated with respect to physical dimensions of the lumen.

12. The apparatus according to claim 1, wherein the processor is configured to generate the stack of the endoluminal data points, by generating a stack of endoluminal data points, a cross section of the stack being calibrated with respect to physical dimensions of the lumen.

13. A method for use with an endoluminal data-acquisition device configured to acquire endoluminal data points while moving through a lumen of a subject's body, a second endoluminal device, and a display, the method comprising:
while the endoluminal data-acquisition device is being moved through the lumen, acquiring a plurality of endoluminal data points of the lumen using the endoluminal data-acquisition device;
using at least one processor, determining that respective endoluminal data points correspond to respective locations along the lumen;
using the processor, driving the display to display at least some of the plurality of endoluminal data points in a stack, in which the endoluminal data points are positioned at locations corresponding to relative locations within the lumen at which the endoluminal data points were acquired;
using the processor, while the second endoluminal device is inside the lumen, and while the endoluminal data-acquisition device is in a retrieved state with respect to the lumen, subsequent to the endoluminal data-acquisition device having acquired the plurality of endoluminal data points while moving through the lumen, determining a current location of at least a portion of the second endoluminal device with respect to the lumen; and
in response thereto, displaying within the stack an image of the second endoluminal device at a location within the stack corresponding to the current location of the second endoluminal device.

14. The method according to claim 13, wherein displaying the image of the second endoluminal device within the stack comprises displaying a virtual representation of the second endoluminal device within the stack.

15. The method according to claim 13, wherein displaying the image of the second endoluminal device within the stack comprises displaying a real image of the second endoluminal device within the stack.

16. The method according to claim 13, wherein the second endoluminal device includes a therapeutic endoluminal device, and wherein determining the current location of at least a portion of the second endoluminal device with respect to the lumen comprises determining a current location of at least a portion of the therapeutic endoluminal device with respect to the lumen.

17. The method according to claim 13, wherein the endoluminal data-acquisition device includes an endoluminal imaging device that is configured to acquire a plurality of endoluminal images while the endoluminal imaging device is being moved through the lumen, and wherein driving the display to display at least some of the plurality of endoluminal data points in a stack comprises driving the display to display an endoluminal image stack.

18. The method according to claim 13, wherein the endoluminal data-acquisition device includes an endoluminal data-acquisition device that is configured to acquire functional data regarding the lumen while the endoluminal data-acquisition device is being moved through the lumen, and wherein driving the display to display at least some of the plurality of endoluminal data points in a stack comprises driving the display to display a stack of functional endoluminal data points.

19. The method according to claim 13, wherein driving the display to display at least some of the plurality of endoluminal data points in a stack comprises driving the display to display a stack of indications of the endoluminal data points, locations of the indications within the stack corresponding to relative locations within the lumen at which the endoluminal data points were acquired.

20. The method according to claim 13, wherein driving the display to display at least some of the plurality of endoluminal data points in a stack comprises driving the display to display a stack of endoluminal data points that includes a gap at a location within the stack corresponding to a location within the lumen at which no endoluminal data points were acquired.

21. The method according to claim 13, wherein driving the display to display at least some of the plurality of endoluminal data points in a stack comprises driving the display to display a stack of endoluminal data points in which duplicate endoluminal data points are removed from the stack at locations within the stack corresponding to locations within the lumen at which more than one endoluminal data point was acquired.

22. The method according to claim 13, wherein driving the display to display at least some of the plurality of endoluminal data points in a stack comprises driving the display to display a stack of endoluminal data points, by accounting for non-longitudinal motion undergone by the endoluminal data-acquisition device, while acquiring the plurality of endoluminal data points, while moving through the lumen.

23. The method according to claim 13, wherein driving the display to display at least some of the plurality of endoluminal data points in a stack comprises driving the display to display a stack of endoluminal data points that is calibrated with respect to physical dimensions of the lumen.

24. The method according to claim 13, wherein driving the display to display at least some of the plurality of endoluminal data points in a stack comprises driving the display to display a stack of endoluminal data points, a cross section of the stack being calibrated with respect to physical dimensions of the lumen.

* * * * *